(12) United States Patent
Coats et al.

(10) Patent No.: US 8,362,247 B2
(45) Date of Patent: *Jan. 29, 2013

(54) PROKINETICIN 1 RECEPTOR ANTAGONISTS

(75) Inventors: Steven J. Coats, Quakertown, PA (US); Alexey B. Dyatkin, Maple Glen, PA (US); Wei He, Audubon, PA (US); Joseph Lisko, Collegeville, PA (US); Tamara A. Miskowski, Chalfont, PA (US); Janet L. Ralbovsky, North Wales, PA (US); Mark J. Schulz, Skippack, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/113,751

(22) Filed: May 23, 2011

(65) Prior Publication Data

US 2012/0129862 A1    May 24, 2012

Related U.S. Application Data

(62) Division of application No. 11/375,407, filed on Mar. 14, 2006, now Pat. No. 7,968,710.

(60) Provisional application No. 60/665,002, filed on Mar. 24, 2005.

(51) Int. Cl.
| | |
|---|---|
| C07D 403/06 | (2006.01) |
| C07D 403/12 | (2006.01) |
| C07D 403/14 | (2006.01) |
| C07D 401/06 | (2006.01) |
| C07D 401/12 | (2006.01) |
| C07D 401/14 | (2006.01) |
| A61K 31/506 | (2006.01) |
| A61P 1/00 | (2006.01) |
| A61P 1/06 | (2006.01) |

(52) U.S. Cl. ........ 544/309; 544/310; 544/311; 514/269; 514/274

(58) Field of Classification Search ............... 544/309, 544/310, 311; 514/269, 274
See application file for complete search history.

(56) References Cited

U.S. PATENT DOCUMENTS

| | | | |
|---|---|---|---|
| 3,959,469 A | 5/1976 | Kay | |
| 6,485,938 B1 | 11/2002 | Sheppard et al. | |
| 7,902,358 B2 * | 3/2011 | Coats et al. | 544/223 |
| 7,968,710 B2 * | 6/2011 | Coats et al. | 544/223 |
| 2003/0225075 A1 | 12/2003 | Agarwal et al. | |
| 2004/0156842 A1 | 8/2004 | Thompson et al. | |
| 2007/0021422 A1 | 1/2007 | Mabus et al. | |

FOREIGN PATENT DOCUMENTS

| | | | |
|---|---|---|---|
| WO | WO 0236625 A2 | 5/2002 | |
| WO | WO 2004/087054 A2 | 10/2004 | |
| WO | WO 2004/113361 A3 | 12/2004 | |
| WO | WO 2005/007164 A1 | 1/2005 | |
| WO | WO 2005/091925 A2 | 10/2005 | |
| WO | WO 2006/104713 A1 | 10/2006 | |

OTHER PUBLICATIONS

Freshney et al., Culture of Animal Cells, A Manual of Basic Technique, Alan R. Liss, Inc., 1983, New York, p4.*
Dermer et al., Bio/Technology, 1994, 12:320.*
Golub et al., Science, 286, 531-537, 1999.*
Cecil Textbook of Medicine, edited by Bennet, J.C., and Plum F., 20th edition, vol. 1, 1004-1010, 1996.*
Zhou et al., Molecular Interventions, vol. 6(6), 330-338, 2006.*
Akehurst, R. and Kaltenthaler, E. "Treatment of Irritable Bowel Syndrome: a Review of Randomized Controlled Trials.", *Gut*, 2001, pp. 272-282, vol. 48(2).
Berge et al., "Pharmaceutical Salts.", *J. Pharm. Sci.*, 1977, pp. 1-19, vol. 66(1).
Bullock et al., "Identification of Two Prokineticin cDNAs: Recombinant Proteins Potently Contract Gastrointestinal Smooth Muscle.", *Mol. Pharmacol.*, 2001, pp. 692-698, vol. 59(4).
Bullock et al., "Structural Determinants Required for the Bioactivities of Prokineticins and Identification of Prokineticin Receptor Antagonists.", *Mol. Pharmacol.*, Mar. 2004, pp. 582-588, vol. 65(3).
Cathala et al., "Laboratory Methods. A Method for Isolation of Intact, Translationally Active Ribonucleic Acid.", *DNA*, 1983, pp. 329-335, vol. 2(4).
Goi et al., "Angiogenesis and Tumor Proliferation/Metastasis of Human Colorectal Cancer Cell Line SW620 Transfected with Endocrine Glands-Derived-Vascular Endothelial Growth Factor, As a New Angiogenic Factor.", *Cancer Research*, Mar. 15, 2004, pp. 1906-1910, vol. 64.
Gould P.L., "Salt Selection for Basic Drugs.", International J. Pharm., 1986, pp. 201-217, vol. 33.
Jackson et al., "Treatment of Functional Gastrointestinal Disorders with Antidepressant Medications: A Meta-Analysis.", *Am. J. Med.*, 2000, pp. 65-72, vol. 108.

(Continued)

*Primary Examiner* — Venkataraman Balasubramanian
(74) *Attorney, Agent, or Firm* — Timothy E. Tracy

(57) ABSTRACT

The present invention relates to certain novel compounds of Formula (I):

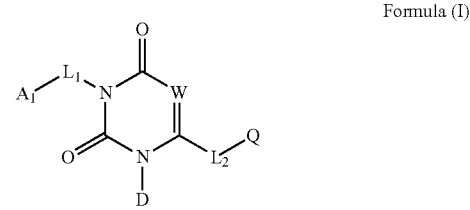

Formula (I)

and methods for preparing these compounds, compositions, intermediates and derivatives thereof and for the treatment of prokineticin 1 or prokinetin 1 receptor mediated disorders.

47 Claims, 5 Drawing Sheets

OTHER PUBLICATIONS

Jailwala et al., "Pharmacologic Treatment of the Irritable Bowel Syndrome: A Systematic Review of Randomized, Controlled Trials.", *Ann. Intern. Med.*, Jul. 18, 2000, pp. 136-147, vol. 133(2).

Lecouter et al., "Identification of an angiogenic mitogen selective for endocrine gland endothelium.", *Nature*, Aug. 30, 2001, pp. 877-884, vol. 412.

Lecouter et al., "The Role of EG-VEGF in the Regulation of Angiogenesis in Endrocrine Glands.", *Cold Spring Harb Symp Quant Biol.*, 2002, pp. 217-221, vol. LXVII.

Lecouter et al., "The endocrine-gland-derived VEGF homologue Bv8 promotes angiogenesis in the testis: Localization of Bv8 receptors to endothelial cells.", *Proc. Natl. Acad. Sci.*, Mar. 4, 2003, pp. 2685-2690, vol. 100(5), U.S.A.

Masuda et al., "Isolation and identification of EG-VEGF/prokineticins as cognate ligands for two orphan G-protein-coupled receptors.", *Biochem. Biophys. Res. Commun.*, 2002, pp. 396-402, vol. 293(1).

Mollay et al., "Bv8, a small protein from frog skin and its homologue from snake venom induce hyperalgesia in rats.", *Eur. J. Pharmacol.*, 1999, pp. 189-196, vol. 374.

Negri et al., "Nociceptive sensitization by the secretory protein Bv8.", *Brit. J. Pharmacol.*, 2002, pp. 1147-1154, vol. 137(8).

Negri et al., "Bv8, the amphibian homologue of the mammalian prokineticins, modulates ingestive behaviour in rats.", *Brit. J. Pharmacol.*, May 2004, pp. 181-191, vol. 142(1).

Poynard et al., "Meta-analysis of smooth muscle relaxants in the treatment of irritable bowel syndrome.", *Aliment Pharmacol. & Ther.*, 2001, pp. 355-361, vol. 15(3).

Saito et al., "The Epidemiology of Irritable Bowel Syndrome in North America: A Systematic Review.", *Am. J. Gastroenterol.*, 2002, pp. 1910-1915, vol. 97(8).

Schweitz et al., "MIT(1), a black mamba toxin with a new and highly potent activity on intestinal contraction.", *FEBS Lett.*, 1999, pp. 183-199, vol. 461(3).

Thompson, W.G. and Heaton, K.W., "Functional Bowel Disorders in Apparently Healthy People.", *Gastroenterology*, 1980, pp. 283-288, vol. 79.

International Search Report relating to International Patent Application No. PCT/US2006/009613. Date of Mailing of International Search Report: Aug. 30, 2006.

Written Opinion of the International Searching Authority relating to International Patent Application No. PCT/US2006/009613. Date of Mailing of Written Opinion: Aug. 30, 2006.

* cited by examiner

Matrix Assisted Laser Desorption (MALDI) mass spectrum of protein mixture.

The PK1-evoked increase in Isc was inhibited by Cpd 2.

The PK1-evoked increase in Isc was inhibited by Cpd 58.

PROKINETICIN 1 RECEPTOR ANTAGONISTS

CROSS REFERENCE TO RELATED APPLICATIONS

This Application is a divisional of U.S. application Ser. No. 11/375,407 filed Mar. 14, 2006, now U.S. Pat. No. 7,968,710, and in turn claims priority to U.S. Provisional Patent Application No. 60/665,002, filed on Mar. 24, 2005, now abandoned, which are hereby incorporated by reference in their entirety.

STATEMENT REGARDING FEDERALLY SPONSORED RESEARCH OR DEVELOPMENT

The research and development of the invention described below was not federally sponsored.

BACKGROUND OF THE INVENTION

Functional bowel disorders involve abnormal motility and secretion within organs of the gastrointestinal (GI) tract, and are characterized by abdominal discomfort/pain. The criteria for these disorders are summarized by gastroenterologists in the 'Rome II criteria'. Based on these criteria the disorders are common and include, but are not limited to, functional dyspepsia, irritable bowel syndrome (IBS), gastroesophageal reflux disease (GERD) and non-erosive reflux disease (NERD), and chronic constipation (including colonic inertia, idiopathic pseudoobstruction). GERD is extremely prevalent, is usually associated with non-cardiac chest pain and may be treated with acid-suppressing agents and prokinetic agents. IBS is characterized by the presence of reoccurring constipation and/or diarrhea, which can be associated with gaseous distention/bloating and abdominal discomfort/pain (Thompson, W. G. and Heaton, K. W. *Gastroenterology* 1980, 79, 283-288). The onset of the pain of IBS is associated with a change in the frequency and/or form of stool and can be relieved by defecation. IBS is an extremely prevalent condition that occurs to varying severity in 10-15% of the population (Saito, Y. A.; Schoenfeld, P.; and Locke, G. R. *Am. J. Gastroenterol.* 2002, 97, 1910-1915). The pain may be treated with smooth muscle relaxants and antidepressants (Jackson, J. L.; O'Malley, P. G.; Tomkins, G.; Balden, E.; Santoro, J.; and Kroenke, K.; *Am. J. Med.* 2000, 108, 65-72; Jailwala, J.; Imperiale, T. F.; and Kroenke, K.; *Ann. Intern. Med.* 2000, 133:136-147; Akehurst, R. and Kaltenthaler, E. *Gut* 2001, 48, 272-282; Poynard, T.; Regimbeau, C.; and Benhamou, Y.; *Aliment Pharmacol. Ther.* 2001, 15, 355-361). Severe diarrhea predominant IBS is treated by alosetron, whereas constipation predominant IBS is treated by tegaserod. Functional dyspepsia is a disorder of the upper GI tract with symptoms exacerbated by a meal and associated with early satiety, nausea and vomiting. Although its etiology is unknown, prokinetic agents may relieve the symptoms of IBS. In some patients there is overlap in symptoms between GERD/NERD, functional dyspepsia and IBS. Treatments for functional bowel disorders, such as IBS, have low efficacy and are associated with adverse effects. For example, alosetron is approved by the FDA on a risk management program because it is associated with an increase in a serious adverse event, ischemic colitis. No treatments effectively alleviate pain in functional bowel disorders.

In addition to functional disorders, inflammatory bowel diseases (IBD) are common and include ulcerative colitis (UC) and Crohn's disease (CD). Although there may be a genetic component to CD, the etiology of both CD and UC is unknown.

UC is a diffuse mucosal disease of the colon, characterized by inflammation and ulceration, which is associated with diarrhea and abdominal cramping. The mucosal inflammation progresses from the rectal area to eventually extend through the large bowel. CD is a transmural inflammation that most frequently involves the distal small bowel and colon. The inflammation can result in ulcers of varying involvement and in severe cases result in transmural scarring and chronic inflammation. Both infectious and dysregulated immune functions may contribute to disease onset. Therapies for IBD include corticosteroids, immunosuppressives (azathioprine, mercaptopurine, and methotrexate) and aminosalicylates (5-ASA). These therapies involve suppression of the immune system by mimicking corticoids, or unknown mechanisms of action. Oral corticosteroid use is associated with serious adverse effects, whereas immunosuppressives and aminosalicylates are only moderately effective. Infliximab (a chimeric monoclonal anti-tumor necrosis factor antibody) is effective in CD, however, its use is associated with the presence of antibodies, which reduce its efficacy. There are no treatments that target the motility and secretory abnormalities or painful sensation that are associated with gut inflammation.

The cysteine rich proteins known as Prokineticin 1 (PK1) and Prokineticin 2 (PK2), as well as variants, fragments and molecules having PK activity, have been identified. These have been shown to contract gastrointestinal smooth muscle (Li, M.; Bullock, C. M.; Knauer, D. J.; Ehlert, F. J.; and Zhou, Q. Y., *Mol. Pharmacol.* 2001, 59, 692-698), and suppress feeding (Negri, L.; Lattanzi, R.; Giannini, E.; De Felice, M.; Colucci, A. and Melchiorri, P. *Brit. J. Pharmacol.* 2004, 142, 181-191). PK1 and PK2 act on both PK1 and PK2 receptors, and limited structural changes of C-terminal cysteine-rich regions of these related PKs are tolerated. For example, chimeric PKs, where the cysteine-rich domains of PK 1 and PK 2 were exchanged between the two; and a splice variant of PK2 that included a 21 residue insertion in its C-terminal domain retained activity (Bullock, C M; Li J. D.; Zhou, Q. Y.; *Mol. Pharmacol.* 2004, 65(3), 582-8). A PK variant binds to receptors of primary sensory neurons, and results in an intense sensitization of peripheral nociceptors to thermal and mechanical stimuli (Mollay, C.; Weschelberger, C.; Mignogna, G.; Negri, L.; Melchiorri, P.; Barra, D.; Kreil, G.; *Eur. J. Pharmacol.* 1999, 374, 189-196; Negri, L.; Lattanzi, R.; Giannini, E.; Metere, A.; Colucci, M.; Barra, D.; Kreil, G.; Melchiorri, P.; *Brit. J. Pharmacol.* 2002, 137(8), 1147-54).

Patent application PCT/US2004/087054 A2 provides methods of modulating gastric acid or pepsinogen secretion by administering an amount of a prokineticin receptor antagonist effective to alter one or more indicia of gastric acid secretion.

PK1 induces proliferation, migration and fenestration in capillary endothelial cells derived from endocrine glands. The expression of PK mRNA is restricted to the steroidogenic glands, ovary, testis, adrenal and placenta (LeCouter, J.; Kowalski, J.; Foster, J.; Hass, P., Zhang, Z.; Dillard-Telm, L., Frantz, G., Rangell, L.; DeGuzman, L.; Keller, G. A.; Peale, F.; Gurney, A.; Hillan, K. J.; Ferrara, N. *Nature* 2001, 412 (6850), 877-84). In 2002 the identification of the PK1 receptor provided a novel molecular basis for the regulation of angiogenesis in endocrine glands (Masuda, Y.; Takatsu, Y.; Terao, Y.; Kumano, S.; Ishibashi, Y.; Suenaga, M.; Abe, M.; Fukusumi, S.; Watanabe, T.; Shintani, Y.; Yamada, T.; Hinuma, S.; Inatomi, N.; Ohtaki, T.; Onda, H.; Fujino, M.; *Biochem. Biophys. Res. Commun.* 2002, 293(1), 396-402; LeCouter, J.; Lin, R.; Ferrara, N.; *Cold Spring Harb Symp Quant Biol.* 2002, 67, 217-21). For example, adenoviral delivery of PK1 to the mouse testis results in a potent angiogenic response (LeCouter, J.; Lin, R.; Tejada, M.; Frantz, G.; Peale, F.; Hillan, K. J.; Ferrara, N. *Proc. Natl. Acad. Sci. USA.* 2003, 100, 2685-90). Recently, it was shown that PK1 mRNA is not normally expressed in colorectal normal mucosa but is detected in colorectal cancer cells (Goi, T.; Fujioka, M.; Satoh, Y.; Tabata, S.; Koneri, K.; Nagano, H.; Hirono, Y.; Katayama, K.; Hirose, K. and Yamaguchi., Cancer Res. 2004, 64, 1906-1910).

Prokineticin 1 receptor antagonists are useful in the treatment and prevention of various mammalian disease states, for example, visceral pain that is associated with IBS and IBD. Additionally, PK1 receptor antagonists are useful for the treatment of GERD or other forms of secretory diarrhea. Additionally, PK1 receptor antagonists are useful in treating cancer-specific angiogenesis factor in the large intestine and reproductive organs.

It is an object of the present invention to provide prokineticin 1 receptor antagonists. It is also an object of the invention to provide a method of treating or ameliorating a condition mediated by prokineticin 1 receptor. And, it is an object of the invention to provide a useful pharmaceutical composition comprising a compound of the present invention useful as a prokineticin 1 receptor antagonist.

SUMMARY OF THE INVENTION

The present invention is directed to a compound of Formula (I):

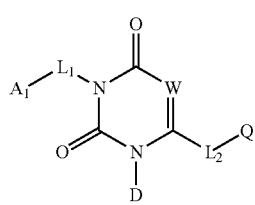

Formula (I)

wherein:
$A_1$ is hydrogen; aryl; heteroaryl; $C_{5-8}$cycloalkyl; or heterocyclyl; provided that $A_1$ is other than piperidin-4-yl, N-t-butoxycarbonyl-piperidin-4-yl, or N-methyl-piperidin-3-yl; and wherein substituents of $A_1$ other than hydrogen are optionally substituted with one to three substituents independently selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, $C_{1-6}$alkylamino, di($C_{1-6}$alkyl)amino, cyano, hydroxy, aminocarbonyl, $C_{1-6}$alkylaminocarbonyl, di($C_{1-6}$alkyl)aminocarbonyl, $C_{1-6}$alkoxycarbonylamino, $C_{1-6}$alkylcarbonyl, $C_{1-6}$alkylthiocarbonyl, formyl, $C_{1-6}$alkylsulfonyl, $C_{1-6}$alkylsulfonylamino, aminosulfonyl, $C_{1-6}$alkylaminosulfonyl, and di($C_{1-6}$alkyl)aminosulfonyl;
$L_1$ is $—(CH_2)_r—$ or $—CH_2CH_2X(CH_2)_s—$, optionally substituted with one to three substituents independently selected from the group consisting of $C_{1-6}$alkyl, $C_{2-6}$alkenyl, $C_{2-6}$alkynyl, and halogen; provided that when $A_1$ is hydrogen, r is greater than or equal to 4;
r is an integer of 1 to 5;
s is an integer of 1 to 3;
X is O or S;
D is $—P-A_2$; wherein when $A_2$ is hydrogen, P is $—(CH_2)_{4-6}—$, and when $A_2$ is other than hydrogen, P is $—(CH_2)_{1-2}—$ or $—CH_2CH=CH—$;
$A_2$ is hydrogen; benzodioxalyl; heteroaryl other than unsubstituted pyridin-2-yl; $C_{3-8}$cycloalkyl; or phenyl optionally substituted at the meta and para positions with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, $C_{1-6}$alkylamino, di($C_{1-6}$alkyl)amino, cyano, hydroxy, nitro, $C_{1-6}$alkylcarbonyl, $C_{1-6}$alkylthiocarbonyl, aminocarbonyl, $C_{1-6}$alkylaminocarbonyl, di($C_{1-6}$alkyl)aminocarbonyl, $C_{1-6}$alkylcarbonylamino, and a non fused $C_{3-6}$cycloalkyloxy; wherein benzodioxalyl, heteroaryl, and $C_{3-8}$cycloalkyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, $C_{1-6}$alkylamino, di($C_{1-6}$alkyl)amino, cyano, hydroxy, nitro, $C_{1-6}$alkylcarbonyl, $C_{1-6}$alkylthiocarbonyl, aminocarbonyl, $C_{1-6}$alkylaminocarbonyl, di($C_{1-6}$alkyl)aminocarbonyl, $C_{1-6}$alkylcarbonylamino, and a non fused $C_{3-6}$cycloalkyloxy;
provided that no more than two substituents on $A_2$ are aryl($C_{1-6}$)alkoxy, phenyl, or a non fused $C_{3-6}$cycloalkyloxy;
provided that when $A_1$ is unsubstituted phenyl and $L_2$ is $—X_1—CH(R^x)—(CR^yR^z)—$ wherein $X_1$ is NH, and $R^x$, $R^y$, and $R^z$ are each hydrogen, $A_2$ is other than unsubstituted phenyl; phenyl substituted with aryl($C_{1-6}$)alkoxy or phenyl; or phenyl substituted at the meta position with cyano;
and, further provided that when $A_1$ is unsubstituted phenyl and $L_2$ is $—X_1—CH(R^x)—(CR^yR^z)_2—$ wherein $X_1$ is NH and $R^x$, $R^y$, and $R^z$ are each hydrogen, $A_2$ is other than phenyl substituted with methoxy;
and, provided that when $A_1$ is 3,4-dichloro-phenyl and P is $—CH_2—$, $A_2$ is other than phenyl substituted at the meta position with trifluoromethyl or trifluoromethoxy;
and, further provided that when $A_1$ is 3,4-dichloro-phenyl and P is $—(CH_2)_2—$, $A_2$ is other than 4-methoxy-phenyl;
W is N or $C(R_w)$; wherein $R_w$ is H or $C_{1-2}$alkyl;
$L_2$ is a bivalent radical selected from the group consisting of pyrrolidinyl or piperidinyl attached to the triazine ring of Formula (I) via its nitrogen atom, wherein said pyrrolidinyl or piperidinyl is substituted on a carbon atom with $—(CH_2)_{0-2}—$;
$—NH—C_{6-7}$cycloalkyl-$(CH_2)_{0-2}—$; such that when $C_{5-7}$cycloalkyl is cyclohexyl, Q is attached at either the 2- or cis-4-position relative to the position of $—NH—$;
$—X_1—(CH_2)_u—X_2—(CH_2)_v—$; wherein u is an integer of 1 to 3; and wherein v is an integer of 1 to 4; provided that when $X_1$ is a direct bond and W is $C(R_w)$, then u is 1 and v is 2 to 4;
$—X_2—(CH_2)_{0-4}—$;
$—X_1—(CH_2)_{2-3}—X—(CH_2)_{2-3}—$;
$—NH(CH_2)_{1-4}C(=O)—$, provided that at least one of $R^b$, $R^c$, or $R^d$ is other than hydrogen and m is 0;
$—NHC(=O)—(CH_2)_{1-4}—$;
$—C(=O)NH(CR^yR^z)_{2-5}—$;
and
$—X_1—CH(R^x)—(CR^yR^z)_{1-5}—$; such that when $X_1$ is a direct bond and W is $C(R_w)$, then $R^x$ is hydrogen;
wherein $X_1$ is $—NH—$, O, S, or a direct bond, such that $X_1$ is other than O when W is N;
$X_2$ is $—CH=CH—$;
$X_3$ is O, S, NH, or C=O;
$R^x$, $R^y$, and $R^z$ are independently H or $C_{1-4}$alkyl;
and provided that $L_2$ in any instance does not exceed 7 atoms in length;
and further provided that when $L_2$ is $—X_2—(CH_2)_{0-4}—$ or $—C(=O)NH(CR^yR^z)_{2-5}—$, then $R_w$ is hydrogen;

Q is —(O)$_m$N(R$^a$)-G; and m is 0 or 1;

G is —C(=NR$^b$)NR$^c$R$^d$;

R$^a$ and R$^d$ are independently hydrogen, C$_{1-6}$alkyl, C$_{2-6}$alkenyl, or C$_{3-6}$alkynyl, wherein substituents of R$^a$ and R$^d$ other than hydrogen are optionally substituted with one to three substituents independently selected from the group consisting of hydroxy, C$_{1-4}$alkoxy, fluoro, amino, C$_{1-4}$alkylamino, diC$_{1-4}$alkylamino, and C$_{1-4}$alkylcarbonyl; or R$^a$ and R$^c$ are taken together with the atoms to which they are attached to form a 5-8 membered monocyclic ring optionally substituted with oxo;

R$^b$ is hydrogen, C$_{1-6}$alkyl, C$_{2-6}$alkenyl, C$_{3-6}$alkynyl, C$_{2-6}$alkoxycarbonyl, or cyano; or, R$^b$ and R$^c$ are taken together with the atoms to which they are attached to form a 5-8 membered monocyclic ring optionally substituted with oxo;

R$^c$ is hydrogen, C$_{1-10}$alkyl, C$_{2-10}$alkenyl, C$_{3-10}$alkynyl, C$_{3-7}$cycloalkyl, adamantyl, amino, C$_{1-6}$alkylamino, di(C$_{1-6}$alkyl)amino, C$_{1-6}$alkylcarbonyl, C$_{1-6}$alkoxycarbonyl, arylcarbonyl, heteroarylcarbonyl, heterocyclylcarbonyl, aryl, heteroaryl, or heterocyclyl; wherein C$_{1-10}$alkyl, C$_{2-10}$alkenyl, and C$_{2-10}$alkynyl are optionally substituted with one to three substituents independently selected from the group consisting of hydroxy, C$_{1-6}$alkoxy, trifluoromethyl, aryl, heteroaryl, and heterocyclyl; and wherein any aryl- or heteroaryl-containing substituents of R$^c$ are optionally substituted with one to three substituents independently selected from the group consisting of C$_{1-6}$alkyl, C$_{1-6}$alkoxy, halogen, fluorinated C$_{1-6}$alkyl, fluorinated C$_{1-6}$alkoxy, C$_{1-6}$alkylcarbonyl, C$_{1-6}$alkoxycarbonyl, aminocarbonyl, C$_{1-6}$alkylaminocarbonyl, di(C$_{1-6}$alkyl)aminocarbonyl, C$_{1-6}$alkoxycarbonylamino, formyl, C$_{1-6}$alkylsulfonylamino, aminosulfonyl, C$_{1-6}$alkylaminosulfonyl, and di(C$_{1-6}$alkyl)aminosulfonyl, nitro, methylthio, hydroxy, and cyano; or, R$^b$ and R$^d$ are taken together with the atoms to which they are attached to form a 5-8 membered monocyclic ring that optionally includes 1 to 2 O or S heteroatoms within the ring, and said ring is optionally substituted with oxo;

with the proviso that in any instance, only one ring optionally exists between R$^a$ and R$^b$, R$^b$ and R$^c$, or R$^b$ and R$^d$;

and enantiomers, diastereomers, tautomers, solvates, and pharmaceutically acceptable salts thereof.

DETAILED DESCRIPTION OF THE INVENTION

Figure 1:
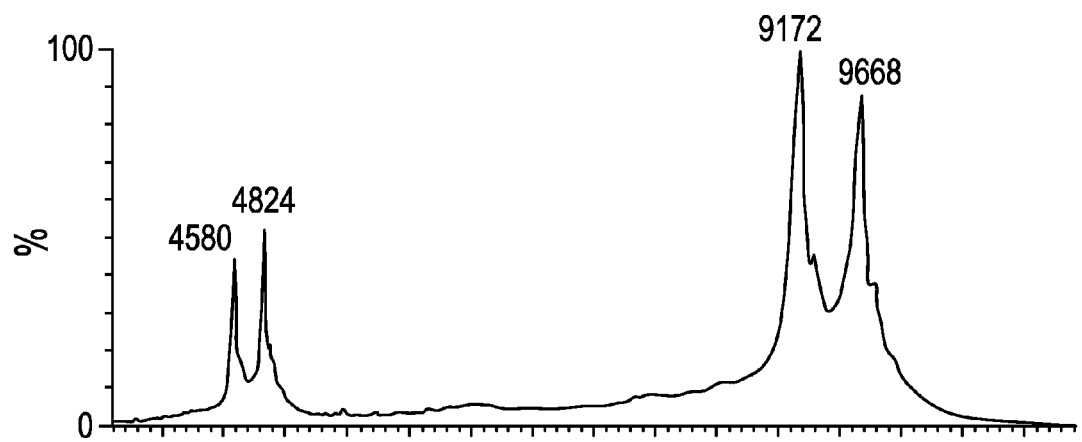
FIG. 1 shows a MALDI-TOF ANALYSIS of a Prokineticin-1 ligand preparation mixture. The mixture includes a four C-terminal residue truncated product (MW=9172), and a full-length prokineticin-1 ligand (MW=9668).

As used herein, the following terms are intended to have the following meanings:

"C$_{a-b}$" (where a and b are integers) refers to a radical containing from a to b carbon atoms inclusive. For example, C$_{1-3}$ denotes a radical containing 1, 2 or 3 carbon atoms.

With reference to substituents, the term "independently" means that when more than one of such substituent is possible, such substituents may be the same or different from each other. Therefore, designated numbers of carbon atoms (e.g. C$_{1-8}$) shall refer independently to the number of carbon atoms in an alkyl or cycloalkyl moiety or to the alkyl portion of a larger substituent in which alkyl appears as its prefix root.

As used herein, unless otherwise noted, "alkyl" whether used alone or as part of a substituent group refers to straight and branched carbon chains having 1 to 8 carbon atoms or any number within this range. The term "alkoxy" refers to an —Oalkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a carbon atom. In substituent groups with multiple alkyl groups such as (C$_{1-6}$alkyl)$_2$amino- the C$_{1-6}$alkyl groups of the dialkylamino may be the same or different.

"Halogenated alkyl" refers to a saturated branched or straight chain alkyl radical derived by removal of 1 hydrogen atom from the parent alkyl; the parent alkyl chain contains from 1 to 8 carbon atoms with 1 or more hydrogen atoms substituted with halogen atoms up to and including substitution of all hydrogen atoms with halogen. Preferred halogenated alkyl groups include include trifluoromethyl substituted alkyls and perfluorinated alkyls; more preferred fluorinated alkyls include trifluoromethyl.

"Halogenated alkoxy" refers to a radical derived from a halogenated alkyl, radical attached to an oxygen atom with the oxygen atom having one open valence for attachment to a parent structure.

The term "cycloalkyl" refers to saturated or partially unsaturated, moncyclic or polycyclic hydrocarbon rings of from 3 to 20 carbon atom members (preferably from 3 to 14 carbon atom members). Examples of such rings include, and are not limited to, cyclopropyl, cyclobutyl, cyclopentyl, cyclohexyl, cycloheptyl or adamantyl. The term cycloalkyl includes a cycloalkyl ring fused to a benzene ring (benzo fused cycloalkyl), a 5 or 6 membered heteroaryl ring (containing one of O, S or N and, optionally, one additional nitrogen) to form a heteroaryl fused cycloalkyl.

The term "heterocyclyl" refers to a nonaromatic cyclic ring of 5 to 10 members in which 1 to 4 members are nitrogen or a nonaromatic cyclic ring of 5 to 10 members in which zero, one or two members are nitrogen and up to two members is oxygen or sulfur; wherein, optionally, the ring contains zero, one or two unsaturated bonds. The term heterocyclyl includes a heterocyclyl ring fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For instant compounds of the invention, the carbon atom ring members that form the heterocyclyl ring are fully saturated. Other compounds of the invention may have a partially saturated heterocyclyl ring. Additionally, heterocyclyl includes a heterocyclic ring bridged to form bicyclic rings. Preferred partially saturated heterocyclyl rings may have from one to two double bonds.

Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. The term heteroaryl includes a heteroaryl ring fused to a benzene ring (benzo fused heteroaryl), a 5 or 6 membered heteroaryl ring (containing one of O, S or N and, optionally, one additional nitrogen), a 5 to 7 membered cycloalkyl ring or a 5 to 7 membered heterocyclic ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

The term "halogen" refers to fluorine, chlorine, bromine and iodine. Substituents that are substituted with multiple halogens are substituted in a manner that provides compounds, which are stable.

The term "oxo" whether used alone or as part of a substituent group refers to an O= to either a carbon or a sulfur atom. For example, phthalimide and saccharin are examples of compounds with oxo substituents.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "acyl" refers to alkylcarbonyl substituents.

Throughout this disclosure, the terminal portion of the designated side chain is described first, followed by the adjacent functionality toward the point of attachment. Thus, for example, a "phenyl($C_{1-6}$)alkylaminocarbonyl($C_{1-6}$)alkyl" substituent refers to a group of the formula

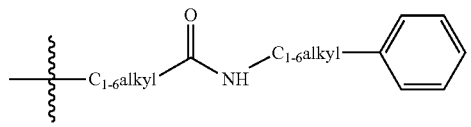

The present invention is directed to a compound of Formula (I):

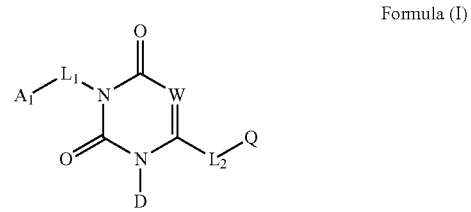

Formula (I)

wherein:
$A_1$ is hydrogen; aryl; heteroaryl; $C_{5-8}$cycloalkyl; or heterocyclyl; provided that $A_1$ is other than piperidin-4-yl, N-t-butoxycarbonyl-piperidin-4-yl, or N-methyl-piperidin-3-yl; and wherein substituents of $A_1$ other than hydrogen are optionally substituted with one to three substituents independently selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, $C_{1-6}$alkylamino, di($C_{1-6}$alkyl)amino, cyano, hydroxy, aminocarbonyl, $C_{1-6}$alkylaminocarbonyl, di($C_{1-6}$alkyl)aminocarbonyl, $C_{1-6}$alkoxycarbonylamino, $C_{1-6}$alkylcarbonyl, $C_{1-6}$alkylthiocarbonyl, formyl, $C_{1-6}$alkylsulfonyl, $C_{1-6}$alkylsulfonylamino, aminosulfonyl, $C_{1-6}$alkylaminosulfonyl, and di($C_{1-6}$alkyl)aminosulfonyl;

$L_1$ is —$(CH_2)_r$— or —$CH_2CH_2X(CH_2)_s$—, optionally substituted with one to three substituents independently selected from the group consisting of $C_{1-6}$alkyl, $C_{2-6}$alkenyl, $C_{2-6}$alkynyl, and halogen; provided that when $A_1$ is hydrogen, r is greater than or equal to 4;

r is an integer of 1 to 5;
s is an integer of 1 to 3;
X is O or S;
D is —P-$A_2$; wherein when $A_2$ is hydrogen, P is —$(CH_2)_{4-6}$—, and when $A_2$ is other than hydrogen, P is —$(CH_2)_{1-2}$— or —$CH_2CH=CH$—;

A$_2$ is hydrogen; benzodioxalyl; heteroaryl other than unsubstituted pyridin-2-yl; C$_{3-8}$cycloalkyl; or phenyl optionally substituted at the meta and para positions with one to three substituents independently selected from the group consisting of C$_{1-6}$alkyl, C$_{1-6}$alkoxy, halogen, halogenated C$_{1-6}$alkyl, halogenated C$_{1-6}$alkoxy, aryl(C$_{1-6}$)alkoxy, phenyl, C$_{1-6}$alkylthio, C$_{1-6}$alkoxycarbonyl, amino, C$_{1-6}$alkylamino, di(C$_{1-6}$)alkyl)amino, cyano, hydroxy, nitro, C$_{1-6}$alkylcarbonyl, C$_{1-6}$alkylthiocarbonyl, aminocarbonyl, C$_{1-6}$alkylaminocarbonyl, di(C$_{1-6}$alkyl)aminocarbonyl, C$_{1-6}$alkylcarbonylamino, and a non fused C$_{3-6}$cycloalkyloxy; wherein benzodioxalyl, heteroaryl, and C$_{3-8}$cycloalkyl are optionally substituted with one to three substituents independently selected from the group consisting of C$_{1-6}$alkyl, C$_{1-6}$alkoxy, halogen, halogenated C$_{1-6}$alkyl, halogenated C$_{1-6}$alkoxy, aryl(C$_{1-6}$)alkoxy, phenyl, C$_{1-6}$alkylthio, C$_{1-6}$alkoxycarbonyl, amino, C$_{1-6}$alkylamino, di(C$_{1-6}$alkyl)amino, cyano, hydroxy, nitro, C$_{1-6}$alkylcarbonyl, C$_{1-6}$alkylthiocarbonyl, aminocarbonyl, C$_{1-6}$alkylaminocarbonyl, di(C$_{1-6}$alkyl)aminocarbonyl, C$_{1-6}$alkylcarbonylamino, and a non fused C$_{3-6}$cycloalkyloxy;

provided that no more than two substituents on A$_2$ are aryl(C$_{1-6}$)alkoxy, phenyl, or a non fused C$_{3-6}$cycloalkyloxy;

provided that when A$_1$ is unsubstituted phenyl and L$_2$ is —X$_1$—CH(R$^x$)—(CR$^y$R$^z$)— wherein X$_1$ is NH, and R$^x$, R$^y$, and R$^z$ are each hydrogen, A$_2$ is other than unsubstituted phenyl; phenyl substituted with aryl(C$_{1-6}$)alkoxy or phenyl; or phenyl substituted at the meta position with cyano;

and, further provided that when A$_1$ is unsubstituted phenyl and L$_2$ is —X$_1$—CH(R$^x$)—(CR$^y$R$^z$)$_2$— wherein X$_1$ is NH and R$^x$, R$^y$, and R$^z$ are each hydrogen, A$_2$ is other than phenyl substituted with methoxy;

and, provided that when A$_1$ is 3,4-dichloro-phenyl and P is —CH$_2$—, A$_2$ is other than phenyl substituted at the meta position with trifluoromethyl or trifluoromethoxy;

and, further provided that when A$_1$ is 3,4-dichloro-phenyl and P is —(CH$_2$)$_2$—, A$_2$ is other than 4-methoxy-phenyl;

W is N or C(R$_W$); wherein R$_W$ is H or C$_{1-2}$alkyl;

L$_2$ is a bivalent radical selected from the group consisting of pyrrolidinyl or piperidinyl attached to the triazine ring of Formula (I) via its nitrogen atom, wherein said pyrrolidinyl or piperidinyl is substituted on a carbon atom with —(CH$_2$)$_{0-2}$—;
—NH—C$_{5-7}$cycloalkyl-(CH$_2$)$_{0-2}$—; such that when C$_{5-7}$cycloalkyl is cyclohexyl, Q is attached at either the 2- or cis-4-position relative to the position of —NH—;
—X$_1$—(CH$_2$)$_u$—X$_2$—(CH$_2$)$_v$—; wherein u is an integer of 1 to 3; and wherein v is an integer of 1 to 4; provided that when X$_1$ is a direct bond and W is C(R$_w$), then u is 1 and v is 2 to 4;
—X$_2$—(CH$_2$)$_{0-4}$—;
—X$_1$—(CH$_2$)$_{2-3}$—X$_3$—(CH$_2$)$_{2-3}$—;
—NH(CH$_2$)$_{1-4}$C(=O)—, provided that at least one of R$^b$, R$^c$, or R$^d$ is other than hydrogen and m is 0;
—NHC(=O)—(CH$_2$)$_{1-4}$—;
—C(=O)NH(CR$^y$R$^z$)$_{2-5}$—;
and
—X$_1$—CH(R$^x$)—(CR$^y$R$^z$)$_{1-5}$—; such that when X$_1$ is a direct bond and W is C(R$_w$), then R$^x$ is hydrogen;
wherein X$_1$ is —NH—, O, S, or a direct bond, such that X$_1$ is other than O when W is N;
X$_2$ is —CH=CH—;
X$_3$ is O, S, NH, or C=O;
R$^x$, R$^y$, and R$^z$ are independently H or C$_{1-4}$alkyl;

and provided that L$_2$ in any instance does not exceed 7 atoms in length; and further provided that when L$_2$ is —X$_2$—(CH$_2$)$_{0-4}$— or —C(=O)NH(CR$^y$R$^z$)$_{2-5}$—, then R$_W$ is hydrogen;

Q is —(O)$_m$N(R$^a$)-G; and m is 0 or 1;

G is —C(=NR$^b$)NR$^c$R$^d$;

R$^a$ and R$^d$ are independently hydrogen, C$_{1-6}$alkyl, C$_{2-6}$alkenyl, or C$_{3-6}$alkynyl, wherein substituents of R$^a$ and R$^d$ other than hydrogen are optionally substituted with one to three substituents independently selected from the group consisting of hydroxy, C$_{1-4}$alkoxy, fluoro, amino, C$_{1-4}$alkylamino, diC$_{1-4}$alkylamino, and C$_{1-4}$alkylcarbonyl; or R$^a$ and R$^c$ are taken together with the atoms to which they are attached to form a 5-8 membered monocyclic ring optionally substituted with oxo;

R$^b$ is hydrogen, C$_{1-6}$alkyl, C$_{2-6}$alkenyl, C$_{3-6}$alkynyl, C$_{2-6}$alkoxycarbonyl, or cyano; or, R$^b$ and R$^c$ are taken together with the atoms to which they are attached to form a 5-8 membered monocyclic ring optionally substituted with oxo;

R$^c$ is hydrogen, C$_{1-10}$alkyl, C$_{2-10}$alkenyl, C$_{3-10}$alkynyl, C$_{3-7}$cycloalkyl, adamantyl, amino, C$_{1-6}$alkylamino, di(C$_{1-6}$alkyl)amino, C$_{1-6}$alkylcarbonyl, C$_{1-6}$alkoxycarbonyl, arylcarbonyl, heteroarylcarbonyl, heterocyclylcarbonyl, aryl, heteroaryl, or heterocyclyl; wherein C$_{1-10}$alkyl, C$_{2-10}$alkenyl, and C$_{2-10}$alkynyl are optionally substituted with one to three substituents independently selected from the group consisting of hydroxy, C$_{1-6}$alkoxy, trifluoromethyl, aryl, heteroaryl, and heterocyclyl; and wherein any aryl- or heteroaryl-containing substituents of R$^c$ are optionally substituted with one to three substituents independently selected from the group consisting of C$_{1-6}$alkyl, C$_{1-6}$alkoxy, halogen, fluorinated C$_{1-6}$alkyl, fluorinated C$_{1-6}$alkoxy, C$_{1-6}$alkylcarbonyl, C$_{1-6}$alkoxycarbonyl, aminocarbonyl, C$_{1-6}$alkylaminocarbonyl, di(C$_{1-6}$alkyl)aminocarbonyl, C$_{1-6}$alkoxycarbonylamino, formyl, C$_{1-6}$alkylsulfonyl, C$_{1-6}$alkylsulfonylamino, aminosulfonyl, C$_{1-6}$alkylaminosulfonyl, and di(C$_{1-6}$alkyl)aminosulfonyl, nitro, methylthio, hydroxy, and cyano; or, R$^c$ and R$^d$ are taken together with the atoms to which they are attached to form a 5-8 membered monocyclic ring that optionally includes 1 to 2 O or S heteroatoms within the ring, and said ring is optionally substituted with oxo;

with the proviso that in any instance, only one ring optionally exists between R$^a$ and R$^b$, R$^b$ and R$^c$, or R$^c$ and R$^d$;

and further provided that a compound of Formula (I) is other than a compound wherein A$_1$ is phenyl, L is —CH$_2$—, D is —CH$_2$-(4-methoxy-phenyl), W is N, L$_2$ is —NH(CH$_2$)$_2$—, and Q is —NHC(=NH)NH$_2$.

and enantiomers, diastereomers, tautomers, solvates, and pharmaceutically acceptable salts thereof.

Embodiments of the present invention include compounds of Formula (I) wherein:

a) A$_1$ is hydrogen; aryl; heteroaryl; or C$_{5-8}$cycloalkyl; wherein substituents of A$_1$ other than hydrogen are optionally substituted with one to three substituents independently selected from the group consisting of C$_{1-6}$alkyl, hydroxy(C$_{1-6}$)alkyl, C$_{1-6}$alkoxy, halogen, nitro, halogenated C$_{1-6}$alkyl, halogenated C$_{1-6}$alkoxy, C$_{1-6}$alkylthio, C$_{1-6}$alkoxycarbonyl, amino, C$_{1-6}$alkylamino, di(C$_{1-6}$alkyl)amino, cyano, hydroxy, aminocarbonyl, C$_{1-6}$alkylaminocarbonyl, di(C$_{1-6}$alkyl)aminocarbonyl, C$_{1-6}$alkoxycarbonylamino, C$_{1-6}$alkylcarbonyl, C$_{1-6}$alkylthiocarbonyl, formyl, C$_{1-6}$alkylsulfonyl, C$_{1-6}$alkylsulfonylamino, aminosulfonyl, C$_{1-6}$alkylaminosulfonyl, and di(C$_{1-6}$alkyl)aminosulfonyl;

b) $A_1$ is hydrogen; aryl; heteroaryl; $C_{5-8}$cycloalkyl; or heterocyclyl; provided that $A_1$ is other than piperidin-4-yl, N-t-butoxycarbonyl-piperidin-4-yl, or N-methyl-piperidin-3-yl; and wherein substituents of $A_1$ other than hydrogen are optionally substituted with one to three substituents independently selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, cyano, hydroxy, aminocarbonyl, $C_{1-6}$alkylaminocarbonyl, di($C_{1-6}$alkyl)aminocarbonyl, and $C_{1-6}$alkylcarbonyl;

c) $A_1$ is hydrogen; aryl; heteroaryl; $C_{5-8}$cycloalkyl; or heterocyclyl other than piperidinyl; wherein substituents of $A_1$ other than hydrogen are optionally substituted with one to three substituents independently selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, cyano, hydroxy, aminocarbonyl, $C_{1-6}$alkylaminocarbonyl, di($C_{1-6}$alkyl)aminocarbonyl, and $C_{1-6}$alkylcarbonyl;

d) $A_1$ is hydrogen, substituted phenyl, benzofuranyl, furanyl, thiazolyl, thiophenyl, or cyclopentyl; wherein substituents of $A_1$ other than hydrogen are optionally substituted and phenyl is substituted with one to two substituents independently selected from the group consisting of $C_{1-4}$alkyl, $C_{1-4}$alkoxy, halogen, nitro, halogenated $C_{1-4}$alkyl, halogenated $C_{1-4}$alkoxy, methylthio, $C_{1-4}$alkoxycarbonyl, amino, cyano, hydroxy, aminocarbonyl, and $C_{1-4}$alkylcarbonyl;

e) $A_1$ is substituted phenyl, benzofuranyl, thiazolyl, or thiophenyl; wherein phenyl is substituted with, and benzofuranyl, thiazolyl, and thiophenyl are optionally substituted with one to two substituents independently selected from the group consisting of $C_{1-4}$alkyl, $C_{1-4}$alkoxy, halogen, nitro, halogenated $C_{1-4}$alkyl, halogenated $C_{1-4}$alkoxy, methylthio, amino, cyano, and $C_{1-4}$alkylcarbonyl;

f) $A_1$ is phenyl or benzofuranyl; wherein phenyl is substituted at either the para-position or meta and para-positions with one to two substituents independently selected from the group consisting of ethyl, methoxy, fluoro, chloro, nitro, difluoromethoxy, and methylthio;

g) $L_1$ is —$(CH_2)_r$—, optionally substituted with one to three substituents independently selected from the group consisting of $C_{1-6}$alkyl, $C_{2-6}$alkenyl, $C_{2-6}$alkynyl, and halogen; provided that when $A_1$ is hydrogen, r is greater than or equal to 4;

h) $L_1$ is —$(CH_2)_r$—, optionally substituted with a substituent selected from the group consisting of $C_{1-4}$alkyl, $C_{2-4}$alkenyl, and $C_{2-4}$alkynyl, provided that r is 1 to 3 when $A_1$ is other than hydrogen; or r is greater than or equal to 4 when $A_1$ is hydrogen;

i) $L_1$ is —$(CH_2)_r$— optionally substituted with a substituent selected from the group consisting of methyl and allyl, provided that r is 1 to 3 when $A_1$ is other than hydrogen;

j) $L_1$ is —$CH_2$— optionally substituted with methyl or allyl;

k) P is —$CH_2$— l) $A_2$ is hydrogen, heteroaryl other than unsubstituted pyridin-2-yl, $C_{3-8}$cycloalkyl, or phenyl optionally substituted at the meta and para positions with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, cyano, hydroxy, nitro, aminocarbonyl, $C_{1-6}$alkylcarbonylamino, and a non fused $C_{3-6}$cycloalkyloxy; wherein heteroaryl other than unsubstituted pyridin-2-yl and $C_{3-8}$cycloalkyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, cyano, hydroxy, nitro, aminocarbonyl, $C_{1-6}$alkylcarbonylamino, and a non fused $C_{3-6}$cycloalkyloxy;
provided that no more than two substituents on $A_2$ are aryl($C_{1-6}$)alkoxy, phenyl, or a non fused $C_{3-6}$cycloalkyloxy;
provided that when $A_1$ is unsubstituted phenyl and $L_2$ is —$X_1$—$CH(R^x)$—$(CR^yR^z)$— wherein $X_1$ is NH and $R^x$, $R^y$, and $R^z$ are each hydrogen, $A_2$ is other than unsubstituted phenyl; phenyl substituted with aryl($C_{1-6}$)alkoxy or phenyl; or phenyl substituted at the meta position with cyano;
and, further provided that when $A_1$ is unsubstituted phenyl and $L_2$ is —$X_1$—$CH(R^x)$—$(CR^yR^z)_2$— wherein $X_1$ is NH and $R^x$, $R^y$, and $R^z$ are each hydrogen, $A_2$ is other than phenyl substituted with methoxy;
and, provided that when $A_1$ is 3,4-dichloro-phenyl and P is —$CH_2$—, $A_2$ is other than phenyl substituted at the meta position with trifluoromethyl or trifluoromethoxy;
and, further provided that when $A_1$ is 3,4-dichloro-phenyl and P is —$(CH_2)_2$—, $A_2$ is other than 4-methoxy-phenyl;
in addition, when $A_2$ is hydrogen, P is —$(CH_2)_{4-6}$—, and when $A_2$ is other than hydrogen, P is —$(CH_2)_{1-2}$— or —$CH_2CH=CH$—;

m) $A_2$ is heteroaryl other than unsubstituted pyridin-2-yl, a non fused $C_{3-8}$cycloalkyl, or phenyl optionally substituted at the meta and para positions with one to three substituents independently selected from the group consisting of $C_{1-6}$alkyl, $C_{1-6}$alkoxy, halogen, halogenated $C_{1-6}$alkyl, halogenated $C_{1-6}$alkoxy, $C_{1-6}$alkylthio, $C_{1-6}$alkoxycarbonyl, amino, hydroxy, nitro, aminocarbonyl, $C_{1-6}$alkylcarbonylamino, and a non fused $C_{3-6}$cycloalkyloxy; wherein heteroaryl other than unsubstituted pyridin-2-yl and a non fused $C_{3-8}$cycloalkyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, $C_{1-6}$alkylthio, $C_{1-6}$alkoxycarbonyl, amino, hydroxy, nitro, aminocarbonyl, $C_{1-6}$alkylcarbonylamino, and a non fused $C_{3-6}$cycloalkyloxy; provided that no more than two substituents on $A_2$ are non fused $C_{3-6}$cycloalkyloxy;
provided that when $A_1$ is unsubstituted phenyl and $L_2$ is —$X_1$—$CH(R^x)$—$(CR^yR^z)$— wherein $X_1$ is NH and $R^x$, $R^y$, and $R^z$ are each hydrogen, $A_2$ is other than unsubstituted phenyl;
and, further provided that when $A_1$ is unsubstituted phenyl and $L_2$ is —$X_1$—$CH(R^x)$—$(CR^yR^z)_2$— wherein $X_1$ is NH and $R^x$, $R^y$, and $R^z$ are each hydrogen, $A_2$ is other than phenyl substituted with methoxy;
and, provided that when $A_1$ is 3,4-dichloro-phenyl, $A_2$ is other than phenyl substituted at the meta position with trifluoromethyl or trifluoromethoxy;
and, further provided that when $A_1$ is 3,4-dichloro-phenyl and P is —$(CH_2)_2$—, $A_2$ is other than 4-methoxy-phenyl;

n) $A_2$ is furanyl, pyridin-3-yl, pyridin-4-yl, or phenyl optionally substituted at the meta and para positions with one to three substituents independently selected from the group consisting of $C_{1-4}$alkyl, $C_{1-4}$alkoxy, halogen, halogenated $C_{1-3}$alkoxy, $C_{1-3}$alkylthio, hydroxy, amino, aminocarbonyl, $C_{1-3}$alkylcarbonylamino, and a non fused $C_{3-6}$cycloalkyloxy; and wherein furanyl, pyridin-3-yl, and pyridin-4-yl are optionally substituted with one to three substituents independently selected from the group consisting of $C_{1-4}$alkyl, $C_{1-4}$alkoxy, halogen, halogenated $C_{1-3}$alkoxy, $C_{1-3}$alkylthio, hydroxy, amino, aminocarbonyl, $C_{1-3}$alkylcarbonylamino, and a non fused $C_{3-6}$cycloalkyloxy;
  provided that no more than two substituents on $A_2$ are non fused $C_{3-6}$cycloalkyloxy;
  provided that when $A_1$ is unsubstituted phenyl and $L_2$ is —$X_1$—CH($R^x$)—(C$R^yR^z$)— wherein $X_1$ is NH and $R^x$, $R^y$, and $R^z$ are each hydrogen, $A_2$ is other than unsubstituted phenyl;
  and, further provided that when $A_1$ is unsubstituted phenyl and $L_2$ is —$X_1$—CH($R^x$)—(C$R^yR^z$)$_2$— wherein $X_1$ is NH and $R^x$, $R^y$, and $R^z$ are each hydrogen, $A_2$ is other than phenyl substituted with methoxy;
  and, provided that when $A_1$ is 3,4-dichloro-phenyl, $A_2$ is other than phenyl substituted in the meta position with trifluoromethoxy;
o) $A_2$ is pyridin-3-yl pyridin-4-yl, or phenyl optionally substituted at the meta and para positions with one to two substituents independently selected from the group consisting of methyl, ethyl, methoxy, ethoxy, isopropyloxy, trifluoromethoxy, difluoromethoxy, hydroxy, aminocarbonyl, and methylcarbonylamino; wherein pyridin-3-yl and pyridin-4-yl are optionally substituted with one to two substituents independently selected from the group consisting of methyl, ethyl, methoxy, ethoxy, isopropyloxy, trifluoromethoxy, difluoromethoxy, hydroxy, aminocarbonyl, and methylcarbonylamino;
  provided that when $A_1$ is unsubstituted phenyl and $L_2$ is —$X_1$—CH($R^x$)—(C$R^yR^z$)— wherein $X_1$ is NH and $R^x$, $R^y$, and $R^z$ are each hydrogen, $A_2$ is other than unsubstituted phenyl;
  and, further provided that when $A_1$ is unsubstituted phenyl and $L_2$ is —$X_1$—CH($R^x$)—(C$R^yR^z$)$_2$— wherein $X_1$ is NH and $R^x$, $R^y$, and $R^z$ are each hydrogen, $A_2$ is other than phenyl substituted with methoxy;
  and, provided that when $A_1$ is 3,4-dichloro-phenyl, $A_2$ is other than phenyl substituted in the meta position with trifluoromethoxy;
p) $A_2$ is phenyl substituted at the para position with a substituent selected from the group consisting of methoxy, ethoxy, isopropyloxy, difluoromethoxy, hydroxy, and aminocarbonyl; or $A_2$ is pyridin-3-yl or pyridin-4-yl substituted with methoxy;
q) W is N or C($R_w$) wherein $R_w$ is H;
r) $L_2$ is a bivalent radical selected from the group consisting of
  —NH—$C_{5-7}$cycloalkyl-(CF$_2$)$_{0-2}$—; provided that when $C_{5-7}$cycloalkyl is cyclohexyl, Q is attached at either the 2- or cis-4-position relative to the position of —NH—;
  —$X_2$—(CH$_2$)$_{0-4}$—;
  —$X_1$—(CH$_2$)$_{2-3}$—$X_3$—(CH$_2$)$_{2-3}$—;
  —NH(CH$_2$)$_{1-4}$C(=O)— provided that at least one of $R^b$, $R^c$, or $R^d$ is other than hydrogen and m is 0;
  —NHC(=O)—(CH$_2$)$_{1-4}$—;
  —C(=O)NH(C$R^yR^z$)$_{2-5}$—;
  and
  —$X_1$—CH($R^x$)—(C$R^yR^z$)$_{1-5}$—; such that when $X_1$ is a direct bond and W is C($R_w$), then $R^x$ of CH($R^x$) is hydrogen;
  wherein $X_1$ is —NH—, O, S, or a direct bond; such that $X_1$ is other than O when W is N;
  $X_2$ is —CH=CH—;
  $X_3$ is O, S, NH, or C=O;
  $R^x$, $R^y$, and $R^z$ are independently H or $C_{1-4}$alkyl;
  and provided that $L_2$ in any instance does not exceed 7 atoms in length; and
  further provided that when $L_2$ is —$X_2$—(CH$_2$)$_{0-4}$— or —C(=O)NH(C$R^yR^z$)$_{2-5}$—, then $R_w$ is hydrogen;
s) $L_2$ is a bivalent radical selected from the group consisting of
  —NH—$C_{5-6}$cycloalkyl-(CH$_2$)$_{0-2}$—; provided that when $C_{5-6}$cycloalkyl is cyclohexyl, Q is attached at either the 2- or cis-4-position relative to the position of —NH—;
  —$X_1$—CH($R^x$)—(C$R^yR^z$)$_{1-5}$—, wherein $X_1$ is —NH—, O, or S and $R^x$, $R^y$, and $R^z$ are each hydrogen; such that $X_1$ is other than O when W is N;
  —C(=O)NH(CH$_2$)$_2$—;
  and
  —$X_1$—(R,R—CH($R^x$)C$R^y$($R^z$))—; wherein $X_1$ is —NH—, and $R^x$ and $R^z$ are methyl, and $R^y$ is hydrogen;
  provided that when $L_2$ is —C(=O)NH(CH$_2$)$_2$—, then $R_w$ is hydrogen;
t) $L_2$ is a bivalent radical selected from the group consisting of
  —NH-cyclohexyl-(CH$_2$)$_{0-2}$— and Q is attached at either the 2- or cis-4-position relative to the position of —NH—;
  —$X_1$—CH($R^x$)—(C$R^yR^z$)$_{1-5}$—; wherein $X_1$ is —NH— or S; and $R^x$, $R^y$, and $R^z$ are each hydrogen;
  and
  —$X_1$—(R,R—CH($R^x$)C$R^y$($R^z$))—; wherein $X_1$ is —NH—, and $R^x$ and $R^z$ are methyl, and $R^y$ is hydrogen;
u) $L_2$ is a bivalent radical selected from the group consisting of
  —NH-cyclohexyl-(CH$_2$)$_{0-2}$— and Q is attached at either the 2- or cis-4-position relative to the position of —NH—;
  —$X_1$—CH($R^x$)—(C$R^yR^z$)—; wherein $X_1$ is —NH— or S and $R^x$, $R^y$, and $R^z$ are each hydrogen;
  and
  —$X_1$—(R,R—CH($R^x$)C$R^y$($R^z$))—; wherein $X_1$ is —NH—, $R^x$ and $R^z$ are methyl, and $R^y$ is hydrogen;
v) m is 0;
w) $R^a$ and $R^d$ are independently hydrogen or $C_{1-6}$alkyl, wherein $C_{1-6}$alkyl is optionally substituted with one to three substituents independently selected from the group consisting of hydroxy, $C_{1-4}$alkoxy, fluoro, amino, $C_{1-4}$alkylamino, di$C_{1-4}$alkylamino, and $C_{1-4}$alkylcarbonyl; or $R^a$ and $R^c$ are taken together with the atoms to which they are attached to form a 5-8 membered monocyclic ring optionally substituted with oxo;
x) $R^a$ and $R^d$ are independently hydrogen or $C_{1-3}$alkyl, wherein $C_{1-3}$alkyl is optionally substituted with one to three substituents independently selected from the group consisting of hydroxy, $C_{1-4}$alkoxy, fluoro, amino, $C_{1-4}$alkylamino, di$C_{1-4}$alkylamino, and $C_{1-4}$alkylcarbonyl; or $R^a$ and $R^c$ are taken together with the atoms to which they are attached to form a 5-8 membered monocyclic ring optionally substituted with oxo;
y) $R^a$ and $R^d$ are independently hydrogen, methyl or ethyl; or $R^a$ and $R^c$ are taken together with the atoms to which they are attached to form a 5-8 membered monocyclic ring optionally substituted with oxo;
z) $R^a$ and $R^d$ are independently hydrogen, methyl or ethyl;
aa) $R^b$ is hydrogen, $C_{1-6}$alkyl, $C_{2-6}$alkoxycarbonyl, or cyano; or, $R^b$ and $R^c$ are taken together with the atoms to which they are attached to form a 5-8 membered monocyclic ring, optionally substituted with oxo;
bb) $R^b$ is hydrogen or $C_{1-4}$alkyl; or, $R^b$ and $R^c$ are taken together with the atoms to which they are attached to form a 5-8 membered monocyclic ring, optionally substituted with oxo;
cc) $R^b$ is hydrogen
dd) $R^c$ is hydrogen, $C_{1-10}$alkyl, $C_{2-10}$alkenyl, $C_{3-7}$cycloalkyl, adamantyl, amino, arylcarbonyl, aryl, heteroaryl, or heterocyclyl; wherein C$_{1-10}$alkyl is optionally substituted with one to two subtituents independently selected from the group consisting of C$_{1-4}$alkoxy, trifluoromethyl, aryl, heteroaryl, and heterocyclyl; and wherein any aryl- or heteroaryl-containing substituents of R$^c$ are optionally substituted with one to three substituents independently selected from the group consisting of C$_{1-6}$alkyl, C$_{1-6}$alkoxy, halogen, fluorinated C$_{1-6}$alkyl, fluorinated C$_{1-6}$alkoxy, C$_{1-6}$alkylcarbonyl, C$_{1-6}$alkoxycarbonyl, nitro, methylthio, hydroxy, and cyano; or, R$^c$ and R$^d$ are taken together with the atoms to which they are attached to form a 5-8 membered monocyclic ring that optionally includes 1 to 2 O or S heteroatoms within the ring, and said ring is optionally substituted with oxo;

ee) R$^c$ is hydrogen, C$_{1-6}$alkyl, C$_{2-6}$alkenyl, C$_{3-7}$cycloalkyl, adamantyl, heterocyclyl, arylcarbonyl, phenyl, or heteroaryl; wherein C$_{1-6}$alkyl is optionally substituted with one to two substituents independently selected from the group consisting of C$_{1-3}$alkoxy, trifluoromethyl, phenyl, heteroaryl, and heterocyclyl; and wherein any aryl-, phenyl-, or heteroaryl-containing substituents of R$^c$ are optionally substituted with one to three substituents independently selected from the group consisting of C$_{1-6}$alkyl, C$_{1-6}$alkoxy, halogen, fluorinated C$_{1-6}$alkyl, fluorinated C$_{1-6}$alkoxy, C$_{1-6}$alkylcarbonyl, C$_{1-6}$alkoxycarbonyl, nitro, methylthio, hydroxy, and cyano; or, R$^c$ and R$^d$ are taken together with the atoms to which they are attached to form a 5-8 membered monocyclic ring and said ring is optionally substituted with oxo;

ff) R$^c$ is hydrogen, C$_{1-6}$alkyl, C$_{2-6}$alkenyl, C$_{3-7}$cycloalkyl, heterocyclyl, phenylcarbonyl, phenyl, or heteroaryl; wherein C$_{1-6}$alkyl is optionally substituted with one to two substituents independently selected from the group consisting of C$_{1-3}$alkoxy, phenyl, pyridinyl, furanyl, and tetrahydrofuranyl; and wherein any phenyl- or heteroaryl-containing substituents of R$^c$ are optionally substituted with one to two substituents independently selected from the group consisting of C$_{1-6}$alkyl, C$_{1-6}$alkoxy, chloro, fluoro, bromo, fluorinated C$_{1-3}$alkoxy, nitro, methylthio, hydroxy, and cyano; or, R$^c$ and R$^d$ are taken together with the atoms to which they are attached to form a 5-8 membered monocyclic ring;

gg) R$^b$ is hydrogen, C$_{1-4}$alkyl, C$_{2-4}$alkenyl, cyclohexyl, phenylcarbonyl, phenyl, pyrimidinyl, furanyl, benzo[1,3]dioxolyl, or pyridinyl; wherein C$_{1-4}$alkyl is optionally substituted with one to two substituents independently selected from the group consisting of C$_{1-3}$alkoxy, phenyl, pyridinyl, furanyl, and tetrahydrofuranyl; and wherein any phenyl- or heteroaryl-containing substituents of R$^c$ are optionally substituted with one to two substituents independently selected from the group consisting of C$_{1-6}$alkyl, C$_{1-6}$alkoxy, chloro, fluoro, bromo, fluorinated C$_{1-3}$alkoxy, nitro, methylthio, hydroxy, and cyano; or, R$^c$ and R$^d$ are taken together with the atoms to which they are attached to form a 5-8 membered monocyclic ring;

hh) R$^c$ is hydrogen, C$_{1-4}$alkyl, C$_{2-4}$alkenyl, cyclohexyl, phenylcarbonyl, phenyl, pyrimidinyl, furanyl, benzo[1,3]dioxolyl, or pyridinyl; wherein C$_{1-4}$alkyl is optionally substituted with one to two substituents independently selected from the group consisting of methoxy, phenyl, pyridinyl, furanyl, and tetrahydrofuranyl; and wherein any phenyl- or heteroaryl-containing substituents of R$^c$ are optionally substituted with one to two substituents independently selected from the group consisting of C$_{1-3}$alkyl, C$_{1-3}$alkoxy, chloro, fluoro, bromo, trifluoromethoxy, nitro, hydroxy, and cyano; or, R$^b$ and R$^d$ are taken together with the atoms to which they are attached to form a 5-6 membered monocyclic ring;

with the proviso that in any instance, only one ring optionally exists between R$^a$ and R$^b$, R$^b$ and R$^c$, or R$^c$ and R$^d$;

and combinations of a) through hh) above.

One aspect of the present invention is directed to compositions comprising a compound of Formula (Ia):

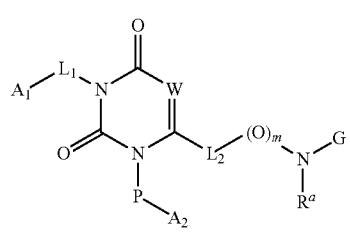

Formula (Ia)

wherein:

A$_1$ is hydrogen; aryl; heteroaryl; C$_{5-8}$cycloalkyl; or heterocyclyl provided that A$_1$ is other than piperidin-4-yl, N-t-butoxycarbonyl-piperidin-4-yl, or N-methyl-piperidin-3-yl; and wherein substituents of A$_1$ other than hydrogen are optionally substituted with one to three substituents independently selected from the group consisting of C$_{1-6}$alkyl, hydroxy(C$_{1-6}$)alkyl, C$_{1-6}$alkoxy, halogen, nitro, halogenated C$_{1-6}$alkyl, halogenated C$_{1-6}$alkoxy, C$_{1-6}$alkylthio, C$_{1-6}$alkoxycarbonyl, amino, cyano, hydroxy, aminocarbonyl, C$_{1-6}$alkylaminocarbonyl, di(C$_{1-6}$alkyl)aminocarbonyl, and C$_{1-6}$alkylcarbonyl;

L$_1$ is —(CH$_2$)$_r$— optionally substituted with one to three substituents independently selected from the group consisting of C$_{1-6}$alkyl, C$_{2-6}$alkenyl, C$_{2-6}$alkynyl, and halogen; provided that when A$_1$ is hydrogen, r is greater than or equal to 4;

r is an integer of 1 to 5;

P is —(CH$_2$)$_{4-6}$— when A$_2$ is hydrogen; and P is —(CH$_2$)$_{1-2}$— or —CH$_2$CH=CH— when A$_2$ is other than hydrogen;

A$_2$ is hydrogen, heteroaryl other than unsubstituted pyridin-2-yl, C$_{3-8}$cycloalkyl, or phenyl optionally substituted at the meta and para positions with one to three substituents independently selected from the group consisting of C$_{1-6}$alkyl, C$_{1-6}$alkoxy, halogen, halogenated C$_{1-6}$alkyl, halogenated C$_{1-6}$alkoxy, aryl(C$_{1-6}$)alkoxy, phenyl, C$_{1-6}$alkylthio, C$_{1-6}$alkoxycarbonyl, amino, cyano, hydroxy, nitro, aminocarbonyl, C$_{1-6}$alkylcarbonylamino, and a non fused C$_{3-6}$cycloalkyloxy; wherein heteroaryl other than unsubstituted pyridin-2-yl and C$_{3-8}$cycloalkyl are optionally substituted with one to three substituents independently selected from the group consisting of C$_{1-6}$alkyl, C$_{1-6}$alkoxy, halogen, halogenated C$_{1-6}$alkyl, halogenated C$_{1-6}$alkoxy, aryl(C$_{1-6}$)alkoxy, phenyl, C$_{1-6}$alkylthio, C$_{1-6}$alkoxycarbonyl, amino, cyano, hydroxy, nitro, aminocarbonyl, C$_{1-6}$alkylcarbonylamino, and a non fused C$_{3-6}$cycloalkyloxy;

provided that no more than two substituents on A$_2$ are aryl(C$_{1-6}$)alkoxy, phenyl, or a non fused C$_{3-6}$cycloalkyloxy;

provided that when A$_1$ is unsubstituted phenyl and L$_2$ is —X$_1$—CH(R$^x$)—(CR$^y$R$^z$)— wherein X$_1$ is NH, and R$^x$, R$^y$, and R$^z$ are each hydrogen, A$_2$ is other than unsubstituted phenyl; phenyl substituted with aryl(C$_{1-6}$)alkoxy or phenyl; or phenyl substituted at the meta position with cyano;

and, further provided that when $A_1$ is unsubstituted phenyl and $L_2$ is —$X_1(CH_2)_3$— wherein $X_1$ is NH, $A_2$ is other than phenyl substituted with methoxy;

and, provided that when $A_1$ is 3,4-dichloro-phenyl and P is —$CH_2$—, $A_2$ is other than phenyl substituted in the meta position with trifluoromethyl or trifluoromethoxy;

and, further provided that when $A_1$ is 3,4-dichloro-phenyl and P is —$(CH_2)_2$—, $A_2$ is other than 4-methoxy-phenyl;

W is N or CH;

$L_2$ is a bivalent radical selected from the group consisting of
—NH—$C_{6-7}$cycloalkyl-$(CH_2)_{0-2}$—; provided that when $C_{5-7}$cycloalkyl is cyclohexyl, Q is attached at either the 2- or cis-4-position relative to the position of —NH—;
—$X_2$—$(CH_2)_{0-4}$—;
—$X_1$—$(CH_2)_{2-3}$—$X_3$—$(CH_2)_{2-3}$—;
—$NH(CH_2)_{1-4}C(=O)$— provided that at least one of $R^b$, $R^c$, or $R^d$ is other than hydrogen and m is 0;
—$NHC(=O)$—$(CH_2)_{1-4}$—;
—$C(=O)NH(CR^yR^z)_{2-5}$—;
and
—$X_1$—$CH(R^x)$—$(CR^yR^z)_{1-5}$—; such that when $X_1$ is a direct bond and W is $C(R_w)$, then $R^x$ of $CH(R^x)$ is hydrogen;
wherein $X_1$ is —NH—, O, S, or a direct bond; such that $X_1$ is other than O when W is N;
$X_2$ is —CH=CH—;
$X_3$ is O, S, NH, or C=O;
$R^x$, $R^y$, and $R^z$ are independently H or $C_{1-4}$alkyl;
and provided that $L_2$ in any instance does not exceed 7 atoms in length;
and further provided that when $L_2$ is —$X_2$—$(CH_2)_{0-4}$— or —$C(=O)NH(CR^yR^z)_{2-6}$—, then $R_W$ is hydrogen;

m is 0 or 1;

G is —$C(=NR^b)NR^cR^d$;

$R^a$ and $R^d$ are independently hydrogen or $C_{1-6}$alkyl, wherein $C_{1-6}$alkyl is optionally substituted with one to three substituents independently selected from the group consisting of hydroxy, $C_{1-4}$alkoxy, fluoro, amino, $C_{1-4}$alkylamino, di$C_{1-4}$alkylamino, and $C_{1-4}$alkylcarbonyl; or $R^a$ and $R^c$ are taken together with the atoms to which they are attached to form a 5-8 membered monocyclic ring optionally substituted with oxo;

$R^b$ is hydrogen, $C_{1-6}$alkyl, $C_{2-6}$alkoxycarbonyl, or cyano; or, $R^b$ and $R^c$ are taken together with the atoms to which they are attached to form a 5-8 membered monocyclic ring optionally substituted with oxo;

$R^c$ is hydrogen, $C_{1-10}$ alkyl, $C_{2-10}$alkenyl, $C_{3-7}$cycloalkyl, adamantyl, amino, arylcarbonyl, aryl, heteroaryl, or heterocyclyl; wherein $C_{1-10}$alkyl is optionally substituted with one to two substituents independently selected from the group consisting of $C_{1-4}$alkoxy, trifluoromethyl, aryl, heteroaryl, and heterocyclyl; and wherein any aryl- or heteroaryl-containing substituents of $R^c$ are optionally substituted with one to three substituents independently selected from the group consisting of $C_{1-6}$alkyl, $C_{1-6}$alkoxy, halogen, fluorinated $C_{1-6}$alkyl, fluorinated $C_{1-6}$alkoxy, $C_{1-6}$alkylcarbonyl, $C_{1-6}$alkoxycarbonyl, nitro, methylthio, hydroxy, and cyano; or, $R^c$ and $R^d$ are taken together with the atoms to which they are attached to form a 5-8 membered monocyclic ring that optionally includes 1 to 2 O or S heteroatoms within the ring, and said ring is optionally substituted with oxo;

with the proviso that in any instance, only one ring optionally exists between $R^a$ and $R^b$, $R^b$ and $R^c$, or $R^c$ and $R^d$;

and enantiomers, diastereomers, tautomers, solvates, and pharmaceutically acceptable salts thereof.

A further aspect of the present invention is directed to a compound of Formula Ia wherein:

$A_1$ is hydrogen; aryl; heteroaryl; $C_{5-8}$cycloalkyl; or heterocyclyl other than piperidinyl; wherein substituents of $A_1$ other than hydrogen are optionally substituted with one to three substituents independently selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkoxycarbonyl, amino, cyano, hydroxy, aminocarbonyl, $C_{1-6}$alkylaminocarbonyl, di($C_{1-6}$alkyl)aminocarbonyl, and $C_{1-6}$alkylcarbonyl;

$L_1$ is —$(CH_2)_r$— optionally substituted with a substituent selected from the group consisting of $C_{1-4}$alkyl, $C_{2-4}$alkenyl, and $C_{2-4}$alkynyl; provided that r is 1 to 3 when $A_1$ is other than hydrogen; or r is 4 or 5 when $A_1$ is hydrogen;

P is —$CH_2$—;

$A_2$ is furanyl, pyridin-3-yl, pyridin-4-yl, or phenyl optionally substituted at the meta and para positions with one to three substituents independently selected from the group consisting of $C_{1-4}$alkyl, $C_{1-4}$alkoxy, halogen, halogenated $C_{1-3}$alkoxy, $C_{1-3}$alkylthio; hydroxy, amino, aminocarbonyl, $C_{1-3}$alkylcarbonylamino, and a non fused $C_{3-6}$cycloalkyloxy; and wherein furanyl, pyridin-3-yl, and pyridin-4-yl are optionally substituted with one to three substituents independently selected from the group consisting of $C_{1-4}$alkyl, $C_{1-4}$alkoxy, halogen, halogenated $C_{1-3}$alkoxy, $C_{1-3}$alkylthio, hydroxy, amino, aminocarbonyl, $C_{1-3}$alkylcarbonylamino, and a non fused $C_{3-6}$cycloalkyloxy;

provided that no more than two substituents on $A_2$ are non fused $C_{3-6}$cycloalkyloxy;

provided that when $A_1$ is unsubstituted phenyl and $L_2$ is —$X_1$—$CH(R^x)$—$(CR^yR^z)$— wherein $X_1$ is NH, and $R^x$, $R^y$, and $R^z$ are each hydrogen, $A_2$ is other than unsubstituted phenyl;

and, further provided that when $A_1$ is unsubstituted phenyl and $L_2$ is —$X_1$—$CH(R^x)$—$(CR^yR^z)_2$— wherein $X_1$ is NH and $R^x$, $R^y$, and $R^z$ are each hydrogen, $A_2$ is other than phenyl substituted with methoxy;

and, provided that when $A_1$ is 3,4-dichloro-phenyl, $A_2$ is other than phenyl substituted in the meta position with trifluoromethoxy;

W is N or CH;

$L_2$ is a bivalent radical selected from the group consisting of
—NH—$C_{5-6}$cycloalkyl-$(CH_2)_{0-2}$—; provided that when $C_{5-6}$cycloalkyl is cyclohexyl, Q is attached at either the 2- or cis-4-position relative to the position of —NH—;
—$X_1$—$CH(R^x)$—$(CR^yR^z)_{1-5}$—, wherein $X_1$ is —NH—, O, or S; and $R^x$, $R^y$, and $R^z$ are each hydrogen; such that $X_1$ is other than O when W is N;
—$C(=O)NH(CH_2)_2$—;
and
—$X_1$—$(R,R$—$CH(R^x)CR^y(R^z))$—; wherein $X_1$ is —NH—, and $R^x$ and $R^z$ are methyl, and $R^y$ is hydrogen;
provided that when $L_2$ is —$C(=O)NH(CH_2)_2$—, then $R_W$ is hydrogen;

m is 0 or 1;

G is —$C(=NR^b)NR^cR^d$;

$R^a$ and $R^d$ are independently hydrogen or $C_{1-3}$alkyl, wherein $C_{1-3}$alkyl is optionally substituted with one to three substituents independently selected from the group consisting of hydroxy, $C_{1-4}$alkoxy, fluoro, amino, $C_{1-4}$alkylamino, di$C_{1-4}$alkylamino, and $C_{1-4}$alkylcarbonyl; or $R^a$ and $R^c$ are taken together with the atoms to which they are attached to form a 5-8 membered monocyclic ring optionally substituted with oxo;

$R^b$ is hydrogen or $C_{1-4}$alkyl; or, $R^b$ and $R^c$ are taken together with the atoms to which they are attached to form a 5-8 membered monocyclic ring, optionally substituted with oxo;

$R^c$ is hydrogen, $C_{1-6}$alkyl, $C_{2-6}$alkenyl, $C_{3-7}$cycloalkyl, adamantyl, heterocyclyl, arylcarbonyl, phenyl, or heteroaryl; wherein $C_{1-6}$alkyl is optionally substituted with one to two substituents independently selected from the group consisting of $C_{1-3}$alkoxy, trifluoromethyl, phenyl, heteroaryl, and heterocyclyl; and wherein any aryl-, phenyl-, or heteroaryl-containing substituents of $R^c$ are optionally substituted with one to three substituents independently selected from the group consisting of $C_{1-6}$alkyl, $C_{1-6}$alkoxy, halogen, fluorinated $C_{1-6}$alkyl, fluorinated $C_{1-6}$alkoxy, $C_{1-6}$alkylcarbonyl, $C_{1-6}$alkoxycarbonyl, nitro, methylthio, hydroxy, and cyano; or, $R^c$ and $R^d$ are taken together with the atoms to which they are attached to form a 5-8 membered monocyclic ring and said ring is optionally substituted with oxo;

with the proviso that in any instance, only one ring optionally exists between $R^a$ and $R^b$, $R^b$ and $R^c$, or $R^c$ and $R^d$;

and enantiomers, diastereomers, tautomers, solvates, and pharmaceutically acceptable salts thereof.

A further aspect of the present invention is directed to a compound of Formula Ia wherein:

$A_1$ is substituted phenyl, benzofuranyl, thiazolyl, or thiophenyl; wherein phenyl is substituted with, and benzofuranyl, thiazolyl, and thiophenyl are optionally substituted with, one to two substituents independently selected from the group consisting of $C_{1-4}$alkyl, $C_{1-4}$alkoxy, halogen, nitro, halogenated $C_{1-4}$alkyl, halogenated $C_{1-4}$alkoxy, methylthio, amino, cyano, and $C_{1-4}$alkylcarbonyl;

$L_1$ is —$(CH_2)_r$— optionally substituted with a substituent selected from the group consisting of methyl and allyl, and r is 1 to 3;

$A_2$ is pyridin-3-yl, pyridin-4-yl, or phenyl optionally substituted at the meta and para positions with one to two substituents independently selected from the group consisting of methyl, ethyl, methoxy, ethoxy, isopropyloxy, trifluoromethoxy, difluoromethoxy, hydroxy, aminocarbonyl, and methylcarbonylamino; wherein pyridin-3-yl and pyridin-4-yl are optionally substituted with one to two substituents independently selected from the group consisting of methyl, ethyl, methoxy, ethoxy, isopropyloxy, trifluoromethoxy, difluoromethoxy, hydroxy, aminocarbonyl, and methylcarbonylamino;

P is —$CH_2$—;

W is N or CH;

$L_2$ is a bivalent radical selected from the group consisting of
—NH-cyclohexyl-$(CH_2)_{0-2}$— and Q is attached at either the 2- or cis-4-position relative to the position of —NH—;
—$X_1$—$CH(R^x)$—$(CR^yR^z)_{1-5}$—; wherein $X_1$ is —NH— or S; and $R^x$, $R^y$, and $R^z$ are each hydrogen; and
$X_1$—(R,R—$CH(R^x)CR^y(R^z)$)—; wherein $X_1$ is —NH—, and $R^x$ and $R^z$ are methyl, and $R^y$ is hydrogen;

m is 0;

G is —C(=$NR^b$)$NR^cR^d$;

$R^a$ and $R^d$ are independently hydrogen, methyl or ethyl; or $R^a$ and $R^c$ are taken together with the atoms to which they are attached to form a 5-8 membered monocyclic ring optionally substituted with oxo;

$R^b$ is hydrogen;

$R^c$ is hydrogen, $C_{1-6}$alkyl, $C_{2-6}$alkenyl, $C_{3-7}$cycloalkyl, heterocyclyl, phenylcarbonyl, phenyl, or heteroaryl; wherein $C_{1-6}$alkyl is optionally substituted with one to two substituents independently selected from the group consisting of $C_{1-3}$alkoxy, phenyl, pyridinyl, furanyl, and tetrahydrofuranyl; and wherein any phenyl- or heteroaryl-containing substituents of $R^c$ are optionally substituted with one to two substituents independently selected from the group consisting of $C_{1-6}$alkyl, $C_{1-6}$alkoxy, chloro, fluoro, bromo, fluorinated $C_{1-3}$alkoxy, nitro, methylthio, hydroxy, and cyano; or, $R^b$ and $R^d$ are taken together with the atoms to which they are attached to form a 5-8 membered monocyclic ring;

with the proviso that in any instance, only one ring optionally exists between $R^a$ and $R^b$, $R^b$ and $R^c$, or $R^c$ and $R^d$;

and enantiomers, diastereomers, tautomers, solvates, and pharmaceutically acceptable salts thereof.

Another aspect of the present invention is directed to a compound of Formula Ia wherein:

$A_1$ is phenyl or benzofuranyl; wherein phenyl is substituted at either the 4-position or 3 and 4-positions with one to two substituents independently selected from the group consisting of ethyl, methoxy, fluoro, chloro, nitro, difluoromethoxy, and methylthio;

$L_1$ is —$CH_2$— optionally substituted with methyl or allyl;

$A_2$ is phenyl substituted at the para position with a substituent selected from the group consisting of methoxy, ethoxy, isopropyloxy, difluoromethoxy, hydroxy, and aminocarbonyl; or $A_2$ is pyridin-3-yl or pyridin-4-yl substituted with methoxy;

P is —$CH_2$—;

W is N or CH;

$L_2$ is a bivalent radical selected from the group consisting of
—NH-cyclohexyl-$(CH_2)_{0-2}$— and Q is attached at either the 2- or cis-4-position relative to the position of —NH—;
—$X_1$—$CH(R^x)$—$(CR^yR^z)$—; wherein $X_1$ is —NH— or S and $R^x$, $R^y$, and $R^z$ are each hydrogen; and
—$X_1$—(R,R—$CH(R^x)CR^y(R^z)$)—; wherein $X_1$ is —NH—, $R^x$ and $R^z$ are methyl, and $R^y$ is hydrogen;

m is 0;

G is —C(=$NR^b$)$NR^cR^d$;

$R^a$ and $R^d$ are independently hydrogen, methyl or ethyl;

$R^b$ is hydrogen;

$R^c$ is hydrogen, $C_{1-4}$alkyl, $C_{2-4}$alkenyl, cyclohexyl, phenylcarbonyl, phenyl, pyrimidinyl, furanyl, benzo[1,3]dioxolyl, or pyridinyl; wherein $C_{1-4}$alkyl is optionally substituted with one to two substituents independently selected from the group consisting of $C_{1-3}$alkoxy, phenyl, pyridinyl, furanyl, and tetrahydrofuranyl; and wherein any phenyl- or heteroaryl-containing substituents of $R^c$ are optionally substituted with one to two substituents independently selected from the group consisting of $C_{1-6}$alkyl, $C_{1-6}$alkoxy, chloro, fluoro, bromo, fluorinated $C_{1-3}$alkoxy, nitro, methylthio, hydroxy, and cyano; or, $R^c$ and $R^d$ are taken together with the atoms to which they are attached to form a 5-8 membered monocyclic ring;

and enantiomers, diastereomers, tautomers, solvates, and pharmaceutically acceptable salts thereof.

Another aspect of the present invention is directed to compounds of Formula (I) in Table 1 wherein $A_1$, $L_1$, D, W, $L_2$, and Q are as defined in the present invention.

TABLE 1

| Cpd # | A$_1$ | L$_1$ | D | W | L$_2$ | Q |
|---|---|---|---|---|---|---|
| 1 | phenyl | —CH$_2$— | —CH$_2$-(4-fluoro-phenyl) | N | —NH(CH$_2$)$_2$— | —NHC(=NH)NH$_2$ |
| 2 | phenyl | —CH$_2$— | —CH$_2$-(4-methoxy-phenyl) | N | —NH(CH$_2$)$_2$— | —NHC(=NH)NH$_2$ |
| 3 | phenyl | —CH$_2$— | —CH$_2$-(4-methylcarboxy-phenyl) | N | —NH(CH$_2$)$_2$— | —NHC(=NH)NH$_2$ |
| 4 | phenyl | —(CH$_2$)$_2$— | —CH$_2$-(4-methoxy-phenyl) | N | —NH(CH$_2$)$_2$— | —NHC(=NH)NH$_2$, |
| 5 | H | —(CH$_2$)$_4$— | —CH$_2$-(4-methoxy-phenyl) | N | —NH(CH$_2$)$_2$— | —NHC(=NH)NH$_2$ |
| 6 | furan-2-yl | —CH$_2$— | —CH$_2$-(4-methoxy-phenyl) | N | —NH(CH$_2$)$_2$— | —NHC(=NH)NH$_2$ |
| 7 | phenyl | —CH$_2$— | —CH$_2$-(3-trifluoromethyl-phenyl) | N | —NH(CH$_2$)$_2$— | —NHC(=NH)NH$_2$ |
| 8 | phenyl | —CH$_2$— | —CH$_2$-(4-t-butyl-phenyl) | N | —NH(CH$_2$)$_2$— | —NHC(=NH)NH$_2$ |
| 9 | phenyl | —CH$_2$— | —CH$_2$-(4-nitro-phenyl) | N | —NH(CH$_2$)$_2$— | —NHC(=NH)NH$_2$ |
| 10 | phenyl | —CH$_2$— | —CH$_2$-(4-methoxy-phenyl) | N | —NH(CH$_2$)$_2$— | —ONHC(=NH)NH$_2$ |
| 11 | phenyl | —CH$_2$— | —CH$_2$-pyridin-4-yl | N | —NH(CH$_2$)$_2$— | —NHC(=NH)NH$_2$ |
| 12 | phenyl | —CH$_2$— | —CH$_2$-(4-ethoxy-phenyl) | N | —NH(CH$_2$)$_2$— | —NHC(=NH)NH$_2$ |
| 13 | phenyl | —CH$_2$— | —CH$_2$-(4-difluoromethoxy-phenyl) | N | —NH(CH$_2$)$_2$— | —NHC(=NH)NH$_2$ |
| 14 | phenyl | —CH$_2$— | —CH$_2$-(4-n-butyl-phenyl) | N | —NH(CH$_2$)$_2$— | —NHC(=NH)NH$_2$ |
| 15 | phenyl | —CH$_2$— | —CH$_2$-(4-trifluoromethyl-phenyl) | N | —NH(CH$_2$)$_2$— | —NHC(=NH)NH$_2$ |
| 16 | 2-fluoro-phenyl | —CH$_2$— | —CH$_2$-(4-methoxy-phenyl) | N | —NH(CH$_2$)$_2$— | —NHC(=NH)NH$_2$ |
| 17 | 4-fluoro-phenyl | —CH$_2$— | —CH$_2$-(4-methoxy-phenyl) | N | —NH(CH$_2$)$_2$— | —NHC(=NH)NH$_2$ |
| 18 | 3,4-dichloro-phenyl | —CH$_2$— | —CH$_2$-(4-methoxy-phenyl) | N | —NH(CH$_2$)$_2$— | —NHC(=NH)NH$_2$ |
| 19 | phenyl | —CH$_2$— | —CH$_2$-(4-trifluoromethoxy-phenyl) | N | —NH(CH$_2$)$_2$— | —NHC(=NH)NH$_2$ |
| 20 | 3-methoxy-phenyl | —CH$_2$— | —CH$_2$-(4-methoxy-phenyl) | N | —NH(CH$_2$)$_2$— | —NHC(=NH)NH$_2$ |
| 21 | 2-methoxy-phenyl | —CH$_2$— | —CH$_2$-(4-methoxy-phenyl) | N | —NH(CH$_2$)$_2$— | —NHC(=NH)NH$_2$ |
| 22 | phenyl | —CH$_2$— | —CH$_2$-(4-aminocarbonyl-phenyl) | N | —NH(CH$_2$)$_2$— | —NHC(=NH)NH$_2$ |
| 23 | phenyl | —CH$_2$— | —CH$_2$-(4-methylcarboxyl amino-phenyl) | N | —NH(CH$_2$)$_2$— | —NHC(=NH)NH$_2$ |
| 24 | 4-fluoro-phenyl | —CH$_2$— | —CH$_2$-(4-ethoxy-phenyl) | N | —NH(CH$_2$)$_2$— | —NHC(=NH)NH$_2$ |
| 25 | phenyl | —(R,R—CH(CH$_3$)CH(CH$_3$))— | —CH$_2$-(4-methoxy-phenyl) | N | —NH(CH$_2$)$_2$— | —NHC(=NH)NH$_2$ |
| 26 | phenyl | —(R,R—CH(CH$_3$)CH(CH$_3$))— | —CH$_2$-(4-methoxy-phenyl) | N | —NH(CH$_2$)$_2$— | —NHC(=NH)NH$_2$ |
| 27 | 3,4-dichloro-phenyl | —CH$_2$— | —CH$_2$-(4-methoxy-phenyl) | N | —NH(CH$_2$)$_2$— | —ONHC(=NH)NH$_2$ |
| 28 | 3,4-dichloro-phenyl | —CH$_2$— | —CH$_2$-(4-methoxy-phenyl) | N | —NH(CH$_2$)$_2$— | —NHC(=N—CN)NH$_2$ |
| 29 | 3,4-dichloro-phenyl | —CH$_2$— | —CH$_2$-(4-ethoxy-phenyl) | N | —NH(CH$_2$)$_2$— | —NHC(=NH)NH$_2$ |
| 30 | 4-chloro-phenyl | —CH$_2$— | —CH$_2$-(4-methoxy-phenyl) | N | —NH(CH$_2$)$_2$— | —NHC(=NH)NH$_2$ |
| 31 | 4-methoxy-phenyl | —CH$_2$— | —CH$_2$-(4-methoxy-phenyl) | N | —NH(CH$_2$)$_2$— | —NHC(=NH)NH$_2$ |
| 32 | 3,4-dichloro-phenyl | —CH$_2$— | —CH$_2$-(4-methoxy-phenyl) | N | —NH(CH$_2$)$_4$— | —NHC(=NH)NH$_2$ |
| 33 | 4-fluoro-phenyl | —CH$_2$— | —(CH$_2$)$_2$-(4-methoxy-phenyl) | N | —NH(CH$_2$)$_2$— | —NHC(=NH)NH$_2$ |
| 34 | 3,4-dichloro-phenyl | —CH$_2$— | —CH$_2$-(4-n-propyl-phenyl) | N | —NH(CH$_2$)$_2$— | —NHC(=NH)NH$_2$ |
| 35 | 3,4-dichloro-phenyl | —CH$_2$— | —CH$_2$-(4-i-propyl-phenyl) | N | —NH(CH$_2$)$_2$— | —NHC(=NH)NH$_2$ |

TABLE 1-continued

| Cpd # | A₁ | L₁ | D | W | L₂ | Q |
|---|---|---|---|---|---|---|
| 36 | 3,4-dichloro-phenyl | —CH₂— | —CH₂-(4-cyclopentyloxy-phenyl) | N | —NH(CH₂)₂— | —NHC(=NH)NH₂ |
| 37 | 3,4-dichloro-phenyl | —CH₂— | —CH₂-(4-methylthio-phenyl) | N | —NH(CH₂)₂— | —NHC(=NH)NH₂ |
| 38 | 3,4-dichloro-phenyl | —CH₂— | —CH₂-(4-ethyl-phenyl) | N | —NH(CH₂)₂— | —NHC(=NH)NH₂ |
| 39 | 3-chloro-phenyl | —CH₂— | —CH₂-(4-methoxy-phenyl) | N | —NH(CH₂)₂— | —NHC(=NH)NH₂ |
| 40 | 3,4-dichloro-phenyl | —CH₂— | —CH₂-(4-trifluoromethoxy-phenyl) | N | —NH(CH₂)₂— | —NHC(=NH)NH₂ |
| 41 | 3,4-dichloro-phenyl | —CH₂— | —CH₂-(4-difluoromethoxy-phenyl) | N | —NH(CH₂)₂— | —NHC(=NH)NH₂ |
| 42 | 3,4-dichloro-phenyl | —CH₂— | —CH₂-(4-methoxy-phenyl) | N | cis-racemic-1,2-cyclohexyl | —NHC(=NH)NH₂ |
| 43 | 3,4-dichloro-phenyl | —CH₂— | —CH₂-(4-methoxy-phenyl) | N | trans (1S,2S)-cyclohexyl- | —NHC(=NH)NH₂ |
| 44 | 3,4-dichloro-phenyl | —CH₂— | —CH₂-(4-methoxy-phenyl) | N | —NH(CH₂)₂— | —NHC(=NH)NH₂ |
| 45 | 4-methylthio-phenyl | —CH₂— | —CH₂-(4-methoxy-phenyl) | N | —NH(CH₂)₂— | —NHC(=NH)NH₂ |
| 46 | 4-ethyl-phenyl | —CH₂— | —CH₂-(4-methoxy-phenyl) | N | —NH(CH₂)₂— | —NHC(=NH)NH₂ |
| 47 | 3,4-dichloro-phenyl | —CH₂— | —CH₂-(4-methoxy-phenyl) | N | trans(1R,2R)-cyclohexyl- | —NHC(=NH)NH₂ |
| 48 | 3,4-dichloro-phenyl | —CH₂— | —CH₂-(4-methoxy-phenyl) | N | —NH(CH₂)₂— | —NH(3,5-dihydro-imidazol-4-on-2-yl) |
| 49 | 3,4-dichloro-phenyl | —CH₂— | —CH₂-(4-methoxy-phenyl) | N | —NH(CH₂)₂— | —NH(4,5-dihydro-1H-imidazol-2-yl) |
| 50 | 3,4-dichloro-phenyl | —CH₂— | —CH₂-(4-methylcarbonyl amino-phenyl) | N | —NH(CH₂)₂— | —NHC(=NH)NH₂ |
| 51 | 3,4-dichloro-phenyl | —CH₂— | —CH₂-(4-aminocarbonyl-phenyl) | N | —NH(CH₂)₂— | —NHC(=NH)NH₂ |
| 52 | 3,4-dichloro-phenyl | —CH₂— | —CH₂-(3-ethoxy-phenyl) | N | —NH(CH₂)₂— | —NHC(=NH)NH₂ |
| 53 | 3,4-dichloro-phenyl | —CH₂— | —CH₂-(4-ethoxy-phenyl) | N | —NH(CH₂)₂— | —NHC(=NH)NH-ethyl |
| 54 | 3,4-dichloro-phenyl | —CH₂— | —CH₂-(4-methoxy-phenyl) | N | —NH(CH₂)₂— | —NHC(=NH)NH-propy |
| 55 | 3,4-dichloro-phenyl | —CH₂— | —CH₂-(4-methoxy-phenyl) | N | pyrrolindin-1-yl 3- | NHC(=NH)NH₂ |
| 56 | 4-chloro-phenyl | —CH₂— | —CH₂-(4-methoxy-phenyl) | N | -trans (1R,2R)-cyclohexyl- | —NHC(=NH)NH₂ |
| 57 | 3,4-dichloro-phenyl | —CH₂— | —CH₂-(3-difluoromethoxy-phenyl) | N | —NH(CH₂)₂— | —NHC(=NH)NH₂ |
| 58 | 3,4-dichloro-phenyl | —CH₂— | —CH₂-(4-methoxy-phenyl) | N | —NH(CH₂)₂— | —NHC(=NH)NH (i-propyl) |
| 59 | 3,4-dichloro-phenyl | —CH₂— | —CH₂-(4-methoxy-phenyl) | N | —NH(CH₂)₂— | —N(ethyl)C(=NH)NH₂ |
| 60 | 3,4-dichloro-phenyl | —CH₂— | —CH₂-(4-methoxy-phenyl) | N | —NH(CH₂)₂— | 2-imino-imidazolid-1-yl |
| 61 | 3,4-dichloro-phenyl | —CH₂— | —CH₂-(4-methoxy-phenyl) | N | —NH(CH₂)₂— | —NHC(=NH)NH (n-butyl) |
| 62 | 3,4-dichloro-phenyl | —CH₂— | —CH₂-(4-methoxy-phenyl) | N | —NH(CH₂)₂— | —NHC(=NH)NH (cyclohexyl) |
| 63 | 3,4-dichloro-phenyl | —CH₂— | —CH₂-(4-methoxy-phenyl) | N | —NH(CH₂)₂— | —NHC(=NH)NH (benzyl) |
| 64 | 3,4-dichloro-phenyl | —CH₂— | —CH₂-(4-methoxy-phenyl) | N | —NH(CH₂)₂— | —NHC(=NH)NH (tetrahydrofuran-2-ylmethyl) |
| 65 | 3,4-dichloro-phenyl | —CH₂— | —CH₂-(4-methoxy-phenyl) | N | —NH(CH₂)₂— | —NHC(=NH)NH (phenylethyl) |
| 66 | 3,4-dichloro-phenyl | —CH₂— | —CH₂-(4-methoxy-phenyl) | N | —NH(CH₂)₂— | —NHC(=NH)NH (furan-2-ylmethyl) |
| 67 | 3,4-dichloro-phenyl | —CH₂— | —CH₂-(4-methoxy-phenyl) | N | —NH(CH₂)₂— | —NHC(=NH)NH (2-methoxy-ethyl) |
| 68 | 3,4-dichloro-phenyl | —CH₂— | —CH₂-(4-methoxy-phenyl) | N | —NH(CH₂)₃— | —NHC(=NH)NH₂ |
| 69 | 3,4-dichloro-phenyl | —CH₂— | —(CH₂)₆—H | N | —NH(CH₂)₃— | —NHC(=NH)NH₂ |
| 70 | 3,4-dichloro-phenyl | —CH₂— | —CH₂-(4-methoxy-phenyl) | N | —NH(CH₂)₂— | —NHC(=NH)NH (allyl) |

TABLE 1-continued

| Cpd # | A₁ | L₁ | D | W | L₂ | Q |
|---|---|---|---|---|---|---|
| 71 | 3,4-dichloro-phenyl | —CH₂— | —CH₂-(4-methoxy-phenyl) | N | —NH(CH₂)₂— | —NHC(=NH)NH(phenyl) |
| 72 | 3,4-dichloro-phenyl | —CH₂— | —CH₂-(4-methoxy-phenyl) | N | —NH(CH₂)₂— | —NHC(=NH)NH(4-methoxy-phenyl) |
| 73 | 3,4-dichloro-phenyl | —CH₂— | —CH₂-(4-methoxy-phenyl) | N | —NH(CH₂)₂— | —NHC(=NH)NH(4-chloro-phenyl) |
| 74 | 3,4-dichloro-phenyl | —CH₂— | —CH₂-(4-methoxy-phenyl) | N | —NH(CH₂)₂— | —NHC(=NH)NH(4-trifluoromethyl-phenyl) |
| 75 | 3,4-dichloro-phenyl | —CH₂— | —CH₂-(4-methoxy-phenyl) | N | —NH(CH₂)₂— | —NHC(=NH)NH(pyridin-3-yl) |
| 76 | 3,4-dichloro-phenyl | —CH₂— | —CH₂-(4-methoxy-phenyl) | N | —NH(CH₂)₂— | —NHC(=NH)NH(4-methylcarbonyl-phenyl) |
| 77 | furan-3-yl | —CH₂— | —CH₂-(4-methoxy-phenyl) | N | —NH(CH₂)₂— | —NHC(=NH)NH₂ |
| 78 | thiophen-2-yl | —CH₂— | —CH₂-(4-methoxy-phenyl) | N | —NH(CH₂)₂— | —NHC(=NH)NH₂ |
| 79 | 4-methoxy-phenyl | R,S-mixture —CH(CH₃)— | —CH₂-(4-methoxy-phenyl) | N | —NH(CH₂)₂— | —NHC(=NH)NH₂ |
| 80 | 4-difluoromethoxy-phenyl | —CH₂— | —CH₂-(4-methoxy-phenyl) | N | —NH(CH₂)₂— | —NHC(=NH)NH₂ |
| 81 | phenyl | —CH₂— | —CH₂-(4-methoxy-phenyl) | CH | —NH(CH₂)₂— | —NHC(=NH)NH₂ |
| 82 | 4-methoxy-phenyl | R,S-mixture —CH(allyl)- | —CH₂-(4-methoxy-phenyl) | N | —NH(CH₂)₂— | —NHC(=NH)NH₂ |
| 83 | 4-chloro-phenyl | R,S-mixture —CH(allyl)- | —CH₂-(4-methoxy-phenyl) | N | —NH(CH₂)₂— | —NHC(=NH)NH₂ |
| 84 | 4-methoxy-phenyl | —CH₂— | —CH₂-(4-methoxy-phenyl) | CH | —NH(CH₂)₂— | —NHC(=NH)NH₂ |
| 85 | 4-methoxy-phenyl | —CH₂— | —CH₂-(6-methoxy-pyridin-3-yl) | N | —NH(CH₂)₂— | —NHC(=NH)NH₂ |
| 86 | 4-methoxy-phenyl | —CH₂— | —CH₂-(4-methoxy-cyclohexyl) | N | —NH(CH₂)₂— | —NHC(=NH)NH₂ |
| 87 | 4-fluoro-phenyl | —CH₂— | —CH₂-(4-nitro-phenyl) | N | —NH(CH₂)₂— | —NHC(=NH)NH₂ |
| 88 | 4-fluoro-phenyl | —CH₂— | —CH₂-(4-methoxy-phenyl) | N | —NH(CH₂)₂— | —NHC(=NH)NH(2-(morpholin-4-yl)-eth-1-yl) |
| 89 | 4-fluoro-phenyl | —CH₂— | —CH₂-(4-methoxy-phenyl) | N | —NH(CH₂)₂— | —NHC(=NH)NH(3-(morpholin-4-yl)-prop-1-yl) |
| 90 | 4-fluoro-phenyl | —CH₂— | —CH₂-(4-methoxy-phenyl) | N | —NH(CH₂)₂— | —NHC(=NH)NH(4-cyano-phenyl) |
| 91 | 4-fluoro-phenyl | —CH₂— | —CH₂-(4-methoxy-phenyl) | N | —NH(CH₂)₂— | —NHC(=NH)NH(4-nitro-phenyl) |
| 92 | 4-fluoro-phenyl | —CH₂— | —CH₂-(4-methoxy-phenyl) | N | —NH(CH₂)₂— | —NHC(=NH)NH(1,3-benzo dioxol-5-yl) |
| 93 | 4-fluoro-phenyl | —CH₂— | —CH₂-(4-methoxy-phenyl) | N | —NH(CH₂)₂— | —NHC(=NH)NHNH₂ |
| 94 | 3-nitro-phenyl | —CH₂— | —CH₂-(4-methoxy-phenyl) | N | —NH(CH₂)₂— | —NHC(=NH)NH₂ |
| 95 | 4-nitro-phenyl | —CH₂— | —CH₂-(4-methoxy-phenyl) | N | —NH(CH₂)₂— | —NHC(=NH)NH₂ |
| 96 | 3-amino-phenyl | —CH₂— | —CH₂-(4-methoxy-phenyl) | N | —NH(CH₂)₂— | —NHC(=NH)NH₂ |
| 97 | 4-cyano-phenyl | —CH₂— | —CH₂-(4-methoxy-phenyl) | N | —NH(CH₂)₂— | —NHC(=NH)NH₂ |
| 98 | 3-cyano-phenyl | —CH₂— | —CH₂-(4-methoxy-phenyl) | N | —NH(CH₂)₂— | —NHC(=NH)NH₂ |
| 99 | 4-methoxy carbonyl-phenyl | —CH₂— | —CH₂-(4-methoxy-phenyl) | N | —NH(CH₂)₂— | —NHC(=NH)NH₂ |
| 100 | 3-methoxy carbonyl-phenyl | —CH₂— | —CH₂-(4-methoxy-phenyl) | N | —NH(CH₂)₂— | —NHC(=NH)NH₂ |
| 101 | 4-carboxy-phenyl | —CH₂— | —CH₂-(4-methoxy-phenyl) | N | —NH(CH₂)₂— | —NHC(=NH)NH₂ |
| 102 | 3,4-dichloro-phenyl | —CH₂— | —CH₂-(4-methoxy-phenyl) | N | —NH(CH₂)C(Me)₂— | —NHC(=NH)NH₂ |
| 103 | 4-fluoro-phenyl | —CH₂— | —CH₂-(4-methoxy-phenyl) | N | —NH(CH₂)₂— | —NHC(=NH)NH(4-bromo-phenyl) |
| 104 | 4-fluoro-phenyl | —CH₂— | —CH₂-(4-methoxy-phenyl) | N | —NH(CH₂)₂— | —NHC(=NH)NH(pyridin-2-yl) |
| 105 | 4-fluoro-phenyl | —CH₂— | —CH₂-(4-methoxy-phenyl) | N | —NH(CH₂)₂— | —NHC(=NH)NH(pyridin-2-yl-ethyl) |
| 106 | 4-fluoro-phenyl | —CH₂— | —CH₂-(4-methoxy-phenyl) | N | —NH(CH₂)₂— | —NHC(=NH)NH(4-ethoxycarbonyl-phenyl) |
| 107 | 4-fluoro-phenyl | —CH₂— | —CH₂-(4-methoxy-phenyl) | N | —NH(CH₂)₂— | —NHC(=NH)NH(2,4-difluoro-phenyl) |
| 108 | 4-fluoro-phenyl | —CH₂— | —CH₂-(4-methoxy-phenyl) | N | —NH(CH₂)₂— | —NHC(=NH)NH(n-decanyl) |

TABLE 1-continued

| Cpd # | $A_1$ | $L_1$ | D | W | $L_2$ | Q |
|---|---|---|---|---|---|---|
| 109 | 4-t-butoxy-phenyl | —CH$_2$— | —CH$_2$-(4-methoxy-phenyl) | N | —NH(CH$_2$)$_2$— | —NHC(=NH)NH$_2$ |
| 110 | 4-hydroxy-phenyl | —CH$_2$— | —CH$_2$-(4-methoxy-phenyl) | N | —NH(CH$_2$)$_2$— | —NHC(=NH)NH$_2$ |
| 111 | 2-chloro-thiazol-4-yl | —CH$_2$— | —CH$_2$-(4-methoxy-phenyl) | N | —NH(CH$_2$)$_2$— | —NHC(=NH)NH$_2$ |
| 112 | benzo furan-2-yl | —CH$_2$— | —CH$_2$-(4-methoxy-phenyl) | N | —NH(CH$_2$)$_2$— | —NHC(=NH)NH$_2$ |
| 113 | 3,4-dichloro-phenyl | —CH$_2$— | —CH$_2$-(4-methoxy-phenyl) | N | —NH(CH$_2$)$_2$— | —N(Me)C(=NH)NH$_2$ |
| 114 | 4-fluoro-phenyl | —CH$_2$— | —CH$_2$-(4-methoxy-phenyl) | N | —NH(CH$_2$)$_2$— | —NHC(=NH)NH(CH$_2$CF$_3$) |
| 115 | 4-fluoro-phenyl | —CH$_2$— | —CH$_2$-(4-methoxy-phenyl) | N | —NH(CH$_2$)$_2$— | —NHC(=NH)NH(3-methoxypropyl) |
| 116 | 4-fluoro-phenyl | —CH$_2$— | —CH$_2$-(4-methoxy-phenyl) | N | —NH(CH$_2$)$_2$— | —NHC(=NH)piperidin-1-yl |
| 117 | 4-fluoro-phenyl | —CH$_2$— | —CH$_2$-(4-methoxy-phenyl) | N | —NH(CH$_2$)$_2$— | —NHC(=NH)N(Me)phenyl |
| 118 | 4-fluoro-phenyl | —CH$_2$— | —CH$_2$-(4-methoxy-phenyl) | N | —NH(CH$_2$)$_2$— | —NHC(=NH)NH(2-fluoro-phenyl) |
| 119 | 4-fluoro-phenyl | —CH$_2$— | —CH$_2$-(4-methoxy-phenyl) | N | —NH(CH$_2$)$_2$— | —NHC(=NH)NH(4-fluoro-phenyl) |
| 120 | 4-fluoro-phenyl | —CH$_2$— | —CH$_2$-(4-methoxy-phenyl) | N | —NH(CH$_2$)$_2$— | —NHC(=NH)NH(4-methyl-phenyl) |
| 121 | 4-fluoro-phenyl | —CH$_2$— | —CH$_2$-(4-methoxy-phenyl) | N | —NH(CH$_2$)$_2$— | —NHC(=NH)NH(t-butyl) |
| 122 | 4-chloro-phenyl | —CH$_2$— | —CH$_2$-(4-amino-phenyl) | N | —NH(CH$_2$)$_2$— | —NHC(=NH)NH$_2$ |
| 123 | t-butyl | —CH$_2$— | —CH$_2$-(4-methoxy-phenyl) | N | —NH(CH$_2$)$_2$— | —NHC(=NH)NH$_2$ |
| 124 | cyclopentyl | —CH$_2$— | —CH$_2$-(4-methoxy-phenyl) | N | —NH(CH$_2$)$_2$— | —NHC(=NH)NH$_2$ |
| 125 | 4-amino-phenyl | —CH$_2$— | —CH$_2$-(4-methoxy-phenyl) | N | —NH(CH$_2$)$_2$— | —NHC(=NH)NH$_2$ |
| 126 | 4-fluoro-phenyl | —CH$_2$— | —CH$_2$-(4-methoxy-phenyl) | N | —NH(CH$_2$)$_2$— | —NHC(=NH)NH(adamantan-2-yl) |
| 127 | 4-fluoro-phenyl | —CH$_2$— | —CH$_2$-(4-methoxy-phenyl) | N | —NH(CH$_2$)$_2$— | —NHC(=NH)NH(4-trifluoromethoxy-phenyl) |
| 128 | 4-fluoro-phenyl | —CH$_2$— | —CH$_2$-(4-methoxy-phenyl) | N | —NH(CH$_2$)$_2$— | —NHC(=NH)NH(4-hydroxy-phenyl) |
| 129 | 4-chloro-phenyl | —CH$_2$— | —CH$_2$-phenyl | N | —NH(CH$_2$)$_2$— | —NHC(=NH)NH$_2$ |
| 130 | 4-chloro-phenyl | —CH$_2$— | —CH$_2$-furan-3-yl | N | —NH(CH$_2$)$_2$— | —NHC(=NH)NH$_2$ |
| 131 | 4-fluoro-phenyl | —CH$_2$— | —CH$_2$-(4-methoxy-phenyl) | N | 1,4-cyclohexyl | —NHC(=NH)NH$_2$ |
| 132 | 4-fluoro-phenyl | —CH$_2$— | —CH$_2$-(4-methoxy-phenyl) | N | —NHCH$_2$C(=O)— | —NHC(=NC(=O)O-t-butyl)NH$_2$ |
| 133 | 4-fluoro-phenyl | —CH$_2$— | —CH$_2$-(4-methoxy-phenyl) | N | —NH(CH$_2$)$_2$— | —NHC(=NH)NH(2-methylthio-phenyl) |
| 134 | 4-fluoro-phenyl | —CH$_2$— | —CH$_2$-(4-methoxy-phenyl) | N | —NH(CH$_2$)$_2$— | —NHC(=NH)NH(C(=O)phenyl) |
| 135 | 4-fluoro-phenyl | —CH$_2$— | —CH$_2$-(4-methoxy-phenyl) | N | —NH(CH$_2$)$_2$— | —NHC(=NH)NH(pyrimidin-2-yl) |
| 136 | 4-fluoro-phenyl | —CH$_2$— | —CH$_2$-(4-methoxy-phenyl) | N | —NH((S)—CHMe)$_2$— | —NHC(=NH)NH$_2$ |
| 137 | 4-fluoro-phenyl | —CH$_2$— | —CH$_2$-(4-methoxy-phenyl) | N | —NH((R)—CHMe)$_2$— | —NHC(=NH)NH$_2$, |
| 138 | 4-fluoro-phenyl | —CH$_2$— | —CH$_2$-(4-methoxy-phenyl) | N | —NH(CH$_2$)$_2$— | —NH(=NH)NH(4-trifluoromethyl-5,6,7,8-tetrahydro-quinazolin-2-yl) |
| 139 | 4-fluoro-phenyl | —CH$_2$— | —CH$_2$-(4-methoxy-phenyl) | N | —NH(CH$_2$)$_2$— | —NHC(=NH)NH(5-methyl-pyridin-2-yl) |
| 140 | 4-fluoro-phenyl | —CH$_2$— | —CH$_2$-(4-methoxy-phenyl) | N | —NH(CH$_2$)$_2$— | —NHC(=NH)morpholin-4-yl |
| 141 | 4-chloro-phenyl | —CH$_2$— | —CH$_2$-furan-2-yl | N | —NH(CH$_2$)$_2$— | —NHC(=NH)NH$_2$ |
| 142 | 4-chloro-phenyl | —CH$_2$— | —CH$_2$-(4-methoxy-phenyl) | N | —NH(CH$_2$)$_5$— | —NHC(=NH)NH$_2$ |
| 143 | 4-methoxy-phenyl | —CH$_2$— | —CH$_2$-(4-hydroxy-phenyl) | N | —NH(CH$_2$)$_2$— | —NHC(=NH)NH$_2$ |
| 144 | 4-chloro-phenyl | —CH$_2$— | —CH$_2$-(4-methoxy-phenyl) | N | —NH(CH$_2$)$_6$— | —NHC(=NH)NH$_2$ |
| 145 | 4-methoxy-phenyl | —(CH$_2$)$_2$— | —CH$_2$-(4-methoxy-phenyl) | N | —NH(CH$_2$)$_2$— | —NHC(=NH)NH$_2$ |
| 146 | 4-methoxy-phenyl | —(CH$_2$)$_3$— | —CH$_2$-(4-methoxy-phenyl) | N | —NH(CH$_2$)$_2$— | —NHC(=NH)NH$_2$ |
| 147 | 3,4-dichloro-phenyl | —CH$_2$— | —CH$_2$-(4-methoxycarbonyl-phenyl) | N | —NH(CH$_2$)$_2$— | —NHC(=NH)NH$_2$ |

TABLE 1-continued

| Cpd # | $A_1$ | $L_1$ | D | W | $L_2$ | Q |
|---|---|---|---|---|---|---|
| 148 | phenyl | —$CH_2$— | —$CH_2$-(4-n-butyloxy-phenyl) | N | —$NH(CH_2)_2$— | —$NHC(=NH)NH_2$ |
| 149 | 4-chloro-phenyl | —$CH_2$— | —$CH_2$-phenyl | N | —$NH(CH_2)_2$— | —$NHC(=NH)NH_2$ |
| 150 | 4-chloro-phenyl | —$CH_2$— | —$CH_2$-furan-3-yl | N | —$NH(CH_2)_2$— | —$NHC(=NH)NH_2$ |
| 151 | 4-fluoro-phenyl | —$CH_2$— | —$CH_2$-(4-methoxy-phenyl) | N | —$NH(CH_2)_2$— | —$NHC(=NH)NHC(=O)$methyl |
| 152 | 4-fluoro-phenyl | —$CH_2$— | —$CH_2$-(4-methoxy-phenyl) | N | —$NH(CH_2)_2$— | —$NHC(=NH)NH$(allyl) |
| 153 | 4-fluoro-phenyl | —$CH_2$— | —$CH_2$-(4-methoxy-phenyl) | N | —$NH(CH_2)_2$— | —$NHC(=NH)NH$(i-propyl) |
| 154 | 4-fluoro-phenyl | —$CH_2$— | —$CH_2$-(4-methoxy-phenyl) | N | —$NH(CH_2)_2$— | —$NHC(=NH)NH$(n-propyl) |
| 155 | 4-fluoro-phenyl | —$CH_2$— | —$CH_2$-(4-methoxy-phenyl) | N | —$NH(CH_2)_2$— | —$NHC(=NH)NH$(ethyl) |
| 156 | 4-fluoro-phenyl | —$CH_2$— | —$CH_2$-(4-methoxy-phenyl) | N | —$NH(CH_2)_2$— | —$NHC(=NH)NH$(methyl) |
| 157 | 4-methoxy-phenyl | —$CH_2$— | —$CH_2$-(4-methoxy-phenyl) | CH | —$C(=O)NH(CH_2)_2$— | —$NHC(=NH)NH_2$ |
| 158 | 4-methoxy-phenyl | —$CH_2$— | —$CH_2$-(4-methoxy-phenyl) | CH | —$O(CH_2)_2$— | —$NHC(=NH)NH_2$ |
| 159 | 4-methoxy-phenyl | —$CH_2$— | —$CH_2$-(4-methoxy-phenyl) | CH | —$S(CH_2)_2$— | —$NHC(=NH)NH_2$ |
| 160 | 4-methoxy-phenyl | —$CH_2$— | —$CH_2$-(4-methoxy-phenyl) | CH | —$(CH_2)_3$— | —$NHC(=NH)NH_2$ |

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

Even though the compounds of the present invention (including their pharmaceutically acceptable salts and pharmaceutically acceptable solvates) can be administered alone, they will generally be administered in admixture with a pharmaceutical carrier, excipient, or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavouring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

A therapeutically effective amount for use of the instant compounds or a pharmaceutical composition thereof comprises a dose range of from about 0.001 mg to about 1,000 mg, in particular from about 0.1 mg to about 500 mg or, more particularly from about 1 mg to about 250 mg of active ingredient per day for an average (70 kg) human.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as prokineticin receptor antagonists is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

As antagonists of a Prokineticin 1 receptor, the compounds of Formula (I) are useful in methods for treating or preventing a disease or condition in a mammal which disease or condition is affected by the antagonistic activity of one or more Prokineticin 1 receptors. Such methods comprise administering to a mammal in need of such treatment or prevention a therapeutically effective amount of a compound, salt or solvate of Formula (I). The compounds of Formula (I) are useful in methods for preventing or treating gastrointestinal (GI) diseases, cancers of the GI tract and reproductive organs, and pain. Examples of GI diseases to be within the scope of the present invention include, but are not limited to: irritable bowel syndrome (IBS, including diarrhea-predominant, as well as alternating diarrhea/constipation forms of IBS), inflammatory bowel disease (IBD, including ulcerative colitis, and Crohn's disease), and GERD and secretory bowel disorders induced by pathogens. Examples of cancers within the scope of the present invention include, but are not limited to, testicular cancer, ovarian cancer, Leydig cell carcinoma, and cancers of the small or large bowel. An example of pain to be covered within the scope of the present invention, is, but not restricted to, visceral hyperalgesia often associated with IBS and IBD.

While the present invention comprises compositions comprising one or more of the compounds of Formula (I) the present invention also comprises compositions comprising intermediates used in the manufacture of compounds of Formula (I).

Representative IUPAC names for the compounds of the present invention were derived using the ACD/LABS SOFTWARE™ Index Name Pro Version 4.5 nomenclature software program provided by Advanced Chemistry Development, Inc., Toronto, Ontario, Canada.

Abbreviations used in the instant specification, particularly the Schemes and Examples, are as follows:
Boc=tert-butoxycarbonyl
BuLi=n-butyllithium
Cpd or Cmpd=compound
d=day/days
DCM=dichloromethane
DIAD=diisopropyl azodicarboxylate
DIPEA or DIEA=diisopropylethylamine
DMEM=Dulbecco's Modified Eagle Medium
DMF=N,N-dimethylformamide
DMSO=dimethylsulfoxide
EDCl=1-(3-Dimethylaminopropyl)-3-ethylcarbodiimide hydrochloride
EtOAc=ethyl acetate
EtOH=ethanol
h=hour/hours
HBTU O-Benzotriazol-1-yl-N,N,N',N'-tetramethyluronium hexafluorophosphate
LDA=lithium diisopropyamide
M=molar
MeCN=acetonitrile
MeOH=methanol
min=minutes
NaOMe=sodium methoxide
PyBOP=benzotriazole-1-yl-oxy-tris-pyrrolidino-phosphonium hexafluorophosphate
rt/RT=room temperature
THF=tetrahydrofuran
TFA=trifluoroacetic acid General Schemes Representative compounds of the present invention can be synthesized in accordance with the general synthetic methods described below and are illustrated in the schemes that follows. The starting materials and reagents used in the schemes that follow are understood to be either commercially available or prepared by methods known to those skilled in the art. Since the schemes are an illustration, the invention should not be construed as being limited by the chemical reactions and conditions expressed.

Scheme A illustrates the general synthesis of compounds of the present invention wherein $L_2$ is other than —NHC(=O)—(CH$_2$)$_{1-4}$—, —C(=O)NH(CR$^y$R$^z$)$_{2-5}$—, and —X$_2$—(CH$_2$)$_{0-4}$—. In Scheme A, $X_1$ of $L_2$ is NH. A compound of formula A1 may be methylated with a methylating agent such as methyl iodide in a polar solvent such as methanol to give a compound of formula A2. A compound of formula A2 may be condensed with an appropriately substituted isocyanate such as N-chlorocarbonyl isocyanate in the presence of excess tertiary amine such as diisopropylethylamine to give a triazine of formula A3.

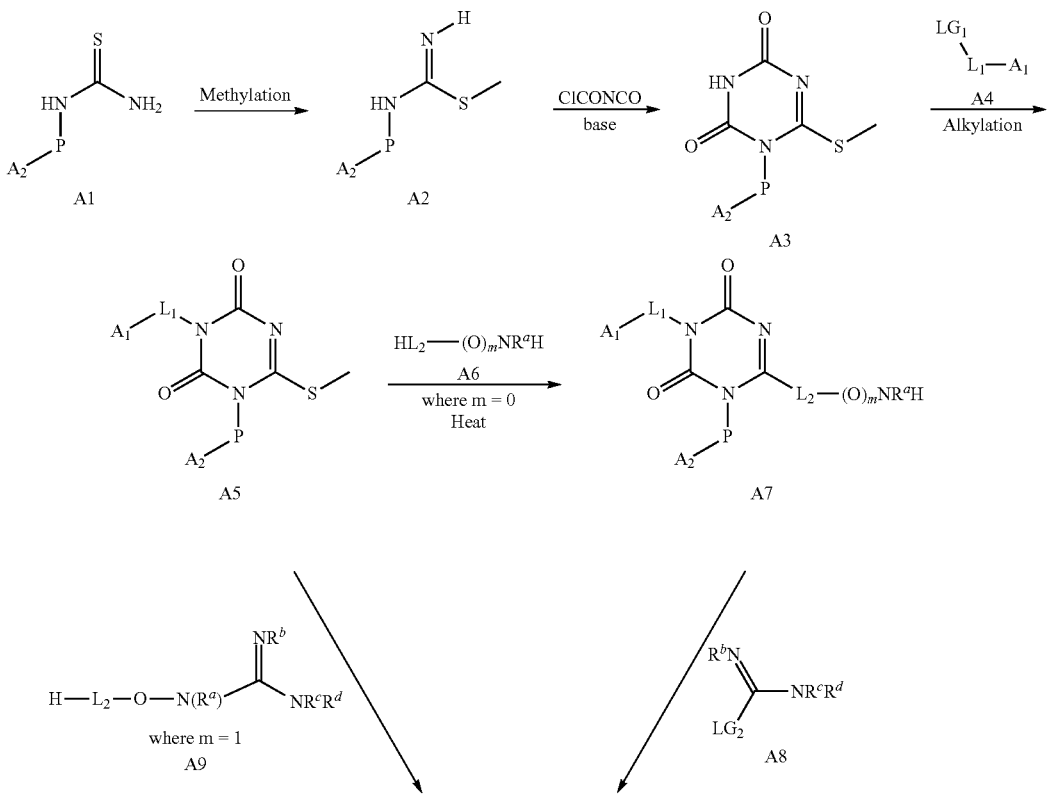

-continued

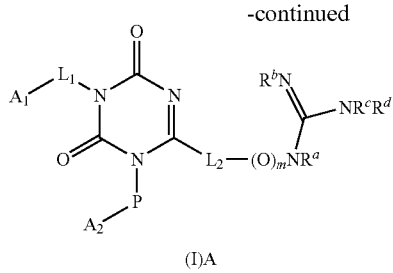

(I)A

A compound of formula A3 may be alkylated with a compound of formula A4, wherein $LG_1$ is a leaving group, using conventional chemistry known to one versed in the art. For instance, when $LG_1$ is a hydroxy group, compound A4 may be coupled with compound A3 with the aid of a coupling agent such as DIAD in the presence of triphenylphosphine in a non-alcoholic polar solvent such as THF or methylene chloride. Alternatively, $LG_1$ may be a halide, tosylate, or the like such that $LG_1$ is displaced by the amino portion of a compound of A3 to give a compound of formula A5.

A compound of formula A5 may be further elaborated by nucleophilic substitution with a compound of formula A6 (wherein $X_1$ is NH and m is zero) to provide a compound of formula A7. One versed in the art will recognize that when $L_2$ is asymmetrical, a nitrogen-protecting group may be necessary to avoid competing reactions. A G-substituent of Formula (I) may be installed by treatment of the terminal amine of a compound of formula A7 with an activated amidine of formula A8 wherein $LG_2$ is a leaving group such as a halide, an alkoxide, an imidazole or pyrazole, an activated alkoxide, or the like, to give compound IA of Formula (I) wherein m is zero. Alternatively, when m is equal to one, an oxy-guanidine substituent may be incorporated by treatment of a compound of formula A7 with a compound of formula A9 to form a compound (I)A of Formula (I) wherein m is one.

Scheme B illustrates the general synthesis of compounds of the present invention wherein $L_2$ is —NHC(=O)—$(CH_2)_{1-4}$—. A compound of formula A5 may be converted to its corresponding amine by treatment with ammonia, or other source of ammonia such as ammonium hydroxide, to give a compound of formula B1. The amino group of a compound B1 may be acylated using conventional chemistry with a compound of formula B2, wherein $LG_3$ is a leaving group such as a halide when B2 is an acid chloride, a hydroxy group when B2 is a carboxylic acid, an alkylcarboxylate when B2 is an anhydride, or an imidazole when B2 is an acylimidazole. Alternatively, B2 may be an activated ester or the like. The K substituent of compounds of formula B2 is either a leaving group $LG_1$ as defined herein, or K is an $R^a$-substituted amino group protected with an appropriate amino-protecting group (PG).

Scheme B

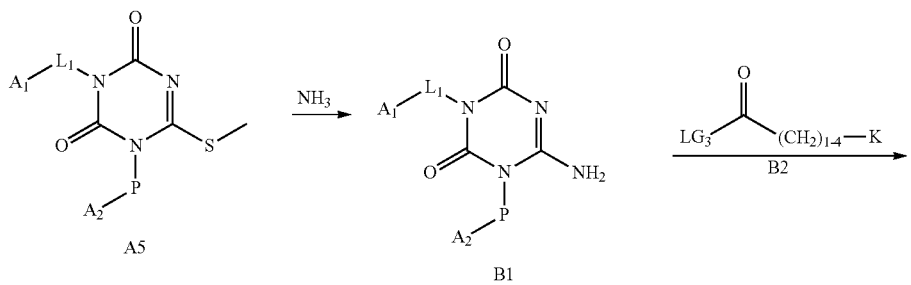

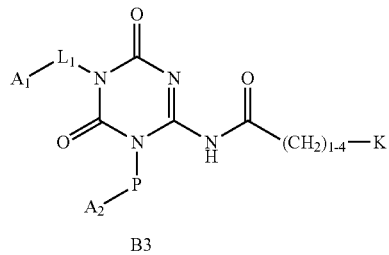

B3

| When K = $LG_1$ | When K = |
|---|---|
| Substitution with $H_2NR^a$ | —$NR^a$(PG) N-Deprotection |

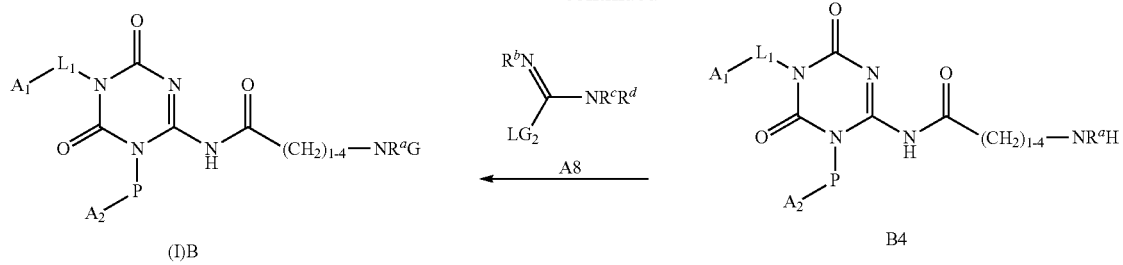

To prepare a compound of formula B4, a compound of formula B3 may either be N-deprotected (when K is —NR$^a$(PG)) using reagents and methods known to one versed in the art, or may undergo a nucleophilic displacement with amine H$_2$NR$^a$ (when K is a LG$_1$). The resulting amine of formula B4 may then be treated with an activated amidine of formula A8 to give a compound (I)B of Formula (I).

Scheme C describes the general synthesis of compounds of the present invention wherein X$_1$ of L$_2$ is a direct bond and L$_2$ is any of those which contains X$_1$. A compound of formula C1 may be condensed with an isocyanate of formula C2 to give a compound of formula C3 which, upon heating, affords a triazine of formula C4. The amino group of a compound of formula C4 may be appropriately substituted using an alkylating agent of formula C5 to afford a compound of formula C6. A G-substituent may be introduced into a compound of formula C6 using the methods described herein to provide a compound (I)C of Formula (I).

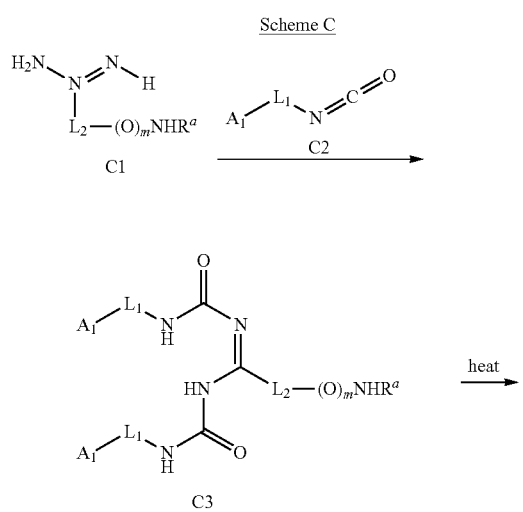

Scheme D illustrates the general synthesis of compounds of the present invention wherein W is C(R$_w$), L$_2$ is other than —NHC(=O)—(CH$_2$)$_{1-4}$— or —C(=O)NH(CR$^y$R$^z$)$_{2-5}$—, and X$_1$ of L$_2$ is NH, O, or S. A compound of formula D1 may be condensed with a compound of formula D2 with heating (wherein LG$_2$ is C$_{1-4}$alkoxy, choro, or the like) to form a compound of formula D3. A compound of formula D3 may then be treated with phosphorus oxychloride, PCl$_5$, or the like and heat to afford a compound of formula D4; alternatively, the bromo analog may be used in this synthetic sequence, which is prepared from D3 using phosphorus oxybromide in place of phosphorus oxychloride. A compound of formula C5 may be used to install —P-A$_2$ via conventional alkylation procedures. A compound of formula D5 may be elaborated via a nucleophilic displacement of the chloride or bromide with a compound of Formula D5a (wherein X$_1$ is NH, O, or S) to afford a compound of formula D6. Further elaboration using the chemistry described herein may be employed to provide compound (I)D of Formula (I).

Scheme D

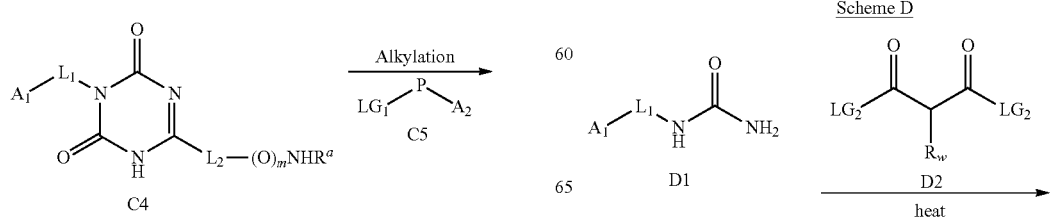

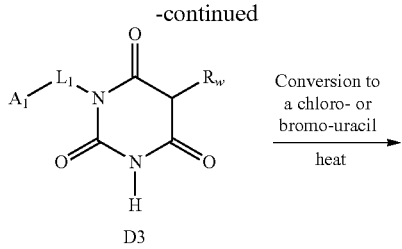

D3

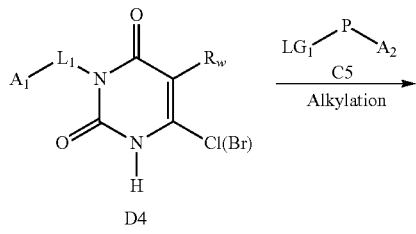

D4

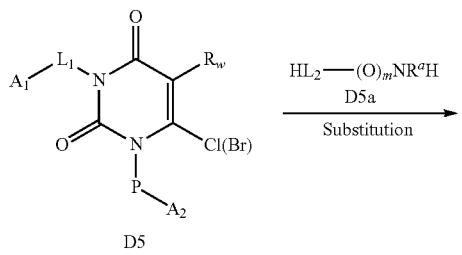

D5

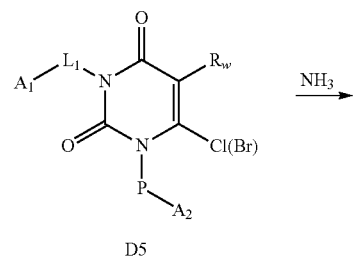

D5

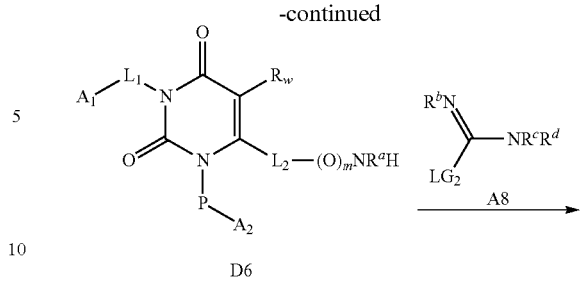

D6

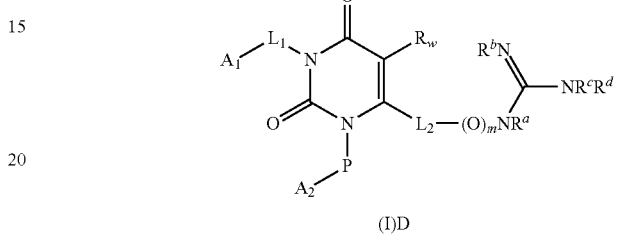

(I)D

Scheme E illustrates the general synthesis of compounds of the present invention wherein W is $C(R_W)$ and $L_2$ is —NHC(=O)—$(CH_2)_{1-4}$—. A compound of formula D5 may be treated with ammonia or other source of ammonia such as ammonium hydroxide to afford the corresponding amino compound of formula E1. The amino group may be acylated with a compound of formula B2 and further elaborated to a compound (I)E of Formula (I) using the methods described herein.

Scheme E

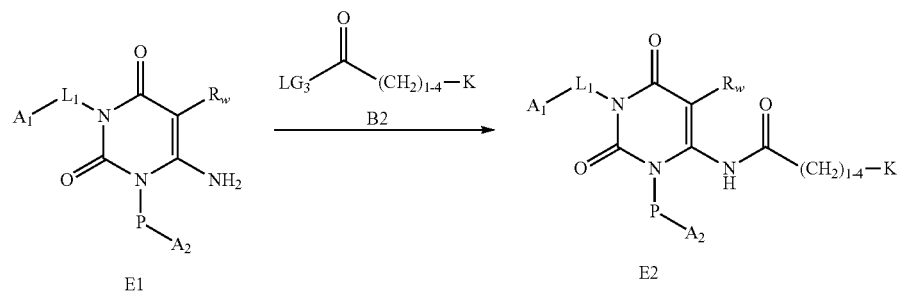

When K = $LG_1$
Substitution with $H_2NR^a$

When K = —$NR^a$(PG)
N-Deprotection

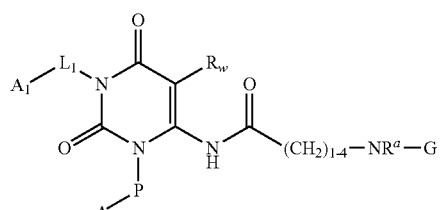

(I)E

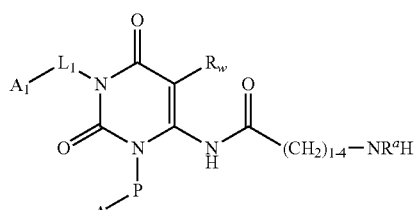

E3

Scheme F illustrates the general synthesis of compounds of the present invention wherein W is $C(R_w)$, $X_1$ of $L_2$ is a direct bond and $L_2$ is any one of those which includes $X_1$. A compound of formula F1 may be condensed with a compound of formula F2 under basic conditions in the presence of a lower alkyl alcohol to form a compound of formula F3. A compound of formula F3 may be condensed with a urea of formula F4 to form a cyclic compound of formula F5.

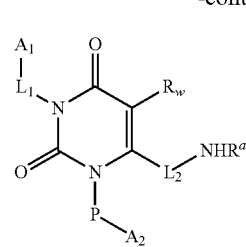

F7

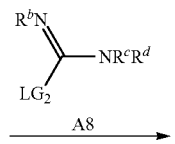

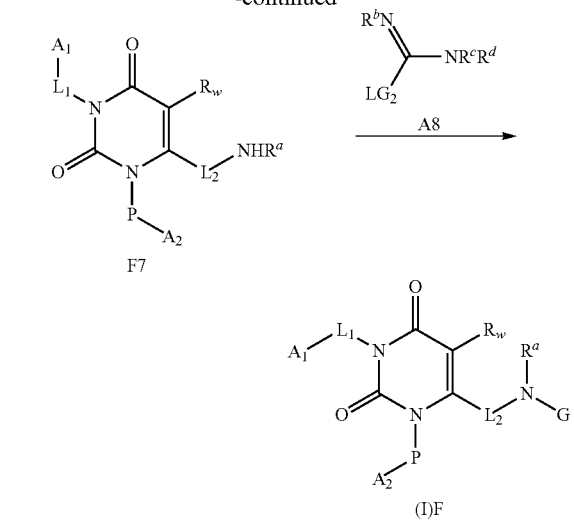

(I)F

A compound of formula F5 may be alkylated with an alkylating agent C5 using conventional chemistry known to one versed in the art to prepare a compound of formula F6. A nucleophilic displacement of $LG_1$ with amine $H_2NR^a$ affords a compound of formula F7, which may be further elaborated to include a G-substituent using the methods described herein to give a compound (I)F of Formula (I).

Scheme G illustrates the general synthesis of compounds of the present invention wherein W is N and $L_2$ is $-X_2-(CH_2)_{0-4}-$. A compound of formula G1 (either commercially available or prepared by known methods described in the scientific literature) may be treated with a base followed by alkylation with a compound of formula A4 to afford a compound of formula G2. Treatment of a compound of formula G2 with an aqueous base such as sodium hydroxide gives a compound of formula G3, which upon treatment with ammonia or its equivalent provides a compound of formula G4. The compound of formula G4 may then be condensed with a compound of formula G5 to form a triazine compound of formula G6.

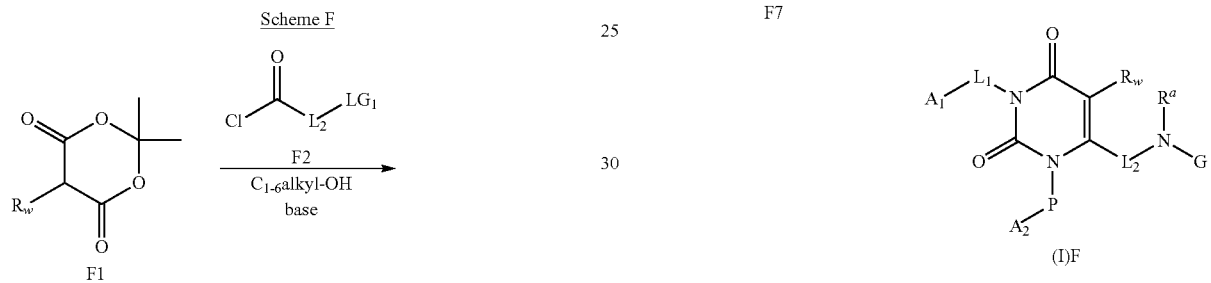

Scheme F

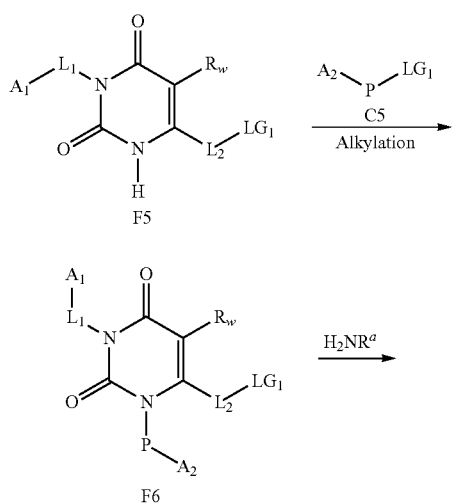

Scheme G

G1

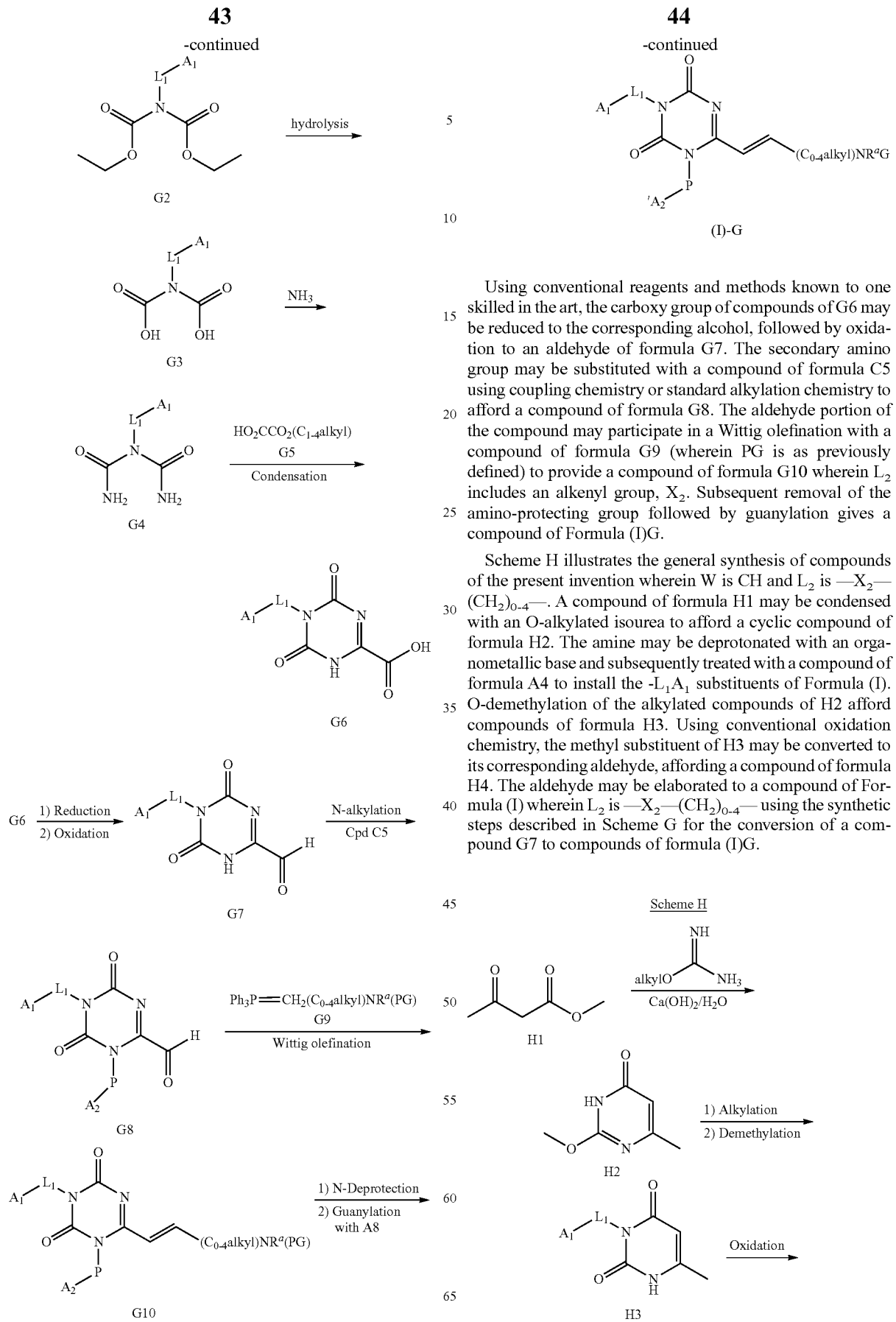

Using conventional reagents and methods known to one skilled in the art, the carboxy group of compounds of G6 may be reduced to the corresponding alcohol, followed by oxidation to an aldehyde of formula G7. The secondary amino group may be substituted with a compound of formula C5 using coupling chemistry or standard alkylation chemistry to afford a compound of formula G8. The aldehyde portion of the compound may participate in a Wittig olefination with a compound of formula G9 (wherein PG is as previously defined) to provide a compound of formula G10 wherein $L_2$ includes an alkenyl group, $X_2$. Subsequent removal of the amino-protecting group followed by guanylation gives a compound of Formula (I)G.

Scheme H illustrates the general synthesis of compounds of the present invention wherein W is CH and $L_2$ is —$X_2$—$(CH_2)_{0-4}$—. A compound of formula H1 may be condensed with an O-alkylated isourea to afford a cyclic compound of formula H2. The amine may be deprotonated with an organometallic base and subsequently treated with a compound of formula A4 to install the -$L_1A_1$ substituents of Formula (I). O-demethylation of the alkylated compounds of H2 afford compounds of formula H3. Using conventional oxidation chemistry, the methyl substituent of H3 may be converted to its corresponding aldehyde, affording a compound of formula H4. The aldehyde may be elaborated to a compound of Formula (I) wherein $L_2$ is —$X_2$—$(CH_2)_{0-4}$— using the synthetic steps described in Scheme G for the conversion of a compound G7 to compounds of formula (I)G.

-continued

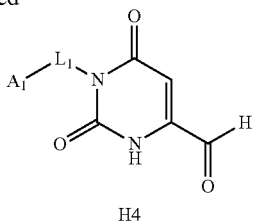

H4

Scheme I depicts the general synthesis of compounds of the present invention wherein $L_2$ of Formula (I) is one which contains an $X_1$ group, and W is N. In Scheme I, $X_1$ is S.

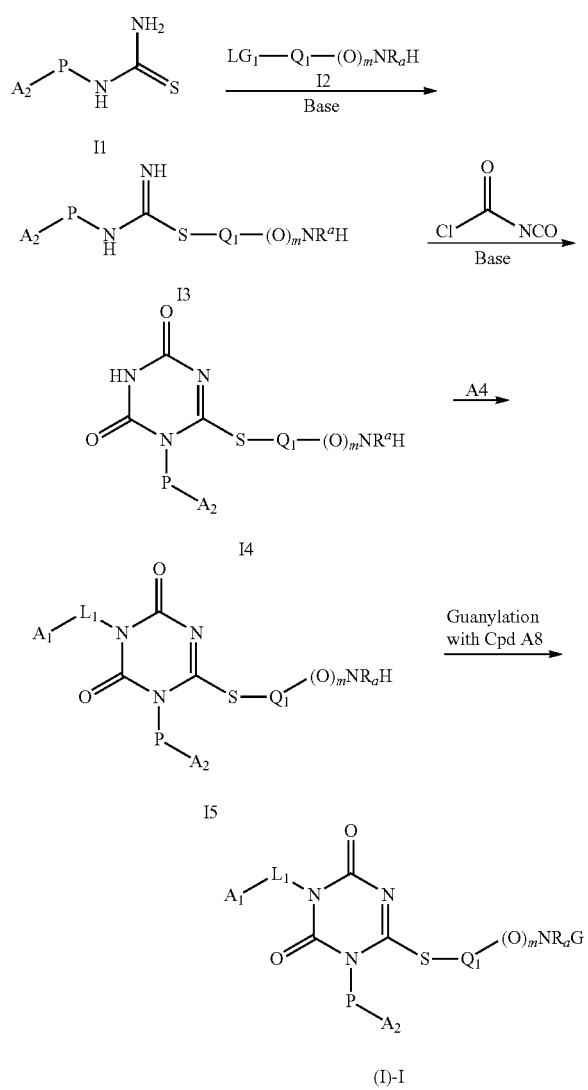

A compound of formula I1 (either commercially available or prepared by known methods described in the scientific literature) may be alkylated under basic conditions with a compound of formula I2 (wherein $Q_1$ is —$(CH_2)_u$—$X_2$—$(CH_2)_v$—, —$(CH_2)_{2-3}$—$X_3$—$(CH_2)_{2-3}$—, or —$CH(R^x)$—

$(CR^yR^z)_{1-5}$—) to provide a compound of formula I3. A compound of formula I3 may be condensed with an appropriately substituted isocyanate such as N-chlorocarbonyl isocyanate in the presence of excess tertiary amine such as diisopropylethylamine to give a triazine of formula I4. A compound of formula I4 may be alkylated with a compound of formula A4 to provide a compound of formula I5, which may then be guanylated according the methods described herein to provide a compound of formula (I)-I.

Scheme J illustrates the general synthesis of compounds of the present invention wherein $L_2$ is —C(=O)NH($CR^yR^z$)$_{2-5}$— and W is N.

Scheme J

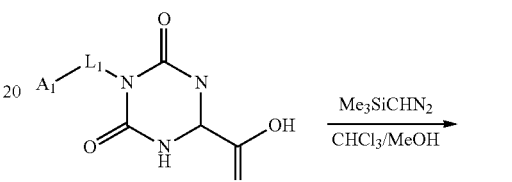

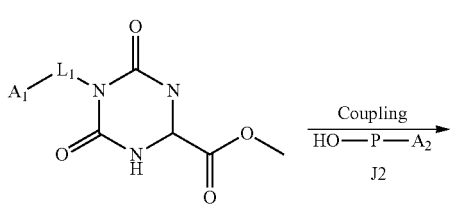

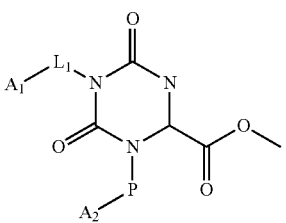

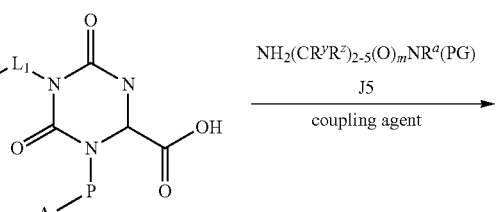

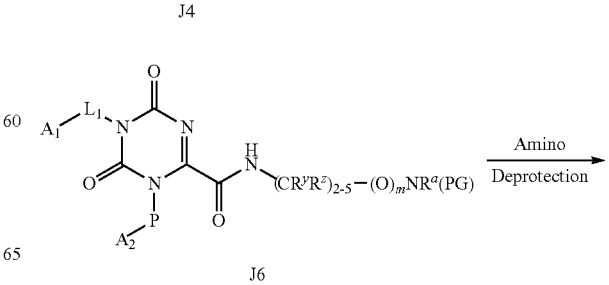

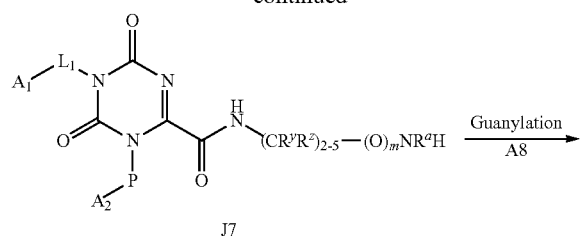

J7

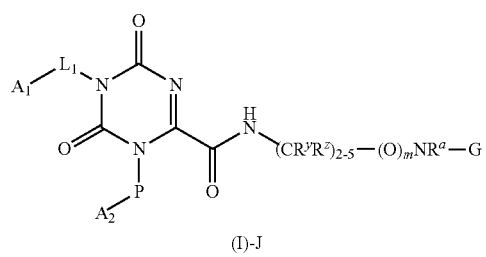

(I)-J

A compound of Formula G6 may be treated with a methylating agent such as trimethylsilyl diazomethane to give the methyl ester of formula J1. Under Mitsunobu type coupling conditions (in the presence of a coupling agent, activating agent), an alcohol of formula J2 may be coupled with the secondary amine of a compound of formula J1 to afford a compound of formula J3. Standard base hydrolysis of the methyl ester gives a compound of formula J4, wherein the corresponding carboxylic acid may be coupled with an amine of formula J5 (PG is an appropriate amino protecting group) to afford a compound of formula J6. Standard removal of the amino protecting group, PG, yields the primary amine of formula J7, which may be guanylated according to the methods described herein to yield a compound of formula (I)-J.

Scheme K illustrates the general synthesis of compounds of the present invention wherein $L_2$ is —C(=O)NH(CR$^y$R$^z$)$_{2-5}$— and W is CH.

Scheme K

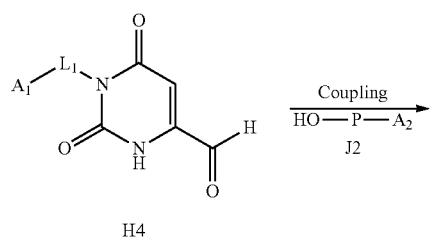

H4

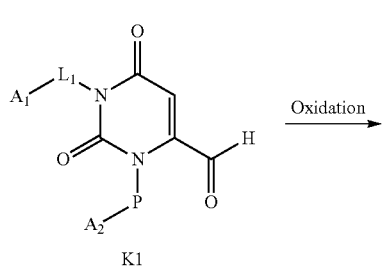

K1

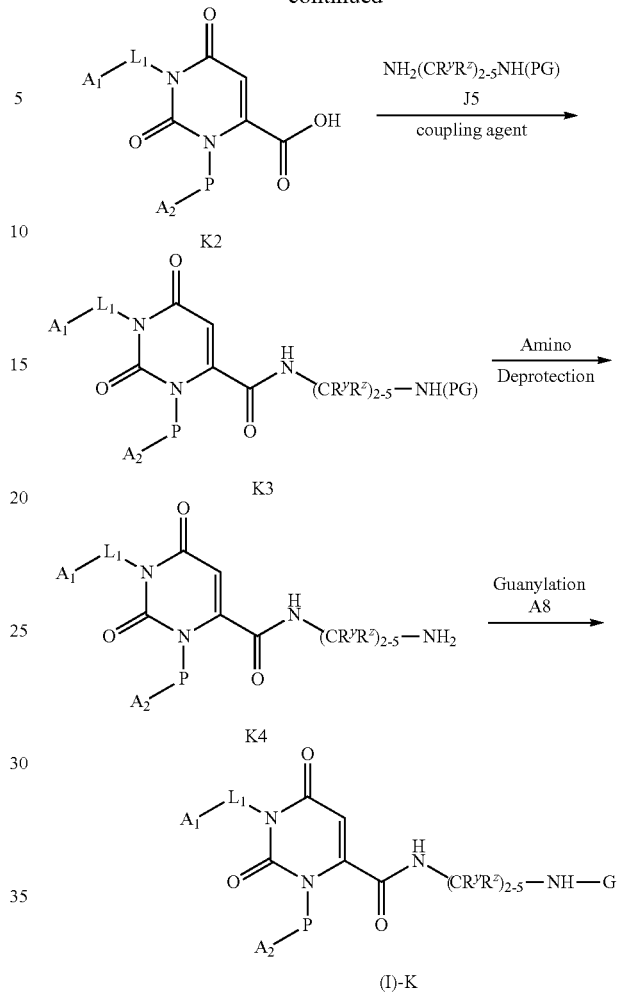

A compound of formula H4 may be treated under Mitsunobu-type coupling conditions (in the presence of a coupling agent and activating agent), with an alcohol of formula J2 to afford a compound of formula K1. Oxidation of the aldehyde group using an appropriate oxidizing agent gives a compound of formula K2, wherein the corresponding carboxylic acid may be coupled with an amine of formula J5 (PG is an appropriate amino protecting group) to afford a compound of formula K3. The conventional removal of the amino protecting group, PG, yields the primary amine of formula K4, which may be guanylated according to the methods described herein to yield a compound of formula (I)-K.

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The instant compounds may also be used as intermediates in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Reagents were purchased from commercial sources. Nuclear magnetic resonance (NMR) spectra for hydrogen atoms were measured in the indicated solvent with (TMS) as the internal standard on a Bruker-Biospin Inc. DRX 500 (500 MHz) or DPX 300 (300 MHz) spectrometer. The values are expressed in parts per million downfield from TMS. The mass spectra (MS) were determined on a Micromass Platform LC spectrometer, an Agilent LC spectrometer or a Micromass LCT spectrometer using electrospray techniques. Microwave accelerated reactions were performed using a CEM Discover microwave instrument, and were contained in a sealed pressure vessel unless otherwise noted. Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Example 1

N-{2-[5-(4-Ethyl-benzyl)-1-(4-methoxy-benzyl)-4,6-dioxo-1,4,5,6-tetrahydro-[1,3,5]triazin-2-ylamino]-ethyl}-guanidine (Cpd 46)

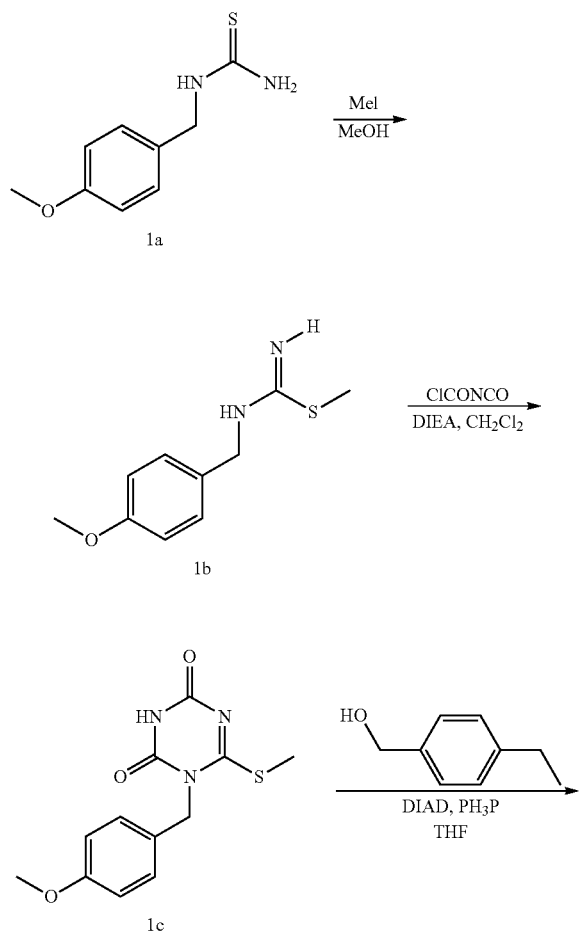

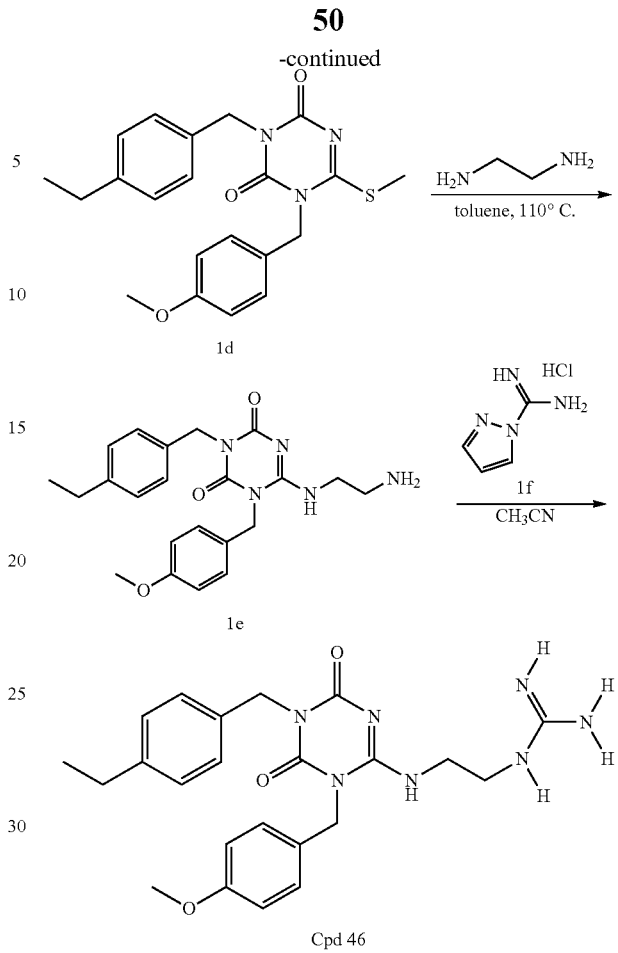

A. 1-(4-Methoxy-benzyl)-6-methylsulfanyl-1H-[1,3,5]triazine-2,4-dione (Cpd_1c). To (4-methoxy-benzyl)thiourea (2.00 g, 10.1 mmol) in MeOH (40 mL) was added methyl iodide (0.64 mL, 10.1 mmol). The reaction was stirred at room temperature for 24 h. The reaction mixture was concentrated to yield 2.00 g of crude compound (1b) that was used in the next step without further purification.

B. To Compound 1b (3.6 g, 17.1 mmol) in methylene chloride (40 mL) was added excess diisopropylethylamine (6.61 g, 51.3 mmol). The reaction mixture was cooled to 0° C. A portion of N-chlorocarbonyl isocyanate (1.78 g, 17.1 mmol) was added dropwise. The reaction mixture was allowed to slowly warm to room temperature. After 24 h, water was added and the reaction mixture was extracted with ethyl acetate. The phases were separated, and the organic layer was dried over sodium sulfate, filtered, and concentrated. Methanol was added to the crude product, and the solid was collected by vacuum filtration to give compound 1c (1.5 g). $^1$H NMR (DMSO-$d_6$) δ 2.45 (3H, s), 3.73 (3H, s), 4.98 (2H, s), 6.89-6.92 (2H, d, J=8.5 Hz), 7.22-7.25 (2H, d, J=8.5 Hz), 11.58 (1H, s).

C. 3-(4-Ethyl-benzyl)-1-(4-methoxy-benzyl)-6-methylsulfanyl-1H-[1,3,5]triazine-2,4-dione (Cpd 1d). To Cpd 1c (0.1 g, 0.35 mmol) in tetrahydrofuran was added 4-ethylbenzyl alcohol (0.049 g, 0.35 mmol), triphenylphosphine (0.19 g 0.71 mmol) and diisopropyl azodicarboxylate (0.087 g, 0.43 mmol). The reaction stirred at room temperature for 64 h. The reaction mixture was taken up in ethyl acetate, washed with water, and the phases were separated. The organic layer was dried over sodium sulfate, filtered, and concentrated. The resulting material was purified by normal phase chromatography using an ISCO automated system to give Cpd 1d (0.14 g) as a white solid.

D. 6-(2-Amino-ethylamino)-3-(4-ethyl-benzyl)-1-(4-methoxy-benzyl)-1H-[1,3,5]triazine-2,4-dione (Cpd 1e). To 1-(4-methoxy-benzyl)-6-methylsulfanyl-1H-[1,3,5]triazine-2,4-dione (0.14 g, 0.33 mmol) in toluene was added excess ethylenediamine (0.10 g, 1.76 mmol). The reaction mixture was heated at 110° C. for 18 h. The reaction mixture was cooled to room temperature, diluted with water and extracted with ethyl acetate. The phases were separated and the organic layer was dried over sodium sulfate, filtered and concentrated. The resultant Cpd 1e (0.11 g) was used in the next step without further purification.

E. N-{2-[5-(4-Ethyl-benzyl)-1-(4-methoxy-benzyl)-4,6-dioxo-1,4,5,6-tetrahydro-[1,3,5]triazin-2-ylamino]-ethyl}-guanidine (Cpd 46). To a mixture of Cpd 1e (0.11 g, 0.26 mmol) in acetonitrile (4 mL) was added excess diisopropylamine (0.069 g, 0.53 mmol) and 1H-pyrazolo-1-carboxamidine hydrochloride, Cpd 1f, (0.039 g, 0.26 mmol). The reaction mixture was stirred for 18 h at room temperature. A white solid precipitated from the reaction mixture and was collected by filtration to give the title compound 46 (98% pure by HPLC, 0.0119 g). $^1$H NMR (DMSO-$d_6$) δ 1.01-1.04 (3H, t, J=7.5 Hz), 2.41-2.47 (2H, q, J=7.4 Hz), 3.26-3.16 (4H, m), 3.61 (3H, s), 4.75 (2H, s), 4.93 (2H, s), 6.77-6.79 (2H, d, J=8.64 Hz), 7.00-7.12 (6H, m), 7.55 (1H, m), 8.06 (1H, m).

Using the procedures of Example 1 and the appropriate reagents, starting materials and purification methods known to those skilled in the art, the following compounds of the present invention were prepared: compounds 39, 45, 77, 78, 79, 80, 82, 83, 109, 111, 112, 123, 124, 131, 136, 137, 145, and 146.

Example 2

N-{2-[5-(4-Fluoro-benzyl)-1-(4-methoxy-benzyl)-4,6-dioxo-1,4,5,6-tetrahydro-[1,3,5]triazin-2-ylamino]ethyl}-guanidine (Cpd 17)

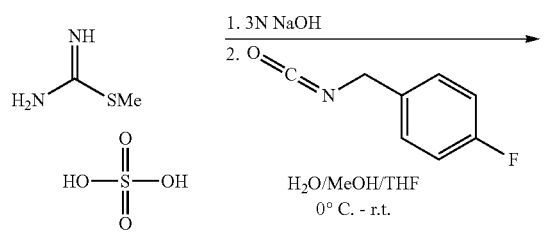

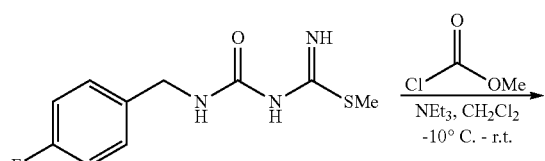

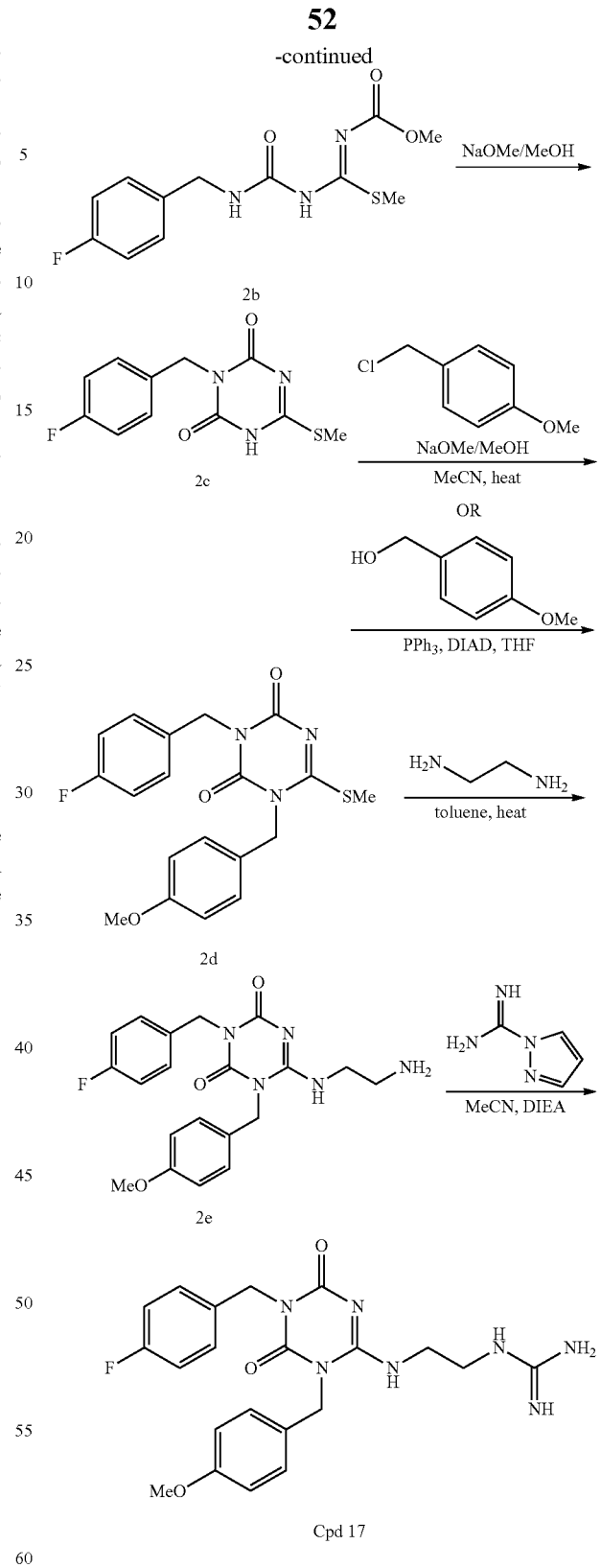

A. ((4-Fluorobenzyl)amino)carbonyl)carbamimidothioic acid methyl ester (Cpd 2a). S-methylisothiouronium sulfate (10.0 g, 35.9 mmol) was dissolved in 8:2:1 MeOH/H$_2$O/THF and the mixture was treated with 3 N NaOH (12 mL, 35.9 mmol). The solution was then cooled to 0° C. and 4-fluorobenzyl isocyanate (5.43 g, 35.9 mmol) was added dropwise over 30 min. The reaction was stirred overnight and gradually warmed to room temperature. The mixture was then washed with saturated aqueous NH$_4$Cl and extracted with dichloromethane. The combined organic phases were dried over Na$_2$SO$_4$, filtered and concentrated under reduced pressure. The resultant residue was purified on an Isco flash column (20% EtOAc-100% EtOAc in heptanes), to give Compound 2a (4.1 g) as a white powder.

B. 5-(Methylthio)-3,7-dioxo-1-(4-fluorobenzyl)-2-oxa-4,6,8-triazanon-4-en-9-oic acid methyl ester (Cpd 2b). A solution of Compound 2a (4.1 g, 17.0 mmol) in dichloromethane was treated with triethylamine (3.08 mL, 22.1 mmol) and the mixture was cooled to −10° C. Methyl chloroformate (2.62 mL, 34.0 mmol) was added dropwise via an addition funnel over 15 min and the reaction was allowed to stir for 4 h while gradually warming to room temperature. The solution was then washed with saturated aqueous NH$_4$Cl and extracted with dichloromethane. The combined organic phases were dried over Na$_2$SO$_4$, filtered and concentrated. The resultant residue was purified on an Isco flash column (5% MeOH) to afford Compound 2b (3.63 g) as a white solid.

C. 3-(4-Fluoro-benzyl)-6-methylsulfanyl-1H-[1,3,5]triazine-2,4-dione (Cpd 2c). Compound 2b (3.63 g, 12.1 mmol) was dissolved in MeOH (100 mL) and the solution was treated with NaOMe in MeOH (4.6 M, 2.90 mL, 13.3 mmol) and the reaction was allowed to stir at room temperature for 1 h. A white precipitate formed upon addition of the NaOMe. The reaction mixture was diluted with 1N HCl (50 mL) and the resultant precipitate was collected by filtration. The solid was dried under reduced pressure at 160° C. over xylenes to afford Compound 2c (3.6 g) as its HCl salt.

D. 3-(4-Fluoro-benzyl)-1-(4-methoxy-benzyl)-6-methylsulfanyl-1H-[1,3,5]triazine-2,4-dione (Cpd 2d). Compound 2c (500 mg, 1.65 mmol) was dissolved in THF and was treated with 4-methoxybenzyl alcohol (227 mg, 1.65 mmol), triphenylphospine (866 mg, 3.30 mmol), and diisopropyl azodicarboxylate (334 mg, 1.65 mmol). The reaction was allowed to stir overnight at room temperature. After monitoring the reaction via HPLC, the solution was partitioned between water and ethyl acetate. Combined organic layers were dried over anhydrous sodium sulfate, filtered and reduced. The crude mixture was purified via Isco flash column (20% ethyl acetate-100% ethyl acetate in heptanes, 40 min) to afford 390 mg of Cpd 2d as a white solid. $^1$H NMR (DMSO, d$_6$). δ 3.29 (s, 3H), 3.74 (s, 3H), 4.93 (s, 2H), 5.03 (s, 2H), 6.89-6.92 (d, 2H, J=8.62), 7.12-7.36 (m, 4H), 7.38-7.41 (m, 2H).

E. 4-[3-(3,4-Dichloro-benzyl)-6-methylsulfanyl-2,4-dioxo-3,4-dihydro-2H-[1,3,5]triazin-1-ylmethyl]-benzamide (Cpd 2d). Compound 2c (dichorobenzyl) (200 mg, 0.56 mmol) was dissolved in MeCN and was treated with diisopropylethylamine (0.196 mL, 1.13 mmol) and 4-chloromethyl benzyl chloride (96 mg, 0.56 mmol). The reaction mixture was heated to 80° C. and was allowed to stir overnight. The reaction mixture was washed with saturated aqueous NH$_4$Cl and extracted with ethyl acetate. The combined organic extracts were dried over Na$_2$SO$_4$, filtered and concentrated. The resultant crude mixture was purified by Isco flash column (20%-100% EtOAc in heptanes, 40 min) to afford 70 mg of Cpd 2d as a white powder.

F. 6-(2-Amino-ethylamino)-3-(4-fluoro-benzyl)-1-(4-methoxy-benzyl)-1H-[1,3,5]triazine-2,4-dione (Cpd 2e). A solution of Compound 2d (390 mg, 1.01 mmol) in toluene (8 mL) and was treated with ethylenediamine (302 mg, 5.03 mmol). The reaction was heated to 90° C. and was allowed to stir overnight. The mixture was then partitioned between water and ethyl acetate. The combined organic layers were dried over Na$_2$SO$_4$, filtered and reduced. Reduction provided 390 mg of Cpd 2e as a crude mixture. The crude compound was used in further synthesis without additional purification.

G. N-{2-[5-(4-Fluoro-benzyl)-1-(4-methoxy-benzyl)-4,6-dioxo-1,4,5,6-tetrahydro-[1,3,5]triazin-2-ylamino]-ethyl}-guanidine (Cpd 17). A crude mixture of Cpd 2e (390 mg, 0.98 mmol) was dissolved in acetonitrile (10 mL) and was treated with pyrazole-1-carboxamidine hydrochloride (143 mg, 0.98 mmol) and diisopropylethylamine (0.340 mL, 1.95 mmol). The reaction was allowed to proceed overnight at room temperature. Inspection of the reaction mixture showed that a white precipitate had formed and the precipitate was collected and dried by vacuum filtration. The solid collected afforded 307 mg of Cpd 17 as a white powder. M$^+$ (ES+) =442.3. $^1$H NMR (DMSO, d$_6$). δ 3.33 (m, 4H), 3.73 (s, 3H), 4.89 (s, 2H), 5.04 (s, 2H), 6.89-6.91 (d, 2H, J=8.66 Hz), 7.10-7.16 (t, 2H, J=8.91 Hz), 7.21-7.24 (d, 2H, J=8.63 Hz), 7.32-7.36 (dd, 2H, J=2.90, 5.57 Hz), 7.66 (s, 1H), 8.19 (s, 1H).

Using the procedures of Example 2 and the appropriate reagents, starting materials and purification methods known to those skilled in the art, the following compounds of the present invention were prepared: compounds 1, 2, 3, 4, 5, 6, 7, 8, 9, 11, 12, 13, 14, 15, 16, 18, 19, 20, 21, 22, 23, 24, 25, 25, 29, 30, 31, 32, 33, 34, 35, 36, 37, 38, 40, 41, 50, 51, 52, 57, 68, 69, 85, 86, 87, 129, 130, 142, 144, 147, 148, 149, and 150.

Cpd 51: 4-[3-(3,4-Dichlorobenzyl)-6-(2-guanidinoethylamino)-2,4-dioxo-3,4-dihydro-2H-[1,3,5]triazin-1-yl-methyl]-benzamide δ (DMSO, d$_6$) 3.30-3.37 (m, 4H), 4.90 (s, 2H), 5.10 (s, 1H), 7.27-7.32 (m, 3H), 7.51-7.61 (m, 2H), 7.83 (d, 2H, J=9.7 Hz), 7.94 (s, 1H), 8.08 (t, 1H, J=3.7 Hz).

Example 3

N-{2-[1-Benzyl-3-(4-methoxy-benzyl)-2,6-dioxo-1,2,3,6-tetrahydro-pyrimidin-4-ylamino]-ethyl}-guanidine (Cpd 81)

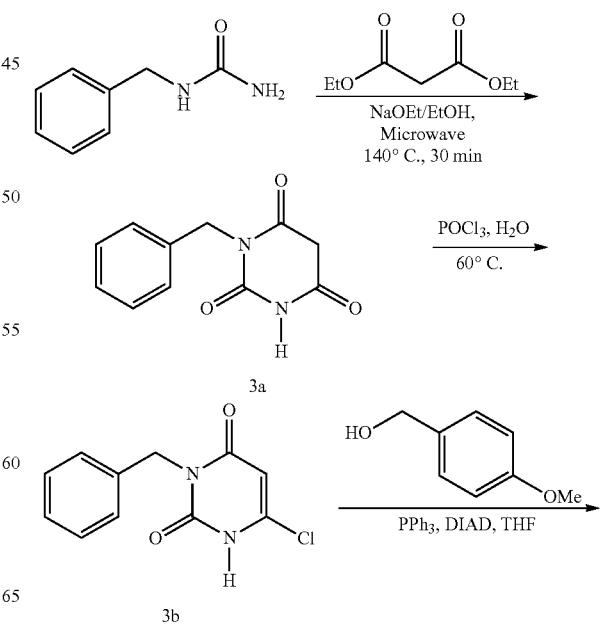

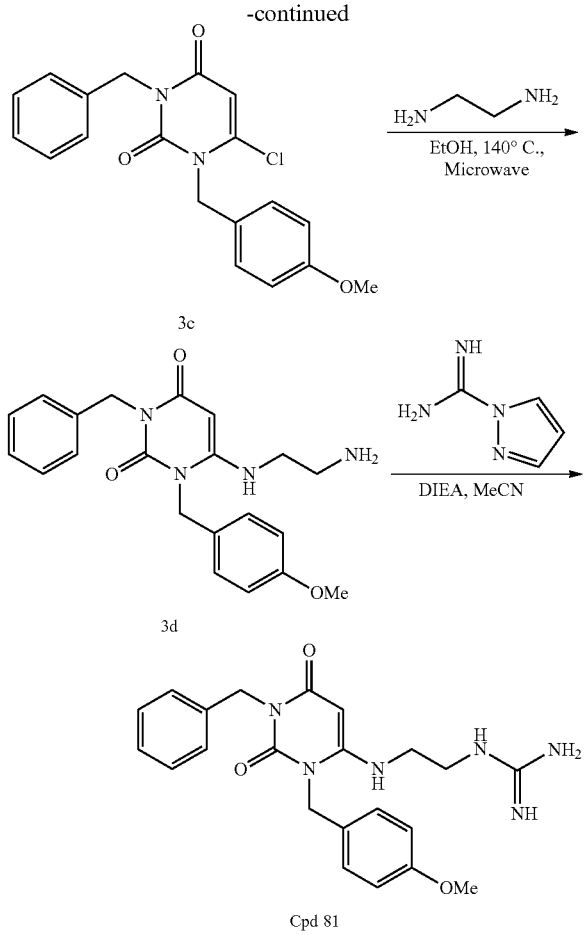

A. 1-Benzyl-pyrimidine-2,4,6-trione (Cpd 3a). N-benzyl urea (500 mg, 3.33 mmol) was dissolved in ethanol (8 mL) and the mixture was treated with diethyl malonate (640 mg, 4.0 mmol) and NaOEt in EtOH (1.29 mL, 3.1M, 4.0 mmol). The reaction was then run under microwave conditions at 140° C. for 30 min. The solution was reduced in vacuo and the residue was triturated with ethanol. The desired compound was collected by vacuum filtration to give Cpd 3a (500 mg) as a white powder. $^1$H NMR (DMSO, $d_6$). δ 3.69 (s, 2H), 4.87 (s, 2H), 7.21-7.31 (m, 5H) 11.41 (s, 1H).

B. 6-Chloro-3-benzyl uracil (Cpd 3b). Cpd 3a (500 mg, 2.29 mmol) was dissolved in phosphorous oxychloride (3.5 mL, 22.9 mmol) and the reaction mixture was cautiously treated with water (0.103 mL, 5.7 mmol). The solution was heated to 60° C. and was stirred overnight. The reaction mixture was then concentrated and the residue was poured over 2N NaOH (15 mL). The crude material was collected by vacuum filtration and purified by recrystallization from ethanol to afford Cpd 3b (60 mg) as a white powder. A second crop of 300 mg of crude 3b was recovered from the recrystallization and used in subsequent reactions without further purification. $^1$H NMR (MeOD, $d_4$). δ 5.04 (s, 2H), 5.87 (s, 1H), 7.25-7.38 (m, 5H).

C. 1-(4-Methoxylbenzyl)-6-chloro-3-benzyl uracil (Cpd 3c). A stirred solution of Cpd 3b (60 mg, 0.25 mmol) in THF was treated with 4-methoxylbenzyl alcohol (35 mg, 0.25 mmol), triphenylphosphine (133 mg, 0.51 mmol) and diiso- propyl azocarboxylate (51 mg, 0.25 mmol). The reaction was allowed to stir overnight at room temperature. The mixture was washed with water and extracted with ethyl acetate. Combined organic extracts were dried over $Na_2SO_4$, filtered and concentrated. The resultant residue was purified by Isco flash column chromatography (20% EtOAc-100 EtOAc in heptanes, 40 min) to afford Cpd 3c (60 mg) as a white powder. M$^+$ (ES+)=356.9.

D. 6-(2-Amino-ethylamino)-3-benzyl-1-(4-methoxybenzyl)-uracil (Cpd 3d). Cpd 3c (60 mg, 0.17 mmol) was dissolved in ethanol (3 mL) and the reaction mixture was treated with ethylenediamine (51 mg, 0.84 mmol). The solution was run at 140° C. for 20 min under power max conditions in a microwave reactor. The solution was washed with water and extracted with ethyl acetate. Combined organic phases were dried over $Na_2SO_4$, filtered and concentrated to give crude Cpd 3d (35 mg) as a yellow oil. The crude mixture was used in subsequent reactions without further purification.

E. N-{2-[1-Benzyl-3-(4-methoxy-benzyl)-2,6-dioxo-1,2,3,6-tetrahydro-pyrimidin-4-ylamino]-ethyl}-guanidine (Cpd 81). The title compound was prepared as described in Example 2, Step G. The crude material was purified by reverse phase preparative HPLC to give the title compound as its TFA salt (8.2 mg). M+ (ES+)=422.9. $^1$H NMR (MeOD, $d_4$). δ 3.19-3.24 (m, 4H), 3.67 (s, 3H), 4.77 (s, 1H), 4.99 (s, 2H), 5.03 (s, 2H), 6.77-6.80 (d, 2H, J=8.79 Hz), 7.01-7.04 (d, 2H, J=8.75 Hz), 7.12-7.25 (m, 5H).

Using the procedures of Example 3 and the appropriate reagents, starting materials and purification methods known to those skilled in the art, the following compounds of the present invention were prepared: compound 84.

Cpd 84: N-{2-[1,3-Bis-(4-methoxy-benzyl)-2,6-dioxo-1,2,3,6-tetrahydro-pyrimidin-4-ylamino]-ethyl}-guanidine (DMSO, $d_6$) δ 3.25-3.27 (m, 2H), 3.35-3.37 (m, 2H), 3.74 (s, 3H), 3.75 (s, 3H), 4.83 (s, 1H), 4.90 (s, 2H), 5.15 (s, 2H), 6.81-6.89 (m, 4H), 7.14-7.24 (m, 4H), 7.70 (s, 1H).

Example 4

N-{2-[5-(4-Fluoro-benzyl)-1-(4-methoxy-benzyl)-4,6-dioxo-1,4,5,6-tetrahydro-[1,3,5]triazin-2-ylamino]-ethyl}-N'-(4-fluoro-phenyl)-guanidine (Cpd 119)

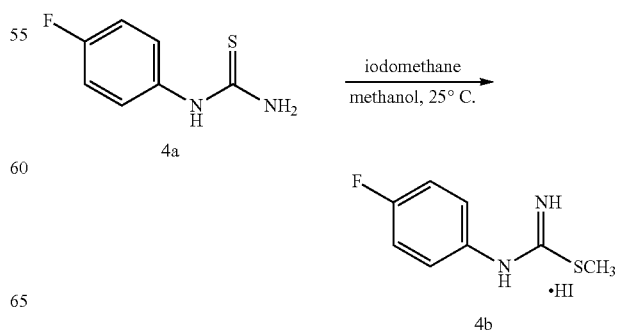

-continued

Cpd 4b $\xrightarrow{\text{Ethanol} \atop 160°\text{C. Microwave}}$

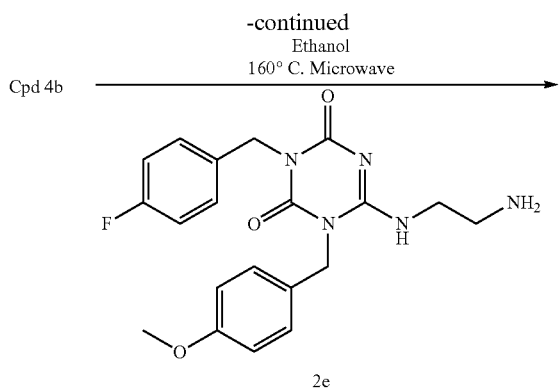

2e

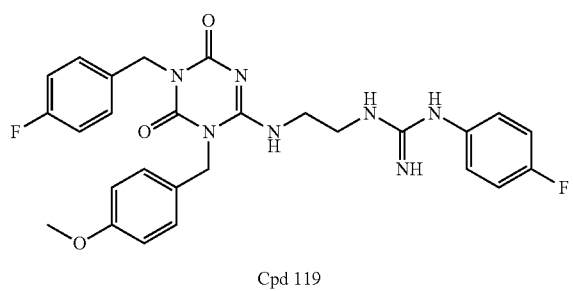

Cpd 119

A. 1-(4-Fluoro-phenyl)-2-methyl-isothiourea (Cpd. 4b). To a solution of (4-Fluoro-phenyl)-thiourea (18.7 mg, 0.11 mmol) and methanol (0.25 mL) was added iodomethane (8 μL, 0.13 mmol). The mixture was stirred at 25° C. for 16 h, then concentrated to a residue to provide crude compound 4b.

C. N-{2-[5-(4-Fluoro-benzyl)-1-(4-methoxy-benzyl)-4,6-dioxo-1,4,5,6-tetrahydro-[1,3,5]triazin-2-ylamino]-ethyl}-N'-(4-fluoro-phenyl)-guanidine (Cpd 127). To a solution of Compound 4b in ethanol (0.5 mL) was added Compound 2e (40 mg, 0.10 mmol). The mixture was irradiated in a microwave reactor at 160° C. for 15 min, then concentrated. The resulting residue was dissolved into dimethylsulfoxide and purified by reversed-phase chromatography to furnish the title compound 119 (18.3 mg, 0.024 mmol) as its TFA salt. $^1$H NMR (methanol-d$_4$): δ 7.42 (m, 2H), 7.24-7.12 (m, 6H), 7.00 (m, 2H), 6.89 (m, 2H), 5.06 (s, 2H), 5.01 (s, 2H), 3.75 (s, 3H), 3.56 (m, 2H), 3.43 (m, 2H); HRMS m/z (M+H)$^+$ calcd 536.2222, found 536.2227.

Using the procedures of Example 4 and the appropriate reagents, starting materials and purification methods known to those skilled in the art, the following compounds of the present invention were prepared: compounds 44, 53, 54, 58, 61, 62, 63, 64, 65, 66, 67, 70, 71, 72, 73, 74, 75, 76, 88, 89, 90, 91, 92, 103, 104, 105, 106, 107, 108, 114, 115, 116, 117, 118, 120, 121, 126, 127, 128, 133, 134, 135, 138, 139, 140, 151, 152, 153, 154, 155, and 156.

Cpd 58: N-{2-[5-(3,4-Dichloro-benzyl)-1-(4-methoxy-benzyl)-4,6-dioxo-1,4,5,6-tetrahydro-[1,3,5]triazin-2-ylamino]-ethyl}-N'-isopropyl-guanidine. $^1$H NMR (methanol-d$_4$): δ 7.56 (s, 1H), 7.45 (d, 1H, J=8.3 Hz), 7.35 (d, 1H, J=8.3 Hz), 7.22 (d, 1H, J=8.3 Hz), 6.89 (d, 2H, J=8.4 Hz), 5.12 (s, 2H), 5.01 (s; 2H), 3.77 (s, 3H), 3.68 (m, 1H), 3.57 (t, 2H, J=6.3 Hz), 3.41 (t, 2H, J=6.3 Hz), 1.17 (d, 6H, J=6.5 Hz); HRMS m/z (M+H)$^+$ calcd 534.1787, found 534.1792.

Cpd 90: N-(4-Cyano-phenyl)-N'-{2-[5-(4-fluoro-benzyl)-1-(4-methoxy-benzyl)-4,6-dioxo-1,4,5,6-tetrahydro-[1,3,5]triazin-2-ylamino]-ethyl}-guanidine. $^1$H NMR (methanol-d$_4$): δ 7.74 (d, 2H, J=8.7 Hz), 7.44 (m, 2H), 7.35 (d, 2H, J=8.3 Hz), 7.21 (d, 2H, J=8.6 Hz), 7.01 (t, 2H, J=8.8 Hz), 6.88 (d, 2H, J=8.8 Hz), 5.11 (s, 2H), 5.02 (s, 2H), 3.75 (s, 3H), 3.61 (t, 2H, J=6.3 Hz), 3.51 (m, 2H); HRMS m/z (M+H)$^+$ calcd 543.2268, found 543.2273.

Cpd 104: N-{2-[5-(4-Fluoro-benzyl)-1-(4-methoxy-benzyl)-4,6-dioxo-1,4,5,6-tetrahydro-[1,3,5]triazin-2-ylamino]-ethyl}-N'-pyridin-2-yl-guanidine. $^1$H NMR (DMSO-d$_6$): δ 10.90 (br, 1H), 9.78 (br, 1H), 8.65 (br, 2H), 8.17 (d, 1H, J=5.4 Hz), 8.07 (m, 1H), 7.87 (t, 1H, J=7.8 Hz), 7.33 (m, 2H), 7.13 (m, 4H), 7.05 (d, 1H, J=8.2 Hz), 6.78 (d, 2H, J=8.7 Hz), 4.98 (s, 2H), 4.86 (s, 2H), 3.67 (s, 3H), 3.54 (m, 2H), 3.36 (br, 2H); HRMS m/z (M+H)$^+$ calcd 519.2268, found 519.2253.

Cpd 118: N-{2-[5-(4-Fluoro-benzyl)-1-(4-methoxy-benzyl)-4,6-dioxo-1,4,5,6-tetrahydro-[1,3,5]triazin-2-ylamino]-ethyl}-N'-(2-fluoro-phenyl)-guanidine. $^1$H NMR (methanol-d$_4$): δ 7.47-7.37 (m, 3H), 7.31 (t, 1H, J=7.8 Hz), 7.23 (m, 2H), 7.18 (d, 2H, J=8.6 Hz), 7.01 (t, 2H, J=8.8 Hz), 6.89 (d, 2H, J=8.8 Hz), 5.06 (s, 2H), 5.01 (s, 2H), 3.76 (s, 3H), 3.56 (t, 2H, J=6.3 Hz), 3.45 (t, 2H, J=6.3 Hz); HRMS m/z (M+H)$^+$ calcd 536.2222, found 536.2227.

Cpd 134: N-Benzoyl-N'-{2-[5-(4-fluoro-benzyl)-1-(4-methoxy-benzyl)-4,6-dioxo-1,4,5,6-tetrahydro-[1,3,5]triazin-2-ylamino]-ethyl}-guanidine. $^1$H NMR (methanol-d$_4$): δ 7.93 (d, 2H, J=8.2 Hz), 7.70 (t, 1H, J=7.5 Hz), 7.57 (t, 2H, J=7.5 Hz), 7.41 (m, 2H), 7.16 (d, 2H, J=8.7 Hz), 6.97 (t, 2H, J=8.7 Hz), 6.85 (d, 2H, J=8.7 Hz), 5.08 (s, 2H), 4.99 (s, 2H), 3.70 (s, 3H), 3.66 (t, 2H, J=6.2 Hz), 3.55 (t, 2H, J=6.2 Hz); HRMS m/z (M+H)$^+$ calcd 546.2265, found 546.2259.

Example 5

N-{2-[5-Benzyl-1-(4-methoxy-benzyl)-4,6-dioxo-1,4,5,6-tetrahydro-[1,3,5]triazin-2-ylamino]-ethyl}-oxyguanidine (Cpd 27)

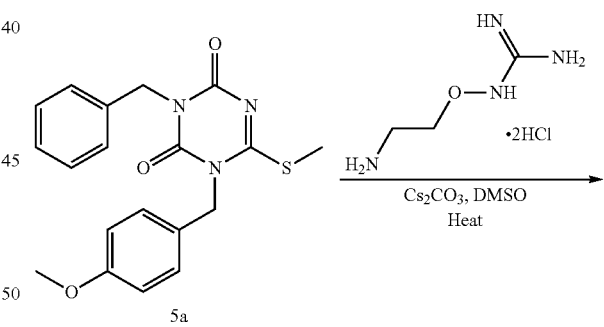

5a

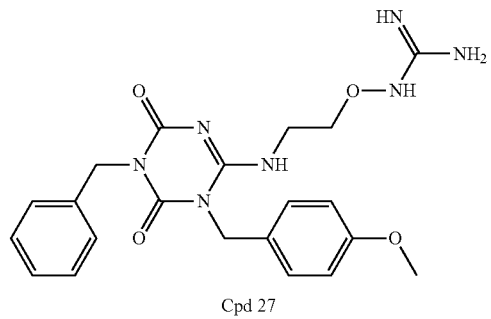

Cpd 27

A. Compound 5a was prepared by the method described in Example 1, Step C, substituting phenyl methanol for 4-ethylbenzyl alcohol.

B. To 3-benzyl-1-(4-methoxy-benzyl)-6-methylsulfanyl-1H-[1,3,5]triazine-2,4-dione 5a (0.056 g, 0.15 mmol) in DMSO (1 mL) was added N-(2-amino-ethyl)-oxyguanidine dihydrochloride salt (0.058 g, 0.30 mmol) and $Cs_2CO_3$ (0.098 mg, 0.30 mmol). The reaction mixture was heated at 70° C. for 5 h and cooled to rt. N-(2-Amino-ethyl)-oxyguanidine dihydrochloride salt (0.058 g, 0.30 mmol) and $Cs_2CO_3$ (0.098 mg, 0.30 mmol) were again added and the resulting slurry stirred at 40° C. for 16 h. The reaction mixture was cooled to room temperature, loaded onto a 1 g C-18 SPE cartridge, and eluted with $CH_3CN$. The eluant was concentrated and the resulting residue was purified by reverse-phase liquid chromatography using a gradient of 90:10 (acetonitrile:water, with 0.1% TFA) to 90:10 (acetonitrile:water, with 0.1% TFA) to give the title compound 27 (99% pure by HPLC, 0.0289 g). $^1$H NMR ($d^6$-DMSO/CDCl$_3$) δ 3.65-3.73 (2H, m), 3.78 (3H, s), 3.96-4.04 (2H, m), 5.01 (2H, s), 5.10 (2H, s), 6.85 (2H, d, J=8.7 Hz), 7.21-7.40 (7H, m), 7.74 (4H, bs); 7.89 (1H, m) 11.58 (1H, bs); HRMS calcd. for $C_{21}H_{26}N_7O_4$ m/z 440.2046 (M+H), found: 440.2030.

Using the procedures of Example 5 and the appropriate reagents, starting materials and purification methods known to those skilled in the art, the following compounds of the present invention were prepared: compound 10.

Example 6

4-[4-(2-Guanidino-ethylamino)-3-(4-methoxy-benzyl)-2,6-dioxo-3,6-dihydro-2H-[1,3,5]triazin-1-ylmethyl]-benzoic acid (Cpd 101)

A. Compound 6a was prepared according to the methods described in Example 1, and substituting 4-hydroxymethylbenzoic acid methyl ester for 4-ethylbenzyl alcohol.

B. 4-[4-(2-Guanidino-ethylamino)-3-(4-methoxy-benzyl)-2,6-dioxo-3,6-dihydro-2H-[1,3,5]triazin-1-ylmethyl] benzoic acid (Cpd. 101). A mixture of compound 6a (20 mg, 0.028 mmol) and lithium hydroxide (6 mg, 0.014 mmol) in 5 mL of MeOH and 1 mL of $H_2O$ was allowed to stir overnight at room temperature. At that time, an additional 6 mg of lithium hydroxide was added and the mixture stirred for and additional 18 h. The mixture was then concentrated and purified by HPLC. The title compound 101 was obtained as its TFA salt (10 mg, 0.014 mmol). $^1$H NMR (DMSO-$d_6$) δ 3.26 (m, 2H), 3.40 (m, 2H), 3.68 (s, 3H), 4.97 (s, 2H), 5.02 (s, 2H), 6.79-6.82 (d, 2H, J=8.7 Hz), 7.06-7.09 (d, 2H, J=8.7 Hz), 7.35-7.38 (d, 2H, J=8.2 Hz), 7.86-7.88 (d, 2H, J=8.3 Hz).

Example 7

N-{2-[5-(4-Hydroxy-benzyl)-1-(4-methoxy-benzyl)-4,6-dioxo-1,4,5,6-tetrahydro-[1,3,5]triazin-2-ylamino]-ethyl}-guanidine (Cpd 110)

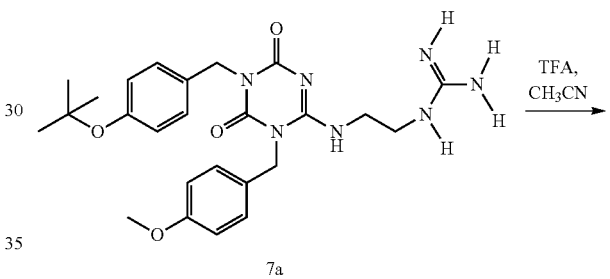

7a

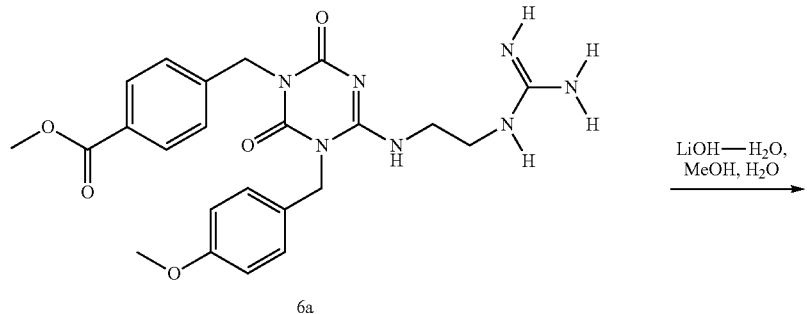

6a

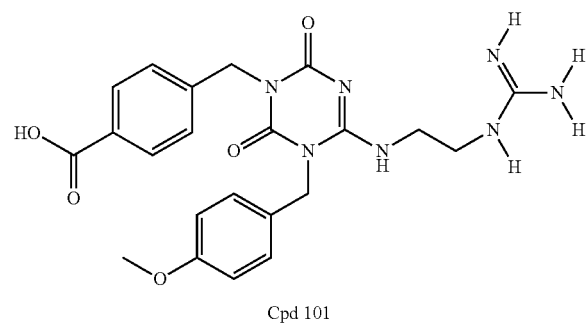

Cpd 101

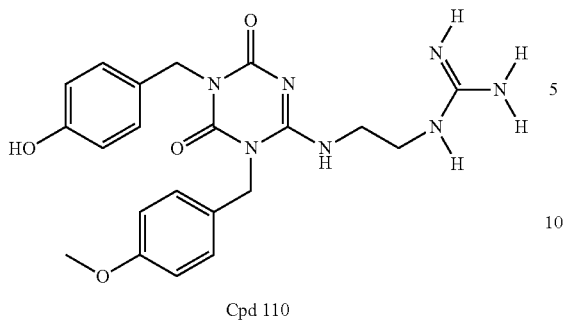

Cpd 110

A. Compound 7a was prepared according to the methods described in Example 1, and substituting (4-tert-butoxy-phenyl)-methanol) for 4-ethylbenzyl alcohol.

B. N-{2-[5-(4-Hydroxy-benzyl)-1-(4-methoxy-benzyl)-4,6-dioxo-1,4,5,6-tetrahydro-[1,3,5]triazin-2-ylamino]-ethyl}-guanidine (Cpd 110). The crude Compound 7a (assumed to be about 0.24 mmol) was dissolved in $CH_3CN$. To this mixture was added 3 mL of TFA. The resulting mixture was allowed to stir overnight at room temperature. The mixture was concentrated and purified by HPLC to give the title compound 110 as its TFA salt (31 mg, 0.046 mmol). $^1H$ NMR (DMSO-$d_5$) δ 1.25-1.28 (m, 1H), 3.28-2.31 (m, 2H), 3.31-3.36 (m, 2H), 3.73 (s, 3H), 4.78 (s, 2H), 4.98 (s, 2H), 6.65-6.68 (d, 2H, J=8.4 Hz), 6.89-6.91 (d, 2H, J=8.7 Hz), 7.11-7.14 (d, 2H, J=8.6 Hz), 7.52-7.54 (d, 2H, J=5.5 Hz), 7.99 (m, 1H).

Example 8

N-{2-[1-(4-Methoxy-benzyl)-5-(4-nitro-benzyl)-4,6-dioxo-1,4,5,6-tetrahydro-[1,3,5]triazin-2-ylamino]-ethyl}-guanidine (Cpd 95)

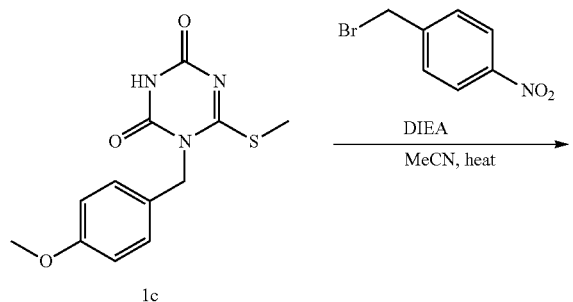

1c

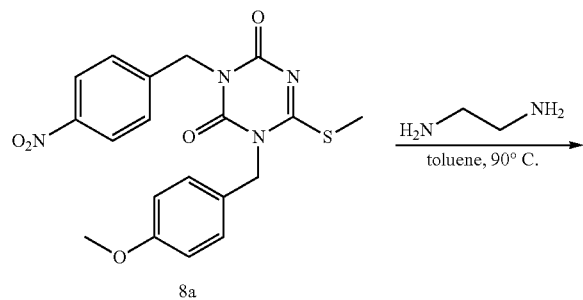

8a

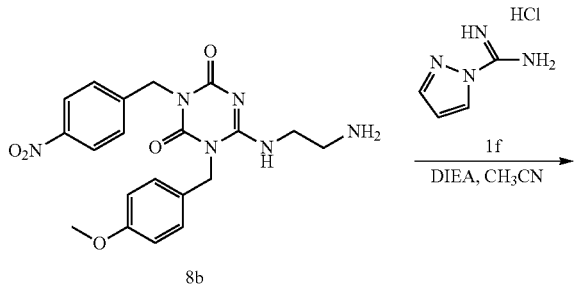

8b

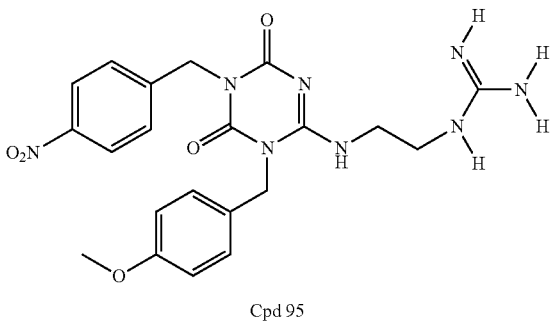

Cpd 95

A. 1-(4-Methoxy-benzyl)-6-methylsulfanyl-3-(4-nitro-benzyl)-1H-[1,3,5]triazine-2,4-dione (Cpd 9a). Compound 1c (200 mg, 0.73 mmol) was dissolved in $CH_3CN$ and was treated with 4-nitrobenzyl bromide (168 mg, 0.86 mmol) and 80 µL (0.73 mmol) of diisopropylethylamine. The resulting mixture was heated to 87° C. and allowed to stir overnight. The reaction mixture was cooled to room temperature, diluted with ethyl acetate, and washed with saturated sodium bicarbonate solution. The organic phase was dried over $MgSO_4$, filtered, and concentrated. The residue was purified by flash chromatography to give compound 8a (44 g, 0.36 mmol).

B. 6-(2-Amino-ethylamino)-1-(4-methoxy-benzyl)-3-(4-nitro-benzyl)-1H-[1,3,5]triazine-2,4-dione (Cpd. 9b). To compound 8a (80 mg, 0.19 mmol) in 10 mL of toluene was added an excess of ethylene diamine (64 µL, 0.95 mmol). The resulting mixture was heated to 90° C. for 26 h. The mixture was taken up in ethyl acetate and washed with water. The organic layer was separated, dried over $MgSO_4$ and concentrated. The crude product 8b (79 mg, 0.18 mmol, 97% yield) was used in the next step without further purification.

C. N-{2-[1-(4-Methoxy-benzyl)-5-(4-nitro-benzyl)-4,6-dioxo-1,4,5,6-tetrahydro-[1,3,5]triazin-2-ylamino]-ethyl}-guanidine (Cpd 95). A mixture of compound 8b (51 mg, 0.12 mmol), 1H-pyrazole-1-carboxamidine hydrochloride (18 mg, 0.12 mmol), and diisopropylethylamine (26 µL, 0.36 mmol) in 10 mL of acetonitrile was allowed to stir at room temperature for several days. The resulting mixture was concentrated and purified by liquid chromatography. The title compound 95 was obtained as a white powder (17 mg, 0.036 mmol) and was submitted as a TFA salt. $^1H$ NMR (DMSO-$d_6$) δ 3.65-3.71 (m, 4H), 3.85 (s, 3H), 5.30 (bm, 4H), 6.99-7.02 (m, 2H), 7.26-7.30 (m, 2H), 7.54-7.60 (m, 2H), 8.02-8.20 (bs, 1H), 8.25 (m, 2H).

Using the procedures of Example 8 and the appropriate reagents, starting materials and purification methods known to those skilled in the art, the following compounds of the present invention were prepared: compounds 42, 43, 47, 55, 56, 59, 94, 97, 98, 99, 100, 102, and 113.

Example 9

N-{2-[5-(4-Amino-benzyl)-1-(4-methoxy-benzyl)-4,6-dioxo-1,4,5,6-tetrahydro-[1,3,5]triazin-2-ylamino]-ethyl}-guanidine (Cpd 125)

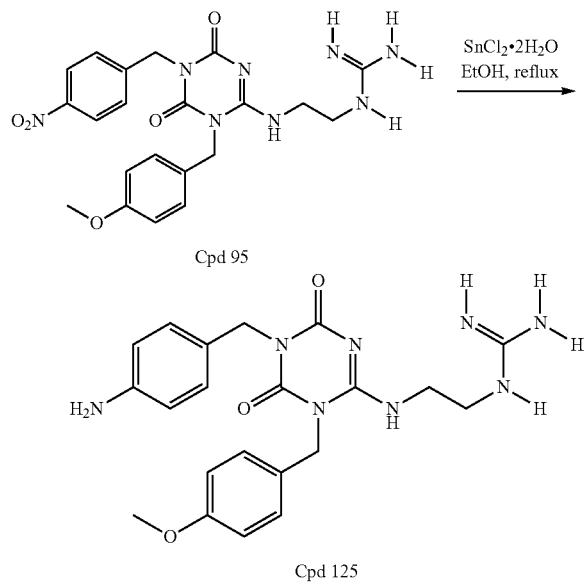

A mixture of the crude Compound 95 (39 mg, 0.083 mmol) and tin (II) chloride dihydrate (94 mg, 0.42 mmol) in 20 mL of EtOH was heated to reflux for 24 h. The solution was concentrated and the residue was purified by HPLC to give the title compound 125 as its TFA salt (6.5 mg, 0.015 mmol). $^1$H NMR (DMSO-$d_6$) δ 3.30 (m, 4H), 3.73 (s, 3H), 4.80 (s, 2H), 4.98 (s, 2H), 6.56-6.78 (m, 2H), 6.88-6.91 (d, 2H, J=8.6 Hz), 7.13-7.20 (m, 4H), 7.43-7.47 (m, 1H), 7.92-7.99 (m, 1H).

Using the procedures of Example 9 and the appropriate reagents, starting materials and purification methods known to those skilled in the art, the following compounds of the present invention were prepared: compound 96.

Example 10

3-(3,4-Dichloro-benzyl)-6-[2-(2-imino-imidazolidin-1-yl)-ethylamino]-1-(4-methoxy-benzyl)-1H-[1,3,5]triazine-2,4-dione (Cpd 60)

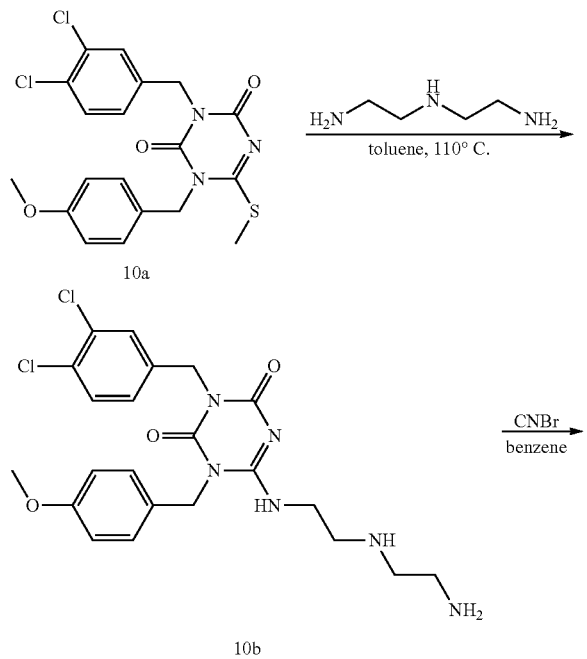

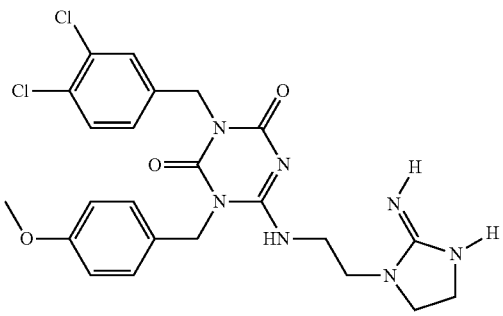

A. Compound 10a was prepared according to the methods described in Example 1, Step C, and substituting (3,4-dichloro-phenyl)-methanol for 4-ethylbenzyl alcohol.

B. 6-[2-(2-Amino-ethylamino)-ethylamino]-3-(3,4-dichloro-benzyl)-1-(4-methoxy-benzyl)-1H-[1,3,5]triazine-2,4-dione (Cpd 10b). To compound 10a (0.400 g, 0.968 mmol) in toluene (6 mL) was added 2,2'-diaminodiethylamine (0.300 g, 2.9 mmol) and the reaction mixture was heated at 110° C. for 4 h. The reaction mixture was cooled to room temperature and then water was added. The mixture was extracted with ethyl acetate, dried over sodium sulfate, filtered, and concentrated to give compound 10b (0.46 g) which was used in the subsequent reaction without further purification.

C. 3-(3,4-Dichloro-benzyl)-6-[2-(2-imino-imidazolidin-1-yl)-ethylamino]-1-(4-methoxy-benzyl)-1H-[1,3,5]triazine-2,4-dione. (Cpd 60). To compound 10b (0.100 g, 0.203 mmol) in benzene (2 mL) was added cyanogen bromide (0.022 g, 0.203 mmol). The reaction mixture was stirred for 2.5 h at room temperature. The reaction mixture was concentrated and then dissolved in a mixture of acetonitrile and methanol. The mixture was purified by reverse-phase chromatography to yield the title compound 60 (0.017 g). $^1$H NMR (DMSO-$d_6$) δ 3.28-3.59 (8H, m), 3.66 (3H, s), 4.83 (2H, s), 4.92 (2H, s), 6.81-6.84 (2H, d, J=8.7 Hz), 7.09-7.12 (2H, d, 8.7 Hz), 7.19-7.22 (1H, d, J=8.3 Hz), 7.46 (1H, s), 7.51-7.54 (1H, d, J=8.3 Hz), 7.86-7.95 (3H, m).

Example 11

N-{2-[1-(4-Hydroxy-benzyl)-5-(4-methoxy-benzyl)-4,6-dioxo-1,4,5,6-tetrahydro-[1,3,5]triazin-2-ylamino]-ethyl}-guanidine (Cpd 143)

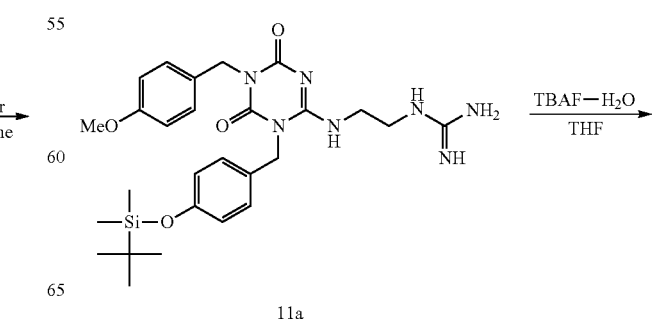

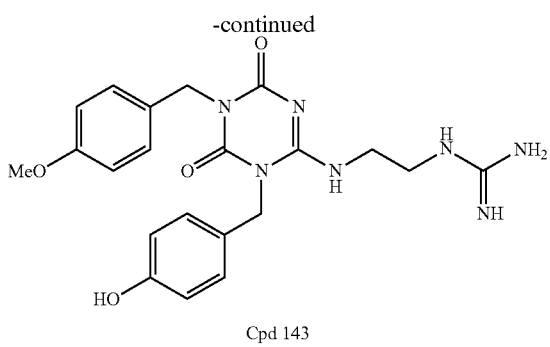

Cpd 143

A. Compound 11a (50 mg, 0.09 mmol) was prepared according to the methods described in Example 2, and substituting [4-(tert-butyl-dimethyl-silanyloxy)-phenyl]-methanol for 4-methoxybenzyl alcohol in Step D.

B. Compound 11a was suspended in THF (2 mL) and the reaction mixture was treated with tetrabutylammonium fluoride monohydrate (24 mg, 0.09 mmol). The solution was stirred at room temperature overnight. The mixture was then concentrated under nitrogen and the residue was purified by reverse phase preparative HPLC to give the title compound 143 (3.8 mg) as a white solid. M+ (ES+)=440.1; $^1$H NMR (MeOD, d$_4$). δ 3.32 (m, 2H), 3.50 (t, 2H, J=7.08 Hz), 3.78 (s, 3H), 4.99 (s, 2H), 5.03 (s, 2H), 6.77 (d, 2H, J=8.58 Hz), 6.85 (d, 2H, J=8.71 Hz), 7.07 (d, 2H, J=8.62 Hz), 7.36 (d, 2H, J=8.67 Hz).

Example 12

N-{2-[1-(4-Amino-benzyl)-5-(4-chloro-benzyl)-4,6-dioxo-1,4,5,6-tetrahydro-[1,3,5]triazin-2-ylamino]-ethyl}-guanidine (Cpd 122)

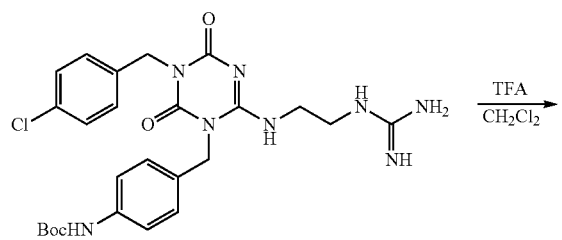

12a

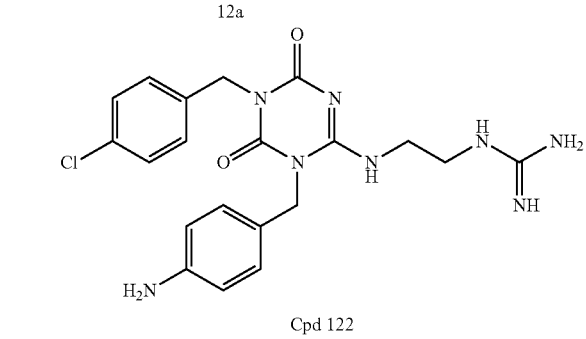

Cpd 122

A. Compound 12a (50 mg, 0.09 mmol) was prepared according to the methods described in Example 2, and substituting (4-hydroxymethyl-phenyl)-carbamic acid tert-butyl ester for 4-methoxybenzyl alcohol in Step D.

B. Compound 12a (70 mg, 0.129 mmol) was suspended in dichloromethane (3 mL) and the solution was treated with trifluoroacetic acid (0.5 mL). The reaction was allowed to stir overnight at room temperature. The mixture was concentrated under nitrogen and the residue was purified by reverse phase preparative HPLC to give the title compound 122 (35.9 mg) as a white solid. M+ (ES+)=443.1; $^1$H NMR (DMSO, d$_6$). δ 3.18-3.25 (m, 2H), 3.28-3.31 (m, 2H), 4.76 (s, 2H), 4.82 (s, 2H), 4.88 (s, 2H), 6.75 (d, 2H, J=8.25 Hz), 7.02 (d, 2H, J=8.38 Hz), 7.22-7.32 (m, 4H), 7.53 (d, 2H, J=4.02 Hz), 7.95 (m, 1H).

Example 13

N-{2-[5-(3,4-Dichloro-benzyl)-1-(4-methoxy-benzyl)-4,6-dioxo-1,4,5,6-tetrahydro-[1,3,5]triazin-2-ylamino]-ethyl}-N'-cyano-guanidine (Cpd 28)

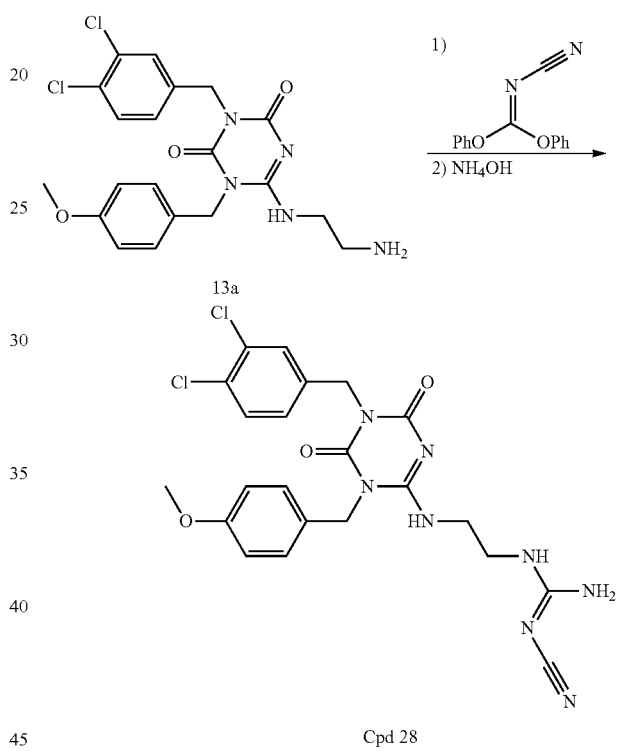

Cpd 28

A. Compound 13a was prepared according to Example 1, substituting 3,4-dichlorophenyl methanol for 4-ethylbenzyl alcohol in Step D.

B. To a mixture of Cpd 13a (0.050 g, 0.11 mmol) in isopropyl alcohol (1 mL) was added triethylamine (0.017 mL, 0.12 mmol) and diphenyl N-cyanocarbonimidate (0.029 g, 0.12 mmol). The reaction mixture was stirred for 2 h at room temperature then concentrated under vacuum. The resulting residue was suspended in EtOH (0.75 mL) and NH$_4$OH (0.25 mL, 14.8 N (aq)) was added. The reaction mixture was stirred for 16 h at 50° C., concentrated under vacuum, and the resulting residue was purified by reverse-phase liquid chromatography using a gradient of 90:10 (water:acetonitrile, with 0.1% TFA) to 90:10 (acetonitrile:water, with 0.1% TFA) to give the title compound 28 (99% pure by HPLC, 0.0017 g); HRMS calcd. for $C_{22}H_{23}Cl_2N_8O_3$ m/z 517.1270 (M+H), found: 517.1281.

Using the procedures of Example 13 and the appropriate reagents, starting materials and purification methods known to those skilled in the art, the following compounds of the present invention were prepared: compound 143.

Example 14

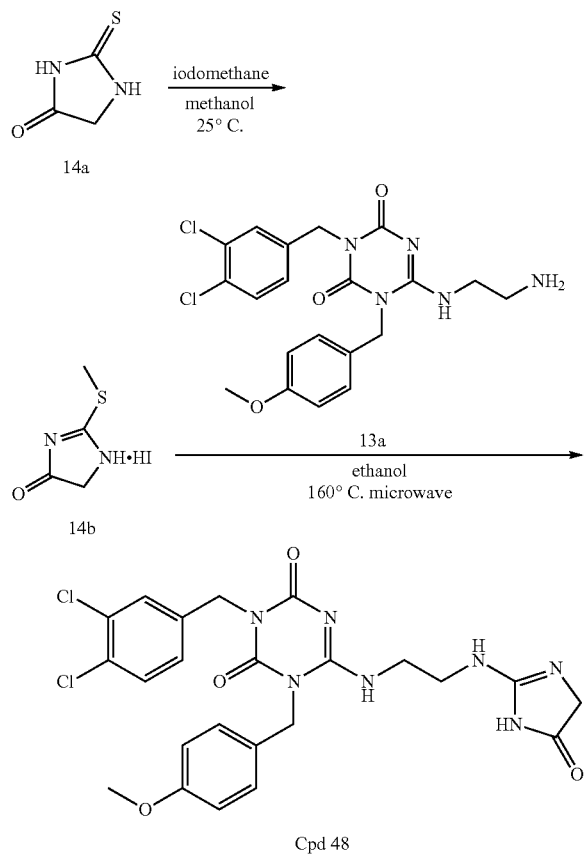

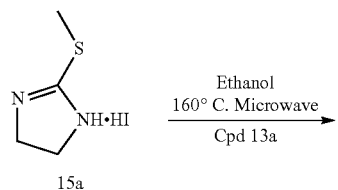

A. 1,5-Dihydro-2-(methylthio)-4H-imidazol-4-one monohydriodide (Cpd 15b). To a solution of compound 14a (420 mg, 3.6 mmol) in EtOH (5 mL) was added iodomethane (0.268 mL, 4.3 mmol). The mixture was stirred at 25° C. for 16 h, then concentrated to a residue to provide compound 14b, which was used in the next reaction without further purification.

B. 3-(3,4-Dichloro-benzyl)-1-(4-methoxy-benzyl)-6-[2-(5-oxo-4,5-dihydro-1H-imidazol-2-ylamino)-ethylamino]-1H-[1,3,5]triazine-2,4-dione 4 (Cpd 52). To a solution of compound 14b (0.0373 mg, 0.14 mmol) in ethanol (0.75 mL) was added compound 13a (50 mg, 0.13 mmol). The mixture was irradiated (μwave) at 160° C. for 15 min, concentrated, and the resulting residue was purified by reverse-phase liquid chromatography using a gradient of 90:10 (water:acetonitrile, with 0.1% TFA) to 90:10 (acetonitrile:water, with 0.1% TFA) to give the title compound 48 (89% pure by HPLC, 0.0025 g). HRMS calcd. for $C_{23}H_{24}Cl_2N_7O_4$ m/z 532.1267 (M+H), found: 532.1257.

Example 15

3-(3,4-Dichloro-benzyl)-6-[2-(4,5-dihydro-1H-imidazol-2-ylamino)-ethylamino]-1-(4-methoxy-benzyl)-1H-[1,3,5]triazine-2,4-dione (Cpd 49)

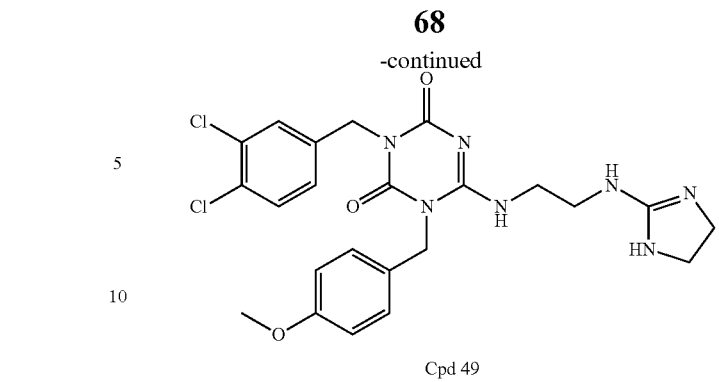

To a solution of compound 15a (0.054 mg, 0.22 mmol) in ethanol (1 mL) was added compound 13a (50 mg, 0.11 mmol). The mixture was irradiated in a microwave reactor at 160° C. for 15 min, concentrated, and the resulting residue was purified by reverse-phase liquid chromatography using a gradient of 90:10 (water:acetonitrile, with 0.1% TFA) to 90:10 (acetonitrile:water, with 0.1% TFA) to give the title compound 49 (93% pure by HPLC, 0.0082 g). HRMS calcd. for $C_{23}H_{26}Cl_2N_7O_3$ m/z 518.1474 (M+H), found: 518.1479.

Example 16

N-{2-[5-(4-Fluoro-benzyl)-1-(4-methoxy-benzyl)-4,6-dioxo-1,4,5,6-tetrahydro-[1,3,5]triazin-2-ylamino]-ethyl}-N'-amino-guanidine (Cpd 93)

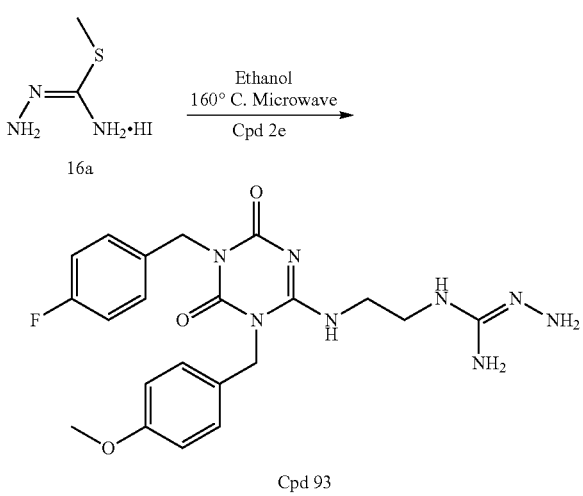

To a solution of compound 16a (0.061 mg, 0.22 mmol) in ethanol (1 mL) was added compound 2e (50 mg, 0.13 mmol). The mixture was irradiated in a microwave reactor at 160° C. for 15 min, concentrated, and the resulting residue was purified by reverse-phase liquid chromatography using a gradient of 90:10 (water:acetonitrile, with 0.1% TFA) to 90:10 (acetonitrile:water, with 0.1% TFA) to give the title compound 93 (99% pure by HPLC, 0.018 g). $^1$H NMR (CDCl$_3$) δ 3.22-3.73 (2H, m), 3.38-3.55 (2H, m), 3.75 (2H, t, J=5.8 Hz), 3.77 (3H, s), 5.01 (2H, s), 5.07 (2H, s), 5.44-4.86 (2H, bs), 6.83 (2H, d, J=8.7 Hz), 6.90-7.03 (2H, m), 7.16 (2H, d, J=8.7 Hz), 7.48-7.36 (2H, m). HRMS calcd. for $C_{21}H_{26}FN_8O_3$ m/z 457.2112 (M+H), found: 457.2101.

Example 17

N-{2-[5-(4-fluoro-benzyl)-1-(4-methoxy-benzyl)-4,6-dioxo-1,4,5,6-tetrahydro-[1,3,5]triazin-2-ylamino]-acetyl}-N'-boc-guanidine (Cpd 132)

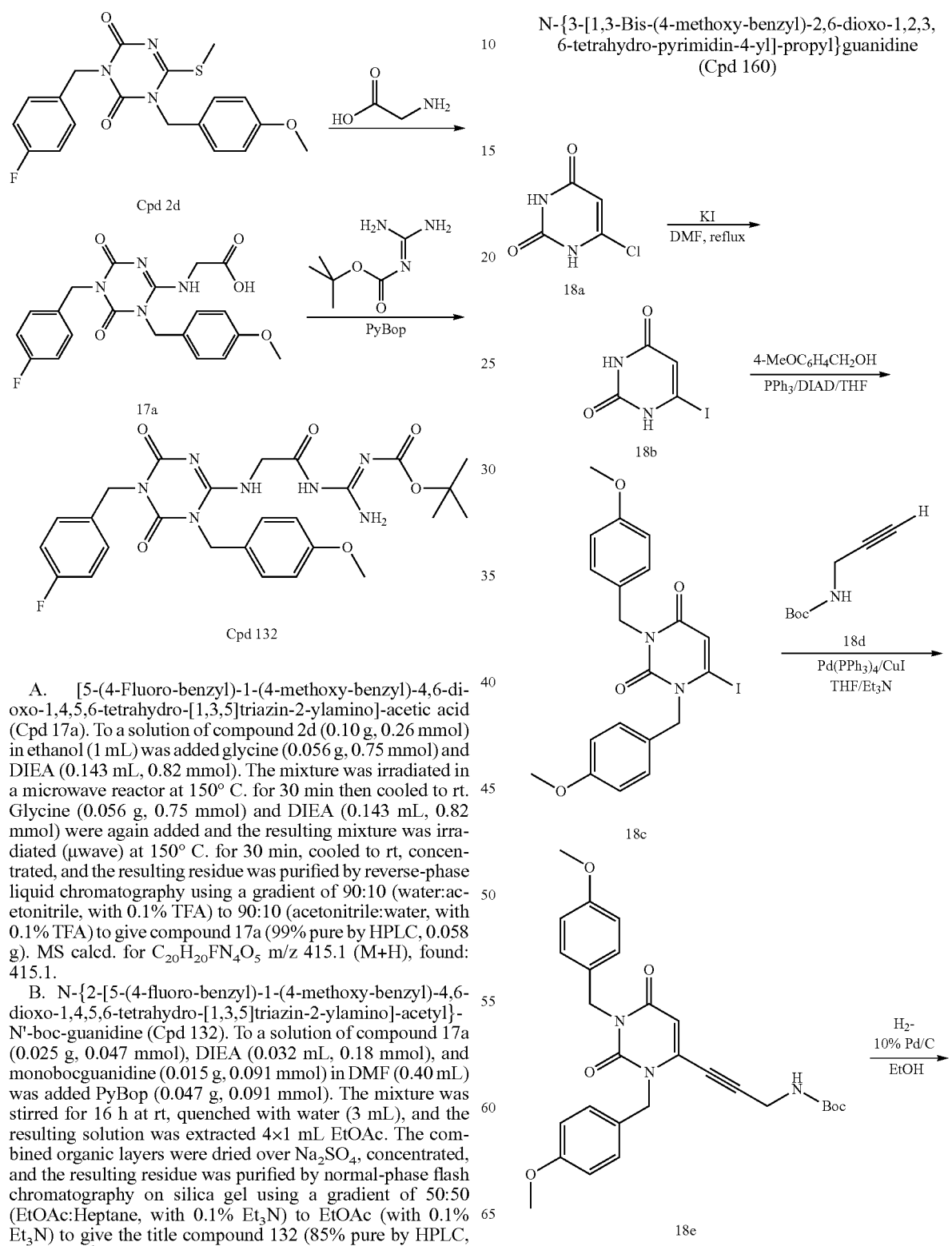

A. [5-(4-Fluoro-benzyl)-1-(4-methoxy-benzyl)-4,6-dioxo-1,4,5,6-tetrahydro-[1,3,5]triazin-2-ylamino]-acetic acid (Cpd 17a). To a solution of compound 2d (0.10 g, 0.26 mmol) in ethanol (1 mL) was added glycine (0.056 g, 0.75 mmol) and DIEA (0.143 mL, 0.82 mmol). The mixture was irradiated in a microwave reactor at 150° C. for 30 min then cooled to rt. Glycine (0.056 g, 0.75 mmol) and DIEA (0.143 mL, 0.82 mmol) were again added and the resulting mixture was irradiated (μwave) at 150° C. for 30 min, cooled to rt, concentrated, and the resulting residue was purified by reverse-phase liquid chromatography using a gradient of 90:10 (water:acetonitrile, with 0.1% TFA) to 90:10 (acetonitrile:water, with 0.1% TFA) to give compound 17a (99% pure by HPLC, 0.058 g). MS calcd. for $C_{20}H_{20}FN_4O_5$ m/z 415.1 (M+H), found: 415.1.

B. N-{2-[5-(4-fluoro-benzyl)-1-(4-methoxy-benzyl)-4,6-dioxo-1,4,5,6-tetrahydro-[1,3,5]triazin-2-ylamino]-acetyl}-N'-boc-guanidine (Cpd 132). To a solution of compound 17a (0.025 g, 0.047 mmol), DIEA (0.032 mL, 0.18 mmol), and monobocguanidine (0.015 g, 0.091 mmol) in DMF (0.40 mL) was added PyBop (0.047 g, 0.091 mmol). The mixture was stirred for 16 h at rt, quenched with water (3 mL), and the resulting solution was extracted 4×1 mL EtOAc. The combined organic layers were dried over $Na_2SO_4$, concentrated, and the resulting residue was purified by normal-phase flash chromatography on silica gel using a gradient of 50:50 (EtOAc:Heptane, with 0.1% $Et_3N$) to EtOAc (with 0.1% $Et_3N$) to give the title compound 132 (85% pure by HPLC, 0.0263 g). $^1$H NMR (CDCl$_3$) δ 1.46 (9H, s), 3.79 (3H, s), 4.05 (2H, s), 5.07 (4H, s), 6.90 (2H, d, J=8.7 Hz), 6.98 (2H, at, J=6.7 Hz), 7.30 (2H, d, J=8.7 Hz), 7.50 (2H, dd, J=8.7 and 8.6 Hz), 8.61 (1H, bs); MS calcd. for $C_{26}H_{31}FN_7O_6$ m/z 556.2320 (M+H), found: 556.2341.

Example 18

N-{3-[1,3-Bis-(4-methoxy-benzyl)-2,6-dioxo-1,2,3,6-tetrahydro-pyrimidin-4-yl]-propyl}guanidine (Cpd 160)

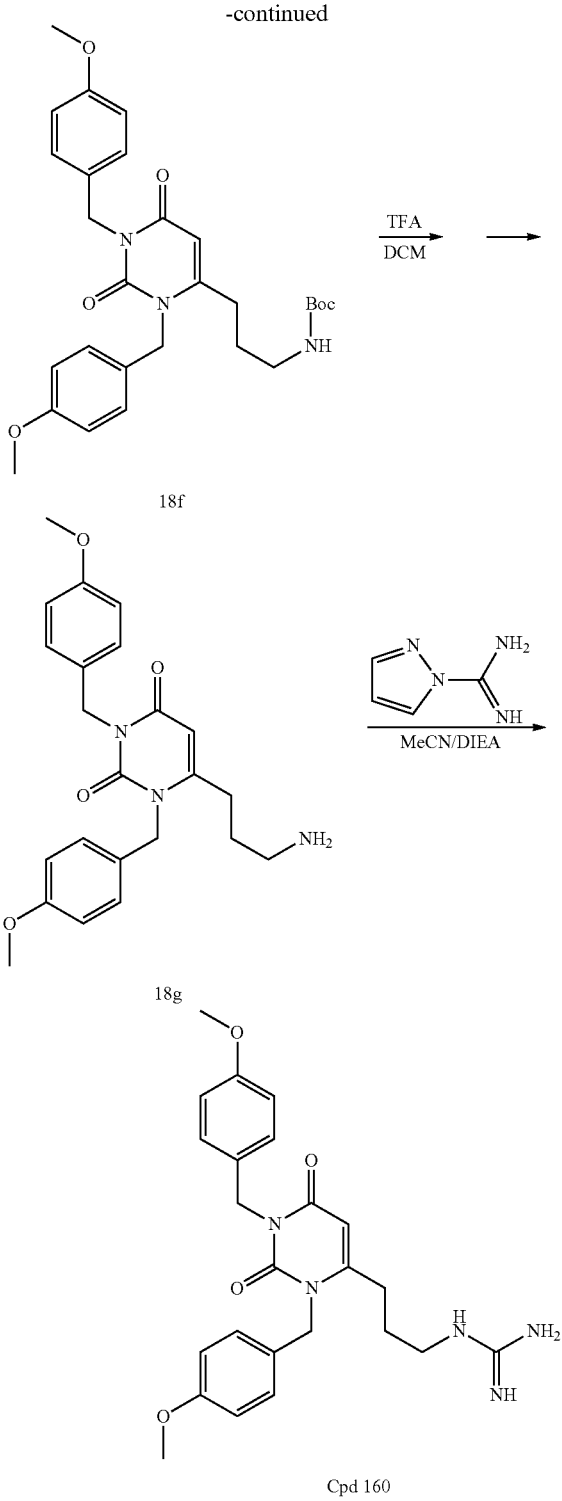

B. 6-Iodo-1,3-bis-(4-methoxy-benzyl)-1H-pyrimidine-2,4-dione (Cpd 18c). Compound 18b (1.00 g, 4.2 mmol), 4-methoxybenzyl alcohol (1.7 g, 3 eq), PPh$_3$ (4.00 g) were dissolved in dry THF (25 mL) under an atmosphere of N$_2$. DIAD was added dropwise at approximately 1 mL/min until the yellow color remained (about 4 eq total). The reaction mixture was stirred for 4 h at RT and evaporated. The residue was subjected to normal phase column chromatography (silica gel, gradient mixture heptane-ethyl acetate), providing compound 18c. $^1$H NMR (CDCl$_3$) δ 3.78 (s, 3H), 3.79 (s, 3H), 5.04 (s, 2H), 5.27 (s, 2H), 6.54 (s, 1H), 6.82 (d, J=7.3 Hz, 2H), 6.86 (d, J=8.7 Hz, 2H), 7.22 (d, J=7.3 Hz, 2H), 7.42 (d, J=8.7 Hz, 2H). MS m/z 479.1 (M+H).

C. N-Boc-Propargylamine (Cpd 18d). Propargylamine (5.50 g, 0.1 mol) and di-tert-butyl dicarbonate (4.36 g, 2 eq.) were suspended together in 100 mL of a 10% aqueous solution of NaHCO$_3$. Reaction mixture was stirred overnight and extracted by EtOAc (3×20 mL). The organic phases were combined together, washed with citric acid 10% aq., dried over MgSO$_4$, filtered and evaporated, providing compound 18d as white solid (10.1 g, 65% yield). $^1$H NMR (CDCl$_3$) δ 4.72 (bs, 1H), 3.91 (d, J=3.0 Hz, 2H), 2.22 (t, J=2.9 Hz, 1H), 1.51 (s, 9H).

D. {3-[1,3-Bis-(4-methoxy-benzyl)-2,6-dioxo-1,2,3,6-tetrahydro-pyrimidin-4-yl]-prop-2-ynyl}-carbamic acid tert-butyl ester (Cpd 18e). Compound 18c (240 mg, 0.5 mmol) and compound 18d (150 mg, 1 mmol) were dissolved in a mixture of dry THF (10 mL) and Et$_3$N (2 mL). Pd(PPh$_3$)$_4$ (40 mg) and copper (I) iodide (20 mg) were added simultaneously in one portion. The reaction mixture was stirred overnight at RT under a N$_2$ atmosphere and evaporated. The residue was subjected to normal phase column chromatography (silica gel column, heptane-EtOAc 8:2 to 0:10 gradient mixture), providing compound 18e as yellow solid. $^1$H NMR (CDCl$_3$) δ 7.42 (d, J=8.7 Hz, 2H), 7.28 (d, J=8.7 Hz, 2H), 6.84 (d, J=9.1 Hz, 2H), 6.81 (d, J=9.1 Hz, 2H), 5.93 (s, 1H), 5.08 (s, 2H), 5.03 (s, 2H), 3.78 (s, 3H), 3.76 (s, 3H), 1.44 (s, 9H).

E. {3-[1,3-Bis-(4-methoxy-benzyl)-2,6-dioxo-1,2,3,6-tetrahydro-pyrimidin-4-yl]-propyl}-carbamic acid tert-butyl ester (Cpd 18f). Compound 18e (500 mg, 0.1 mmol) was dissolved in EtOH (10 mL) and suspended with 10% Pd on carbon (40 mg). The reaction mixture was hydrogenated for 24 h at RT under atmospheric pressure, filtered through a Celite™ plug, and evaporated, providing 501 mg of white solid 18f. $^1$H NMR (CDCl$_3$) δ 7.38 (d, J=8.7 Hz, 2H), 7.00 (d, J=8.7 Hz, 2H), 6.87-6.72 (m, 4H), 5.54 (s, 1H), 5.01 (s, 2H), 4.99 (s, 2H), 3.71 (s, 3H), 3.70 (s, 3H), 3.08-3.00 (m, 2H), 2.39-2.30 (m, 2H), 1.65-1.55 (m, 2H), 1.34 (s, 9H).

F. 6-(3-Amino-propyl)-1,3-bis-(4-methoxy-benzyl)-1H-pyrimidine-2,4-dione (Cpd 18g). Compound (18f) (500 mg, 0.098 mmol) was dissolved in 10 ml DCM-TFA 9:1 mixture and stirred at RT. Reaction was monitored by HPLC. After 10 h all starting material disappeared, reaction mixture was filtered through Celite™ plug and evaporated, providing 350 mg of 18g (TFA salt, white solid). MS m/z 410.0 (M+H).

G. N-{3-[1,3-Bis-(4-methoxy-benzyl)-2,6-dioxo-1,2,3,6-tetrahydro-pyrimidin-4-yl]-propyl}-guanidine (Cpd 160). Compound 18g (260 mg TFA salt, 0.5 mmol) and 1H-pyrazole-1-carboxamidine hydrochloride (290 mg, 4 eq) were suspended in 20 ml MeCN-DIEA 9:1 mixture, stirred at RT overnight and evaporated. The residue was dissolved in MeOH and subjected to HPLC, providing after lyophilization 128.5 mg of Compound 160 (30% yield, white powder, di-TFA salt). $^1$H NMR (CD$_3$CN) δ 7.50 (m, 1H), 7.28 (d, J=8.7 Hz, 2H), 7.08 (d, J=8.7 Hz, 2H), 6.87 (d, J=7.6 Hz, 2H), 6.83 (d, J=7.7 Hz, 2H), 6.6 (bs, 3H), 5.61 (s, 1H), 5.01 (s, 2H), 4.99 (s, 2H), 3.75 (s, 6H), 3.14-3.07 (m, 2H), 2.55-2.45 (m, 2H), 1.79-1.69 (m, 2H). MS m/z 452.0 (M+H).

A. 6-Iodo-1H-pyrimidine-2,4-dione (18b). Compound 18a (5 g, 34 mmol) and sodium iodide (20 g) were dissolved in anhydrous DMF (50 mL) and heated to reflux for 1.5 h (Ar atmosphere). The DMF was evaporated, and the solid residue dissolved in H$_2$O (200 mL). The solution was stirred at RT for 4 h, a solid material was collected by vacuum filtration, and the solid was washed with H$_2$O and dried. The solid was crystallized from EtOAc, providing compound 18b. $^1$H NMR (DMSO-d$_6$) δ 6.03 (s, 1H), 11.2 (s, 1H), 11.6 (s, 1H).

Example 19

N-{2-[1,3-Bis-(4-methoxy-benzyl)-2,6-dioxo-1,2,3,6-tetrahydro-pyrimidin-4-yloxy]-ethyl}-guanidine (Cpd 158)

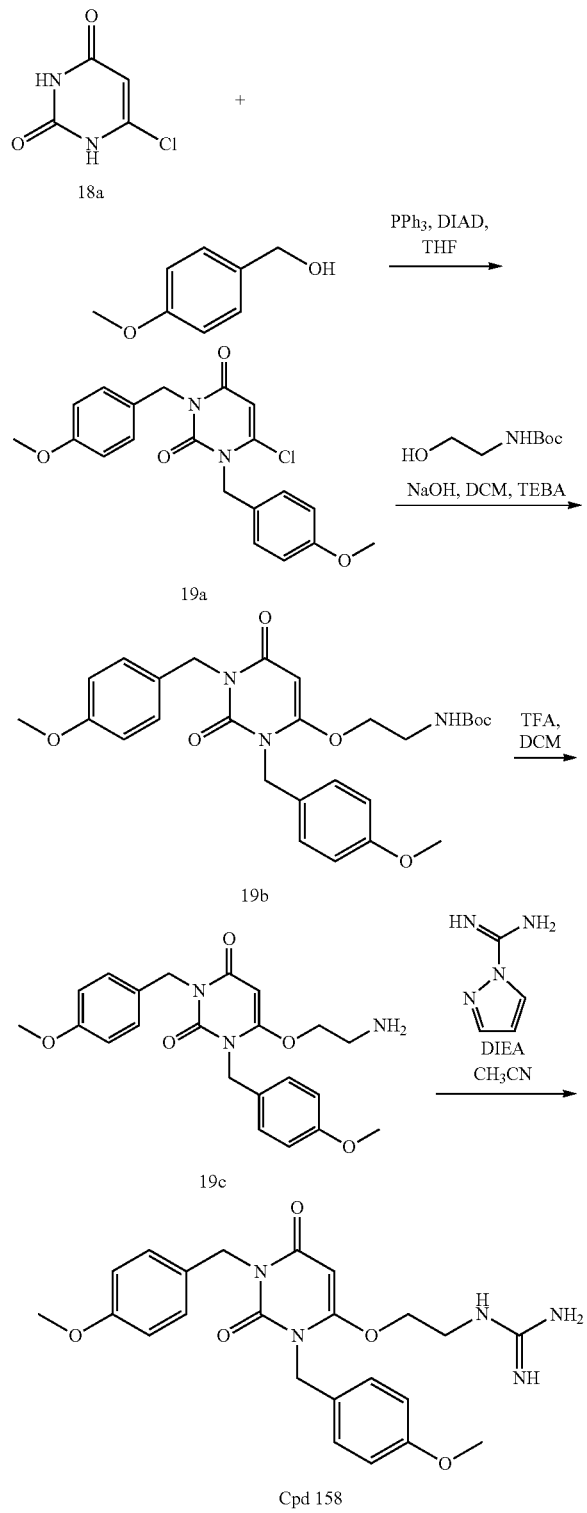

A. 6-Chloro-1,3-bis-(4-methoxy-benzyl)-1H-pyrimidine-2,4-dione (Cpd 19a). A solution of compound 18a (500 mg, 3.4 mmol), 4-methoxybenzyl alcohol (990 mg, 7.2 mmol), triphenylphosphine (2.9 g, 11.2 mmol), and diisopropylazodicarboxylate (1.6 mL, 8.2 mmol) in THF (100 mL) was allowed to stir at room temperature overnight. The solution was concentrated. The concentrate was taken up in ethyl acetate and washed sequentially with saturated sodium bicarbonate and brine. The organic layer was dried over magnesium sulfate, filtered, and the filtrate was concentrated. The concentrate was purified by reverse phase chromatography to give the title compound 19a (552 mg). M+ (ES+)=386.9. $^1$H NMR (methanol-$d_4$). δ 3.75 (s, 3H), 3.76 (s, 3H), 5.01 (s, 2H), 5.21 (s, 2H), 5.99 (s, 1H), 6.83 (d, 4H, J=8.9 Hz), 6.87 (d, 2H, J=8.9 Hz), 7.23 (d, 2H, 8.5 Hz), 7.32 (d, 2H, J=8.9 Hz).

B. {2-[1,3-Bis-(4-methoxy-benzyl)-2,6-dioxo-1,2,3,6-tetrahydro-pyrimidin-4-yloxy]-ethyl}-carbamic acid tert-butyl ester (Cpd 19b). To a solution of t-butyl-N-(2-hydroxyethyl)carbamate (40 μL, 0.26 mmol), benzyltriethyammonium chloride (3 mg, 0.013 mmol) and 3M NaOH solution (870 μL, 2.6 mmol) was added a solution of compound 19a (50 mg, 0.13 mmol) in dichloromethane (3 mL). After stirring overnight, the mixture was separated. The aqueous layer was extracted two times with dichloromethane. The combined organic extracts were dried over magnesium sulfate, filtered, and the filtrate was concentrated. The concentrate was purified by reverse phase chromatography after dissolving in DMSO to afford the title compound 19b as white powder. M+ (ES+)=512.0. $^1$H NMR (DMSO, $d_6$). δ 1.36 (s, 9H), 3.33 (m, 2H), 3.72 (m, 2H), 4.88 (s, 2H), 4.94 (s, 2H), 6.85 (m, 4H), 7.20 (m, 4H).

C. 6-(2-Amino-ethoxy)-1,3-bis-(4-methoxy-benzyl)-1H-pyrimidine-2,4-dione (Cpd 19c). To a solution of compound 19b (assume 0.12 mmol) in dichloromethane (2 mL) was added trifluoroacetic acid (50 μL). Additional TFA (100 μL) was added. Additional TFA (150 μL) was added and the reaction was allowed to stir for an additional 16 hrs. The mixture was concentrated and purified by reverse phase chromatography to obtain the title compound 19c (24 mg) as a white solid. M+ (ES+)=411.9. $^1$H NMR (methanol-$d_4$). δ 3.36 (t, 2H, J=4.9, 5.0 Hz), 3.75 (s, H), 3.76 (s, 3H), 5.01 (s, 2H), 5.10 (s, 2H), 5.28 (s, 1H), 6.84 (m, 4H), 7.22 (d, 2H, J=8.6 Hz), 7.30 (d, 2H, J=5.6 Hz).

D. N-{2-[1,3-Bis-(4-methoxy-benzyl)-2,6-dioxo-1,2,3,6-tetrahydro-pyrimidin-4-yloxy]-ethyl}-guanidine (Cpd 158). A mixture of compound 19c (20 mg, 0.05 mmol), 1H-pyrazole-1-carboxamidine HCl (8.7 mg, 0.06 mmol), and DIEA (16.5 μL, 0.15 mmol) in acetonitrile (5 mL) was allowed to stir at rt overnight. The mixture was concentrated and purified by reverse phase chromatorgraphy to obtain the title compound 158 as a white solid. M+ (ES+)=453.9. $^1$H NMR (DMSO, $d_6$). δ 3.57 (t, 2H, J=4.7, 5.2 Hz), 3.71 (s, 3H), 3.72 (s, 3H), 4.20 (t, 2H, J=4.9, 4.6 Hz), 4.89 (s, 2H), 4.94 (s, 2H), 5.31 (s, 1H), 6.87 (m, 4H), 7.22 (m, 4H), 7.78 (t, 1H, J=5.6, 5.6 Hz).

Example 20

N-{2-[1,3-Bis-(4-methoxy-benzyl)-2,6-dioxo-1,2,3,6-tetrahydro-pyrimidin-4-ylsulfanyl]-ethyl}-guanidine (Cpd 159)

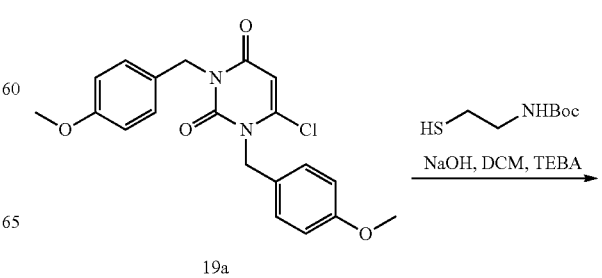

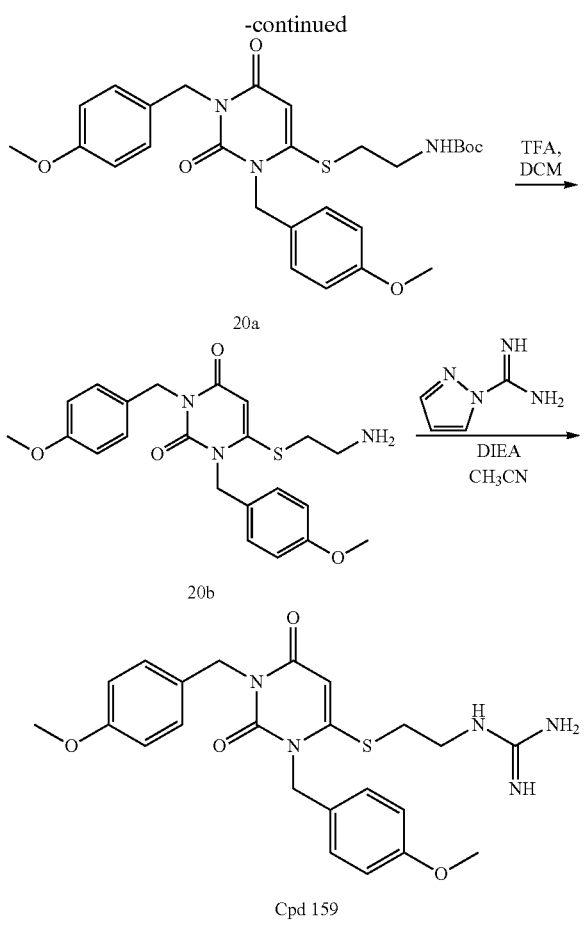

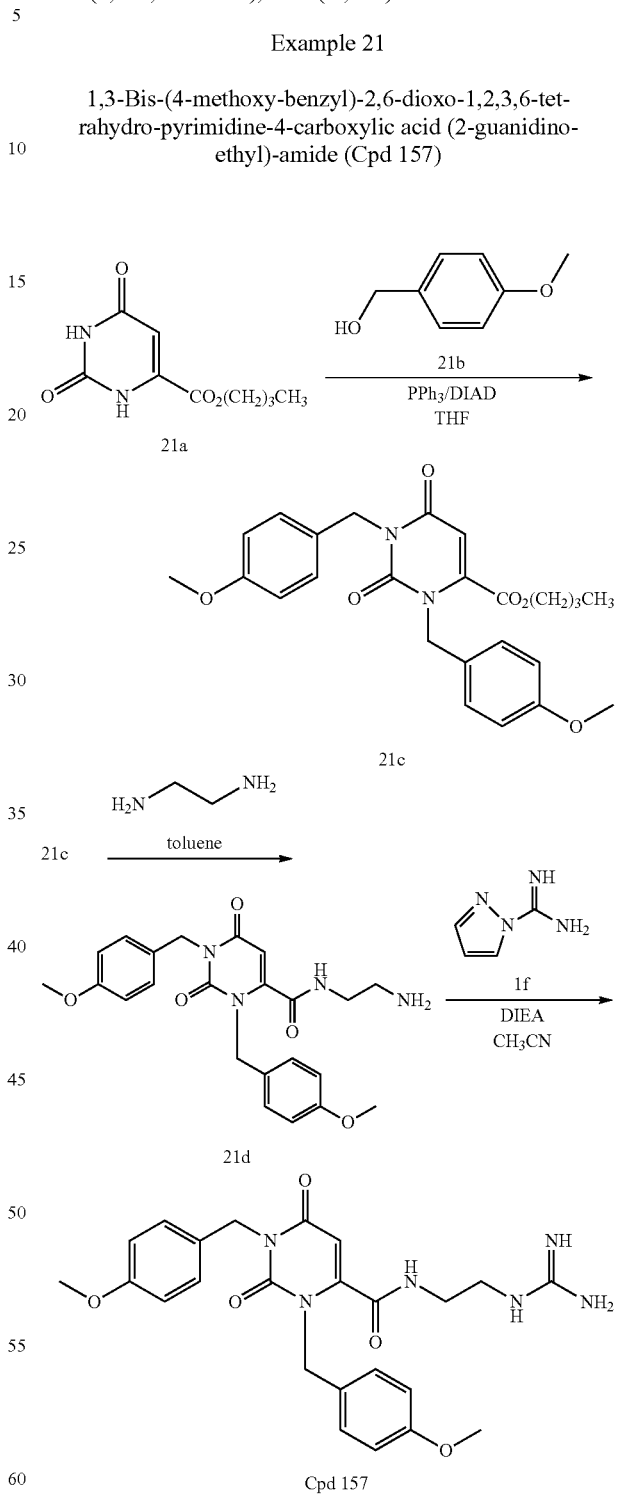

NMR (DMSO, d$_6$). δ 3.19 (t, 2H, J=6.2, 6.6 Hz), 3.42 (m, 2H), 3.72 (s, 6H), 4.93 (s, 2H), 5.08 (s, 2H), 5.84 (s, 1H), 6.86 (d, 2H, J=8.7 Hz), 6.90 (s, 2H, J=8.7 Hz), 7.16 (d, 2H, J=8.7 Hz), 7.25 (d, 2H, J=8.6 Hz), 7.60 (m, 1H).

Example 21

1,3-Bis-(4-methoxy-benzyl)-2,6-dioxo-1,2,3,6-tetrahydro-pyrimidine-4-carboxylic acid (2-guanidino-ethyl)-amide (Cpd 157)

A. {2-[1,3-Bis-(4-methoxy-benzyl)-2,6-dioxo-1,2,3,6-tetrahydro-pyrimidin-4-ylsulfanyl]-ethyl}-carbamic acid tert-butyl ester (Cpd 20a). To a solution of 2-(boc-amino) ethanethiol (87 µL, 0.52 mmol), 3M NaOH (1.7 mL, 5.2 mmol), and benzyltriethyammonium chloride (5 mL) was added a mixture of compound 19a (100 mg, 0.26 mmol) in dichloromethane (5 mL). The mixture was allowed to stir overnight at rt. The mixture was separated, and the aqueous layer was washed with dichloromethane. The combined organic extracts were dried over magnesium sulfate, filtered, and the filtrate was concentrated. The concentrate was triturated in MeOH and collected to obtain the title compound 20a as a white solid. M+ (ES+)=527.8.

B. 6-(2-Amino-ethylsulfanyl)-1,3-bis-(4-methoxy-benzyl)-1H-pyrimidine-2,4-dione (Cpd 20b). To a mixture of compound 20a (78 mg, 0.15 mmol) in dichloromethane (3 mL) was added TFA (0.5 mL), and the reaction was stirred for 2 h. The mixture was concentrated and the residue was purified by reverse phase chromatography to obtain the title compound 20b as a white powder. M+ (ES+)=427.8. $^1$H NMR (methanol-d$_4$). δ 3.37 (s, 6H), 4.84 (m, 4H), 5.05 (s, 2H), 5.20 (s, 2H), 6.85 (m, 4H), 7.18 (d, 2H, J=8.7 Hz), 7.34 (d, 2H, J=6.6 Hz).

C. N-{2-[1,3-Bis-(4-methoxy-benzyl)-2,6-dioxo-1,2,3,6-tetrahydro-pyrimidin-4-ylsulfanyl]-ethyl}-guanidine (Cpd 159). A solution of compound 20b (assumed 0.09 mmol), 1-H-pyrazole-1-carboxamidine HCl (16 mg, 0.108 mmol), and DIEA (5 µL, 0.45 mmol) in acetonitrile (3 mL) was allowed to stir at it overnight. The mixture was concentrated and purified by reverse phase chromatography to obtain the title compound 159 as a white powder. M+ (ES+)=469.8. $^1$H A. 1,3-Bis-(4-methoxy-benzyl)-2,6-dioxo-1,2,3,6-tetrahydro-pyrimidine-4-carboxylic acid butyl ester (Cpd 21c). A mixture Compound 21a (1.00 g, 4.7 mmol), 4-methoxy-benzyl alcohol (Cpd 21b, 2.00 g, 14.1 mmol) and PPh$_3$ (5.00 g, 19 mmol) were dissolved in 50 mL of dry THF at 20° C.

DIAD (3.8 g, 18 mmol) was added dropwise, and the reaction mixture was allowed to stir overnight at room temperature. The reaction mixture was washed with water, and extracted with EtOAc. The combined organic fractions were dried over $MgSO_4$, filtered and evaporated, providing compound 21c as white solid. M+ (ES+)=453.3. $^1$H NMR ($CDCl_3$). δ 7.43 (d, 2H, J=8.7 Hz), 7.07 (d, 2H, J=8.7 Hz), 6.88-6.78 (m, 4H), 6.08 (s, 1H), 5.27 (s, 2H), 5.09 (s, 2H), 4.13 (t, 3H, J=6.6 Hz), 3.79 (s, 3H), 3.77 (s, 3H), 1.60-1.48 (m, 2H), 1.35-1.20 (m, 2H), 0.90 (t, 3H, J=7.2 Hz).

B. 1,3-Bis-(4-methoxy-benzyl)-2,6-dioxo-1,2,3,6-tetrahydro-pyrimidine-4-carboxylic acid (2-amino-ethyl)-amide (Cpd 21d). Compound 21c (390 mg, 0.86 mmol) and ethylene diamine (400 µl, 6 mmol) in 10 mL of toluene were refluxed for 4 hrs, cooled to rt, and concentrated under reduced pressure. The resultant residue was subjected to HPLC to give the di-TFA salt of 21d.

C. 1,3-Bis-(4-methoxy-benzyl)-2,6-dioxo-1,2,3,6-tetrahydro-pyrimidine-4-carboxylic acid (2-guanidino-ethyl)-amide (Cpd 157). The di-TFA salt of 21d (280 mg, 0.42 mmol) was dissolved in a mixture of 5 mL of MeCN and 1 mL of DIEA. Compound 1f (200 mg, 1.8 mmol) was added as one portion, the reaction mixture was allowed to stir overnight at room temperature, and then concentrated under reduced pressure. The resultant residue was subjected to HPLC, providing 59.4 mg of the di-TFA salt of Cpd 157. M+ (ES+)=481.2. $^1$H NMR (DMSO, $d_6$). δ 7.21 (d, 2H, J=8.6 Hz), 7.16 (d, 2H, J=8.6 Hz), 6.85 (d, 4H, J=8.7 Hz), 6.69 (s, 1H), 5.99 (s, 1H), 4.87 (s, 2H), 4.92 (s, 2H), 3.72 (s, 6H), 3.65-3.50 (m, 2H), 3.24 (broad s, 4H), 3.05-3.15 (m, 2H).

BIOLOGICAL EXAMPLES

Biological Example 1

Expression, Isolation, and Purification of Prokineticin-1

Recombinant N-terminal FLAG-tagged human prokineticin-1 (sequence-MRGATRVSIMLLLVTVSDCDYKDDDDKAVITGACERDVQCGAGTCCAISLWLRGLRMCTPLGREGEECHPGSHKVPFFRKRKHHTCPCLPNLLCSRFPDGRYRCSMDLK NINF) was expressed in stably transfected HEK 293 cells.

HEK 293 cells were grown to 100% confluence in DMEM selective high-glucose media (Invitrogen, Carlsbad, Calif.) containing 10% FBS, 20 mM HEPES, sodium pyruvate, penicillin and streptomycin (50 µg/ml each), and G418 (400 mg/L). The DMEM media used to culture the HEK 293 cells was replenished every other day with fresh media over a two-week period of time. Culture media containing the PK-1 peptide was collected, and filtered in 500 mL 0.2 µm pore size filters (Corning Incorporated, Corning, N.Y.). The filtrate was stored in a filtrate bottle at 4° C. The PK-1 peptide containing media was purified by gravity flow passage of media over M2 agarose columns (Sigma Chemical, St. Louis, Mo.) at 4° C. Following media passage, the agarose columns were washed with sterile 1×PBS (pH 7.4) until protein could no longer be detected by OD 280 nm. Columns were then eluted with a 0.1 M glycine-HCl solution at pH 2.8. The eluted material was immediately neutralized, by collecting into tubes containing 1M Tris pH8. Peak fractions were identified by OD 280 and pooled. The pooled fractions were subjected to Enterokinase cleavage of Flag epitope 4 units/mL overnight at room temperature. Enterokinase was removed, and sample aliquot was stored at −80° C.

Results of Mass Spectral Analysis of Prokineticin 1 Ligand from Above Purification The samples were analyzed using Maldi TOF-MS and LC-Electrospray-Mass Spectral Analysis.
Desired Protein Sequence:

AVITGACERDVQCGAGTCCAISLWLRGLRMCTPLGREGEECHPGSHKVP

FFRKRKHHTCPCLPNLLCSRFPDGRYRCSMDLKNINF

Calculated Avg. Molecular Mass=9667.4.
MALDI-TOF Analysis
Sample Preparation

The protein sample solution (10 µL) was desalted using a C4 Zip Tip according to the User Guide for Reversed-Phase ZipTip, 2002 Millipore Corporation.
Mass Spectrometry A Micromass TOF Spec E mass spectrometer was used to determine molecular mass. MassLynx software 3.4 was used for the system control and data acquisition. MALDI positive ion mass spectra were acquired over a mass range of 0-80,000 Da. The raw MS data were baseline subtracted and smoothed using Masslynx software and compared to the masses obtained from a reference standard.

Masses of eluting components were calculated using the Agilent deconvolution software.

Results

The mass spectral data shows the presence of the desired protein (molecular mass=9667) and an additional related component with a measured molecular mass of 9172 in about the same abundance based on mass spectral response. This mass agrees, within measurement error, with a possible truncation product missing the last four C-terminal residues indicated below.
Proposed Additional Protein Component Sequence

AVITGACERDVQCGAGTCCAISLWLRGLRMCTPLGREGEECHPGSHKVP

FFRKRKHHTCPCLPNLLCSRFPDGRYRCSMDLK

Calculated Avg. Molecular Mass=9178.8.

No other related protenaceous components were detected. The mass accuracy for all measurements is approximately 0.1%.

Biological Example 2

Functional Assay

Screening Procedure for PK1 Antagonists on the Fluorometric Imaging Plate Reader (FLIPR)

At a time of 24 h prior to running the assay, in cell culture media (DMEM containing high Glucose and L-glutamine, 10% FBS, 1% Pen/Streptomycin, 1% Sodium Pyruvate, 20 mM HEPES, Zeocin 200 mg/L), 100 µL of $1.3*10^6$/ml HEK 293 GPR73 (prokineticin 1 receptor) expressing cells were plated in a 96 well poly-d-lysine coated plate (Costar), and incubated at 37° C. and 5% $CO_2$. On the day in which the assay was run, the media was removed and 200 µL of 5× Calcium Plus Dye (Molecular Devices) which was previously resuspended with 200 mL of assay buffer [HBSS w/ $Ca^{2+}$ and $Mg^{2+}$ w/o phenol red, 20 mM HEPES, 0.1% BSA, 10 mL probenecid (710 mg probenecid in 5 mL of 1N NaOH, to which was then added 5 mL HBSS containing 20 mM HEPES)] was added to each well of the 96-well plate. The plate was incubated at 37° C. and 5% $CO_2$ for 30 min in dark. The plate was removed and allowed to reach RT for 15 min in the dark. The assay was then run on the FLIPR. In Brief: base line read for 1 min, compound added (25 μL) and incubated for 4 min, 15 seconds, PK1 ligand preparation added (25 μL) for a final concentration of a previously determined $EC_{50}$ and fluorescence was counted for 1 min, 45 seconds. Baseline is described as the amount of relative fluorescence read when buffer alone is added to cells. Baseline was subtracted from all wells. Percent of control was calculated as follows:

(Baseline subtracted well value is divided by baseline subtracted max value)*100.

Percent inhibition is 100 minus the percent of control value.

The $IC_{50}$ is defined as the amount of a given compound required to inhibit 50% of the maximum signal that is generated by the concentration of PK1 preparation used in our assay. $IC_{50}$ values were calculated using GraphPad Prism.

Table 2 includes data generated from the PK1 functional assay described in Example 2.

Biological and Mass Spectral Data

TABLE 2

| Cpd | $Ca^{2+}$ Mobilization IC50 (μM) | $Ca^{2+}$ Mobilization % Inh @10 μM | MS obs | MS calc |
|---|---|---|---|---|
| 1 | >10 | 30 | 411.9 | 412.19 |
| 2 | 0.125, 0.363, 0.336, 0.927* | 92, 85, 74, 87* | 424.3 | 424.21 |
| 3 | 4.96 | 52 | 452.0 | 452.20 |
| 4 | 2.5 | 71 | 438.0 | 438.23 |
| 5 | 2.18 | 67 | 390.1 | 390.23 |
| 6 | 2.59 | 59 | 414.0 | 414.19 |
| 7 | >10 | 52 | 462.0 | 462.19 |
| 8 | 3.85 | 64 | 450.1 | 450.26 |
| 9 | >10 | 35 | 438.9 | 439.18 |
| 10 | >10 | 33 | 440.2 | 440.20 |
| 11 | >10 | 32 | 395.2 | 395.19 |
| 12 | 0.034, 0.082, 0.247* | 97, 96, 94, 90* | 438.3 | 438.23 |
| 13 | 0.104, 0.256 | 92, 91 | 460.2 | 460.19 |
| 14 | >10 | 41 | 465.9 | 466.26 |
| 15 | 6.11 | 55 | 461.9 | 462.19 |
| 16 | 0.836 | 77 | 442.0 | 442.20 |
| 17 | 0.014, 0.033, 0.087* | 100, 99, 97 | 442.0 | 442.20 |
| 18 | 0.007, 0.028, 0.041, 0.022, 0.054* | 98, 100, 101, 99 | 492.0 | 492.13 |
| 19 | 0.862 | 81 | 477.8 | 478.18 |
| 20 | 3.69 | 61 | 454.0 | 454.22 |
| 21 | >10 | 43 | 454.0 | 454.22 |
| 22 | 0.947 | 80 | 436.9 | 437.21 |
| 23 | 1.25 | 74 | 450.9 | 451.22 |
| 24 | 0.041 | 99 | 456.0 | 456.22 |
| 25 | 0.137 | 94 | 437.9 | 438.23 |
| 26 | 0.354 | 88 | 437.9 | 438.23 |
| 27 | 1.97 | 55 | 508.2 | 508.13 |
| 28 | 0.71 | 101 | 517.1 | 517.13 |
| 29 | 0.042, 0.047 | 101, 102 | 505.8 | 506.15 |
| 30 | 0.009, 0.019 | 101, 103 | 457.8 | 458.17 |
| 31 | 0.009, 0.021 | 101, 102 | 453.9 | 454.22 |
| 32 | 0.601, 0.781 | 88, 86 | 519.7 | 520.16 |
| 33 | 2.86 | 66 | 455.9 | 456.22 |
| 34 | 0.515 | 89 | 519.7 | 520.16 |
| 35 | 0.061, 0.097, 0.113* | 100, 101, 101* | 519.7 | 520.16 |
| 36 | 1.32 | 77 | 545.8 | 546.18 |
| 37 | 0.038, 0.201, 0.326* | 98, 100, 98, 99* | 507.7 | 508.11 |
| 38 | 0.055, 0.178, 0.194* | 98, 94, 98* | 489.7 | 490.15 |
| 39 | 0.909 | 81 | 457.8 | 458.17 |
| 40 | 0.248 | 98 | 545.7 | 546.10 |
| 41 | 0.027, 0.047, 0.064* | 101, 100, 99* | 527.7 | 528.11 |
| 42 | 0.281 | 92 | 545.8 | 546.18 |
| 43 | >10 | 31 | 547.8 | 546.18 |
| 44 | 0.011, 0.046 | 100, 98 | 506.1 | 506.15 |
| 45 | 0.018 | 103 | 469.8 | 470.20 |
| 46 | 0.058 | 101 | 452.0 | 452.24 |
| 47 | 0.057 | 101 | 547.7 | 546.18 |
| 48 | 0.798 | 94 | 532.1 | 532.13 |
| 49 | 2 | 75 | 518.1 | 518.15 |
| 50 | 0.248 | 96 | 518.7 | 519.14 |
| 51 | 0.047 | 100 | 504.8 | 505.13 |
| 52 | 6.52 | 58 | 505.8 | 506.15 |
| 53 | 0.014, 0.025 | 99, 101 | 520.1 | 520.16 |
| 54 | 0.014, 0.006 | 98, 101 | 534.1 | 534.18 |
| 55 | 6.73 | 58 | 517.7 | 518.15 |
| 56 | 0.061 | 98 | 511.8 | 512.22 |
| 57 | 8.21 | 51 | 527.7 | 528.11 |
| 58 | 0.007, 0.016, 0.016* | 102, 99, 98* | 534.2 | 534.18 |
| 59 | 0.05, 0.035 | 99, 100 | 519.7 | 520.16 |
| 60 | 0.054 | 100 | 517.7 | 518.15 |
| 61 | 0.045 | 102 | 548.2 | 548.19 |
| 62 | 0.059 | 98 | 574.2 | 574.21 |
| 63 | 0.12 | 101 | 582.1 | 582.18 |
| 64 | 0.072 | 100 | 576.1 | 576.19 |
| 65 | 0.485 | 88 | 596.1 | 596.19 |
| 66 | 0.023 | 99 | 572.1 | 572.16 |
| 67 | 0.018 | 99 | 550.1 | 550.17 |
| 68 | 1.21 | 84 | 505.8 | 506.15 |
| 69 | 6.51 | 60 | 455.9 | 456.17 |
| 70 | 0.009, 0.007 | 101, 101 | 532.2 | 532.16 |
| 71 | 0.012, 0.007 | 100, 99 | 568.2 | 568.16 |
| 72 | 0.064 | 100 | 598.1 | 598.17 |
| 73 | 0.039 | 100 | 602.1 | 602.12 |
| 74 | 0.138 | 100 | 636.1 | 636.15 |
| 75 | 0.036 | 101 | 569.2 | 569.16 |
| 76 | 0.23 | 93 | 610.1 | 610.17 |
| 77 | 0.789 | 81 | 413.9 | 414.19 |
| 78 | 0.3 | 89 | 429.8 | 430.17 |
| 79 | 0.071 | 101 | 467.9 | 468.24 |
| 80 | 0.071 | 100 | 489.7 | 490.20 |
| 81 | 0.452 | 84 | 422.9 | 423.21 |
| 82 | 0.498 | 84 | 493.8 | 494.25 |
| 83 | 0.988 | 80 | 497.7 | 498.20 |
| 84 | 0.042 | 99 | 452.9 | 453.23 |
| 85 | 0.051 | 96 | 455.2 | 455.22 |
| 86 | 3.26 | 61 | 459.9 | 460.27 |
| 87 | >10 | 38 | 456.9 | 457.17 |
| 88 | 4.74 | 59 | 555.2 | 555.28 |
| 89 | 9.07 | 46 | 569.3 | 569.30 |
| 90 | 0.031, 0.043, 0.043* | 100, 100, 101* | 543.2 | 543.23 |
| 91 | 0.054 | 101 | 563.2 | 563.22 |
| 92 | 0.04 | 97 | 562.2 | 562.22 |
| 93 | 0.227 | 92 | 457.2 | 457.21 |
| 94 | 4.8 | 60 | 468.7 | 469.19 |
| 95 | 0.084 | 96 | 468.7 | 469.19 |
| 96 | >10 | 43 | 438.9 | 439.22 |
| 97 | 0.318 | 86 | 448.8 | 449.21 |
| 98 | >10 | 34 | 448.8 | 449.21 |
| 99 | 0.794 | 73 | 481.8 | 482.22 |
| 100 | 8.82 | 48 | 481.8 | 482.22 |
| 101 | >10 | 33 | 468.9 | 468.20 |
| 102 | 3.49 | 68 | 519.7 | 520.16 |
| 103 | 0.023 | 99 | 596.1 | 596.14 |
| 104 | 0.011, 0.011 | 99, 102 | 519.2 | 519.23 |
| 105 | 0.089 | 100 | 547.2 | 547.26 |
| 106 | 0.508 | 89 | 590.3 | 590.25 |
| 107 | 0.012 | 101 | 554.2 | 554.21 |
| 108 | 0.369 | 89 | 582.3 | 582.36 |
| 109 | 0.129 | 99 | 495.9 | 496.27 |
| 110 | 1.16 | 81 | 440.9 | 440.20 |

TABLE 2-continued

| Cpd | Ca$^{2+}$ Mobilization IC50 (μM) | Ca$^{2+}$ Mobilization % Inh @10 μM | MS obs | MS calc |
|---|---|---|---|---|
| 111 | 0.154 | 100 | 464.7 | 465.12 |
| 112 | 0.026 | 101 | 463.8 | 464.20 |
| 113 | 0.011, 0.024, 0.046, 0.076* | 101, 100, 102* | 505.8 | 506.15 |
| 114 | 0.041 | 99 | 524.2 | 524.20 |
| 115 | 0.047 | 99 | 514.2 | 514.26 |
| 116 | 0.057 | 99 | 510.2 | 510.26 |
| 117 | 0.084 | 79 | 532.2 | 532.25 |
| 118 | 0.006, 0.006 | 98, 102 | 536.2 | 536.22 |
| 119 | 0.006, 0.012 | 102, 99 | 536.2 | 536.22 |
| 120 | 0.009, 0.015 | 100, 102 | 532.2 | 532.25 |
| 121 | 0.020, 0.033 | 101, 98 | 498.2 | 498.26 |
| 122 | 1.08 | 78 | 443.1 | 443.17 |
| 123 | >10 | 34 | 404.0 | 404.24 |
| 124 | 1.56 | 74 | 416.0 | 416.24 |
| 125 | 0.487 | 83 | 438.9 | 439.22 |
| 126 | 0.115 | 95 | 576.3 | 576.31 |
| 127 | 0.058 | 100 | 602.1 | 602.21 |
| 128 | 0.04 | 100 | 534.2 | 534.23 |
| 129 | 4.78 | 64 | 427.8 | 428.16 |
| 130 | 1.87 | 71 | 417.9 | 418.14 |
| 131 | >10 | 32 | 496.3 | 495.9 |
| 132 | 8.5 | 54 | 556.2 | 556.2 |
| 133 | 0.2 | 93 | 564.2 | 564.22 |
| 134 | 0.019, 0.028 | 97, 97 | 546.2 | 546.23 |
| 135 | 0.013, 0.024 | 100, 94 | 520.2 | 520.22 |
| 136 | >10 | 50 | 470.2 | 470.23 |
| 137 | 0.015, 0.031 | 101, 98 | 470.2 | 470.23 |
| 138 | 1.34 | 70 | 642.2 | 642.26 |
| 139 | 0.018 | 95 | 533.2 | 533.24 |
| 140 | 0.455 | 89 | 512.2 | 512.24 |
| 141 | 1.84 | 73 | 417.9 | 417.85 |
| 142 | 0.323 | 90 | 500.1 | 500.22 |
| 143 | 0.006, 0.027 | 100, 101 | 440.1 | 440.20 |
| 144 | 1.33 | 77 | 514.2 | 514.23 |
| 145 | 0.461 | 86 | 467.9 | 468.24 |
| 146 | 0.67 | 87 | 482.0 | 482.25 |
| 147 | 808 | 82 | 520.3 | 520.10 |
| 148 | >10 | 41 | 465.9 | 465.56 |
| 149 | 4.78 | 64 | 427.8 | 427.89 |
| 150 | 1.87 | 71 | 417.9 | 417.85 |
| 151 | 0.003 | 99 | 484.2 | 484.21 |
| 152 | 0.009 | 97 | 482.2 | 482.23 |
| 153 | 0.013 | 99 | 484.2 | 484.24 |
| 154 | 0.003, 0.006 | 99, 98 | 484.2 | 484.24 |
| 155 | 0.016 | 99 | 470.2 | 470.23 |
| 156 | 0.004, 0.007 | 102, 99 | 456.2 | 456.21 |
| 157 | 0.197 | 92 | 481.2 | 480.21 |
| 158 | 0.254 | 93 | 453.9 | 453.49 |
| 159 | 0.013 | 98 | 469.8 | 469.56 |
| 160 | 0.616 | 89 | 452.0 | 451.22 |

*Where multiple values are displayed for a single compound. These values are representative of values determined upon multiple testing.

Biological Example 3

Effect of PK1 on Secretion and Gut Mucosal Ion Transport in Mammals

Methodology: Segments of ileum starting at a point 2 cm proximal to the ileocecal junction and extending 10 cm proximally were freshly excised, placed into Krebs-Ringer bicarbonate (KRB) solution, and emptied of their contents as a plastic rod was gently inserted into the intact segment. Ileal segments were scored with the back-edge of scalpel blade along the entire mesenteric border, and the intact muscular layers including the myenteric plexus were carefully removed with flat-head forceps. Three rectangular tissue sheets approximately 1.5 cm in length were prepared from the remaining muscle-stripped, mucosa-submucosa tissues and cut with care taken to avoid Peyer's patches. Each tissue sheet containing intact submucosal ganglia was pinned over a rectangular portal (total cross-sectional area of exposed mucosa=0.50 cm$^2$) between halves of an acrylic mounting cassette that was inserted between the tissue-bathing reservoirs of a modified Ussing-type flux chamber (Physiologic Instruments, Inc., San Diego, Calif.).

The apical (i.e., mucosal) and basolateral (i.e., serosal) surface of each tissue was bathed with 6 mL of an oxygenated KRB solution maintained at 36° C. Once mounted, tissues were allowed to equilibrate for 0.5-1 h before electrical field stimulation and addition of secretagogues or drugs. The KRB solution contained (in mM) 120 NaCl, 6 KCl, 1.2 MgCl$_2$, 1.2 NaH$_2$PO$_4$, 14.4 NaHCO$_3$, 2.5 CaCl$_2$, and 11.5 glucose or 11.5 mannitol. The KRB solution was continuously aerated with 95% O$_2$:5% CO$_2$ and maintained at pH 7.3. Each chamber was equipped with a pair of saturated KCl-agar bridges for measurement of transmural electrical potential difference (PD) across the tissue, and a pair of Ag—AgCl agar electrodes connected to an automated voltage-clamp device (model VCC MC6, or model VCC MC8, Physiologic Instruments, Inc., San Diego, Calif.) that compensated for solution resistance between the PD-sensing bridges and for deviations detected from a transmural potential difference (PD) across the tissues that were clamped at 0 mV. Tissue conductance (G) was calculated (in mS) by determining the current necessary to change PD by 1 mV using bipolar pulses from a pulse generator. Short-circuit current (Isc in μA), an index of net active ion transport, was measured continuously. Tissue conductance (Gt in mS), an index of the barrier function to passive flow of ions, was calculated from changes in Isc and the transepithelial potential difference for each tissue.

Baseline recordings of short-circuit current (Isc) and G for each tissue were acquired and recorded for an additional 15 min period prior to the start of an experimental protocol. Stimulated changes in Isc were measured and recorded continuously with a computerized data acquisition system (PowerLab 8SP, ADInstruments, Inc., Colorado Springs, Colo.). Neurally-evoked changes in Isc were obtained by application of electrical field stimulation (80V, 0.5 ms, 10 Hz, 5 s) from the outputs of an electronic stimulator (S-48, Grass-Telefactor, Astro-Med, Inc., West Warwick, R.I.) attached via aluminum foil electrodes placed in direct contact with the mucosal surface at opposite poles of each tissue. Pharmacological agents and secretagogues were routinely added to the basolateral-side reservoir. Agonist or secretagogue effects on Isc were continuously recorded following basolateral addition. Concentration-response curves were constructed from the cumulative, step-wise addition of pre-determined increasing amounts of agonist or secretagogue that were added at or near the peak Isc response to the preceding lower concentration. Effects of antagonists or inhibitors of secretion were evaluated after a 10-20 minute exposure period that was followed by challenge with a specific agonist or secretagogue.

Statistical Analysis. All values are reported as means±SE. Electrophysiological data obtained with Ussing flux-type chambers were normalized to tissue surface area and expressed per cm$^2$. Stimulated changes in ion transport were determined as the absolute difference between a baseline value prior to stimulation and the maximal response (ΔIsc) evoked by a given stimulus or secretagogue. An estimated EC$_{50}$ for the stimulatory action of PK1 on epithelial secretion was determined from a 7-point cumulative concentration-response test using a computer calculated curve-fitting function in PRISM (GraphPad Software, Inc.). An unpaired, two-tailed Student's t-test was used to determine statistical significance between any two groups, e.g., control and experimental tissues. Either an ANOVA in conjunction with a post hoc Neuman-Keuls multiple comparisons test, or a non-parametric Kruskal-Wallis ANOVA in conjunction with a post hoc Dunn's multiple comparisons test, was used to determine significant differences among multiple treatment groups. $P<0.05$ was considered statistically significant.

Summary of results from studies evaluating the mechanism of action of PK1 peptide. The basal Isc was $35.2\pm2.4$ $\mu A/cm^2$ and tissue conductance (G) was $33.7\pm0.9$ $mS/cm^2$ (n=79 tissues from 34 rats). Following a single-dose addition of PK1 to the Krebs solution bathing the basolateral tissue surface, Isc gradually increased to a peak value within 2-4 min and then declined back toward baseline within 10-15 min. The PK1-evoked increases in Isc were concentration dependent with an $EC_{50}$ of approximately 8.2 nM determined from cumulative concentration-response studies (see FIG. 1). The maximal response for the PK1-evoked response occurred at 100 nM; 100 nM PK1 evoked an increase in Isc of $28.7\pm2.9$ $\mu A/cm^2$ from baseline (n=42 tissues from 29 rats) and 10 nM PK1 evoked an increase of $13.5\pm2$. $\mu A/cm^2$ (n=33 tissues from 22 rats). The concentrations of 10 nM and 100 nM were used in all subsequent studies. PK1 had no significant effect on G in any of our studies. The pro-secretory effect of PK1 was not blocked in the presence of the nerve conduction toxin, Tetrodotoxin (TTX), or blockade of muscarinic receptors present on mucosal enterocytes by the anti-cholinergic drug, Atropine, indicating that the its action is not dependent on intrinsic neural activity in the tissues. The PK1 evoked increase in Isc requires the presence of endogenous PK1 receptors since exogenous PK1 peptide added to ileum mucosal tissues from PK1 receptor knock-out mice failed to elicit a significant change in Isc compared to wild-type littermates.

Biological Example 4

Effect of Prokineticin 1 Peptide on Gut Mucosal Ion Transport Ex Vivo

Figure 2:
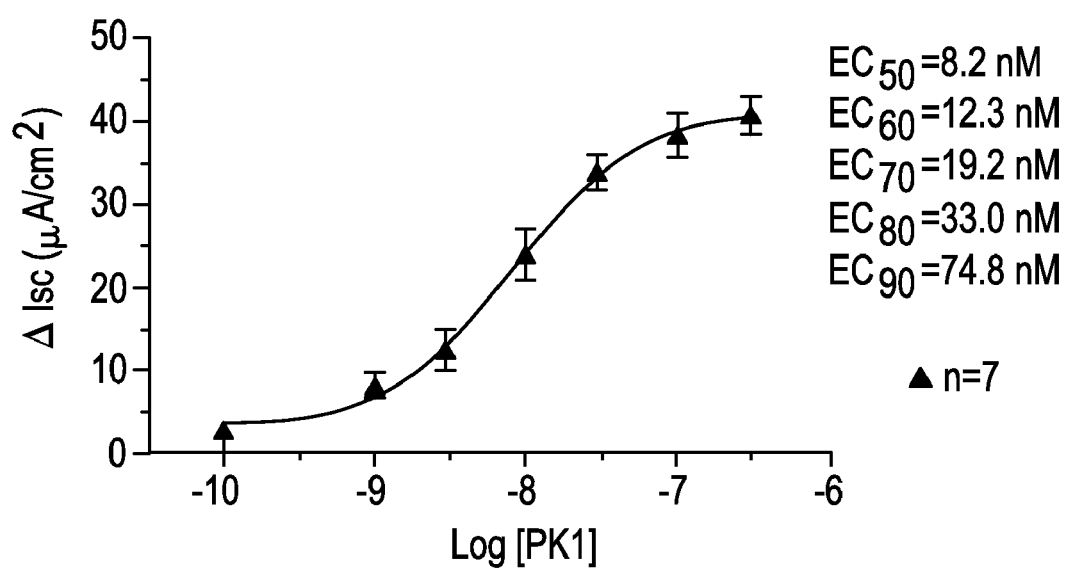
FIG. 2 shows the cumulative concentration-response curve evoked in the short-circuit current (Isc) response to Prokineticin 1 (PK1) peptide in PK1 exposed rat ileal tissues mounted in Ussing-type ion flux chambers.

FIG. 2 illustrates the cumulative concentration-response curve evoked in the short-ciruit current (Isc) response to Prokineticin 1 (PK1) peptide in PK1 exposed rat ileal tissues mounted in Ussing-type ion flux chambers. Change in Isc is reported as the difference between the peak Isc response to PK1 at a given concentration compared to the initial baseline (unstimulated) Isc value and expressed as ΔIsc measured in microAmps ($\mu A$) corrected for the surface area (in $cm^2$) of the tissue mounted in the Ussing-type chamber. An $EC_{50}$ value for the response curve was calculated as described below in methodology.

Methodology. The basic methodology for Ussing-type ion flux chambers used in these studies was the same as that described in detail above with the following modifications to the experimental protocol. Following a 30-45 minute equilibration period, baseline-stable tissues were subjected to a train of electrical field stimulation (EFS; 80 V, 0.5 ms, 10 Hz, 5 s) applied from contacts connecting the foil electrodes on opposite poles of the tissue to the polarized, isolated outputs from an electronic square-pulse stimulator. The responses to two sequential EFS were used to gauge tissue viability and comparability of the responses of individual tissues from each rat and between rats. Tissue conductance was measured at periodic intervals as changes in the amplitudes of brief short-circuit current responses evoked by application of 1 mV amplitude bi-polar pulses from a pulse generator using Ohm's Law. Three to four tissues from each rat were studied. The tissues from a given animal will be grouped and assigned accordingly: one control tissue which received only vehicle followed by two consecutive doses of PK-1 ligand added in a cumulative fashion to the basolateral surface of the tissue; the remaining two to three tissues from the same animal were assigned to be exposed to a given PK-1 receptor antagonist (e.g., 3-4 tissues from 1 rat: Control, Antagonist$_1$, Antagonist$_2$, and/or Antagonist$_3$). Test compound was added to the basolateral tissue side reservoir at a final concentration of 1 $\mu M$ and allowed a 15 minute incubation period prior to challenge with the PK1 peptide. At the end of this 15 min exposure period, PK1 ligand at 10 and 100 nM was added in a cumulative fashion to each tissue to characterize the inhibitory effect of the test compound. At the conclusion of the experiment, EFS was re-applied to gauge tissue viability and stability of responsiveness.

Figure 3:
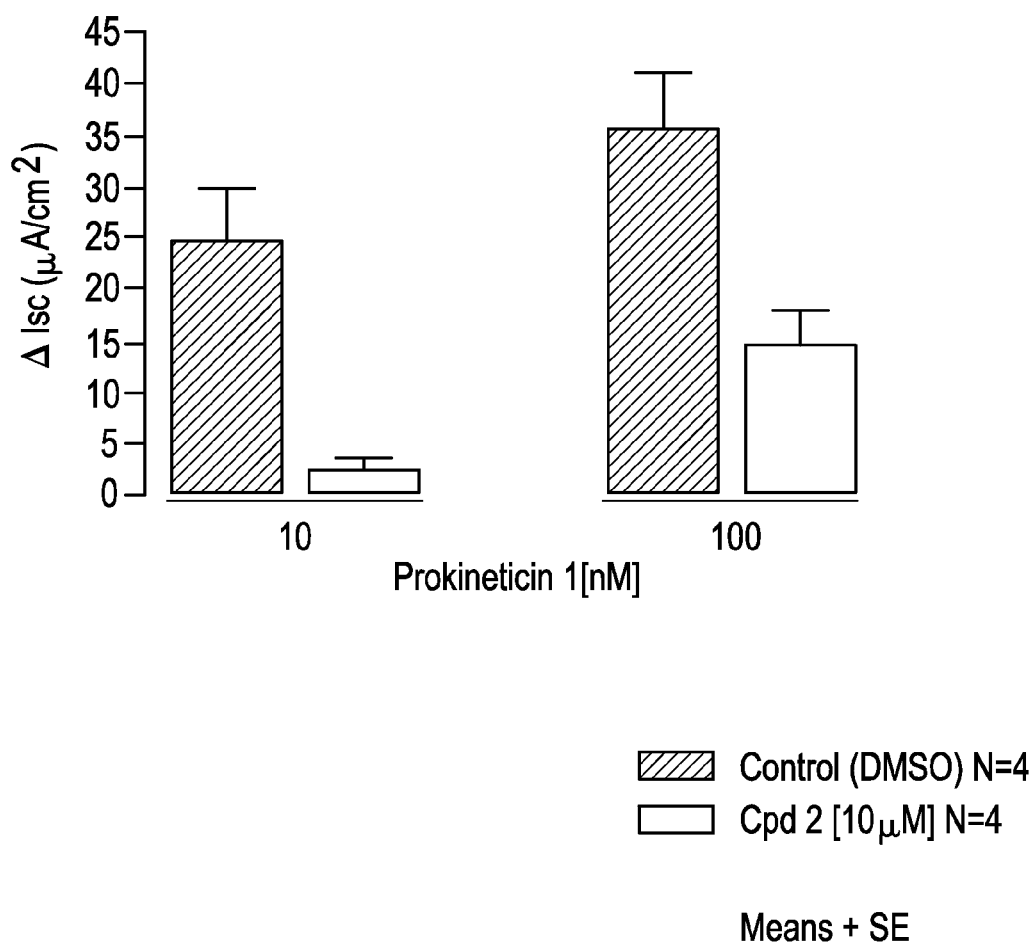
FIG. 3 shows the inhibition of the PK1-evoked increase in Isc by Cpd 2 of Formula (I).
Figure 4:
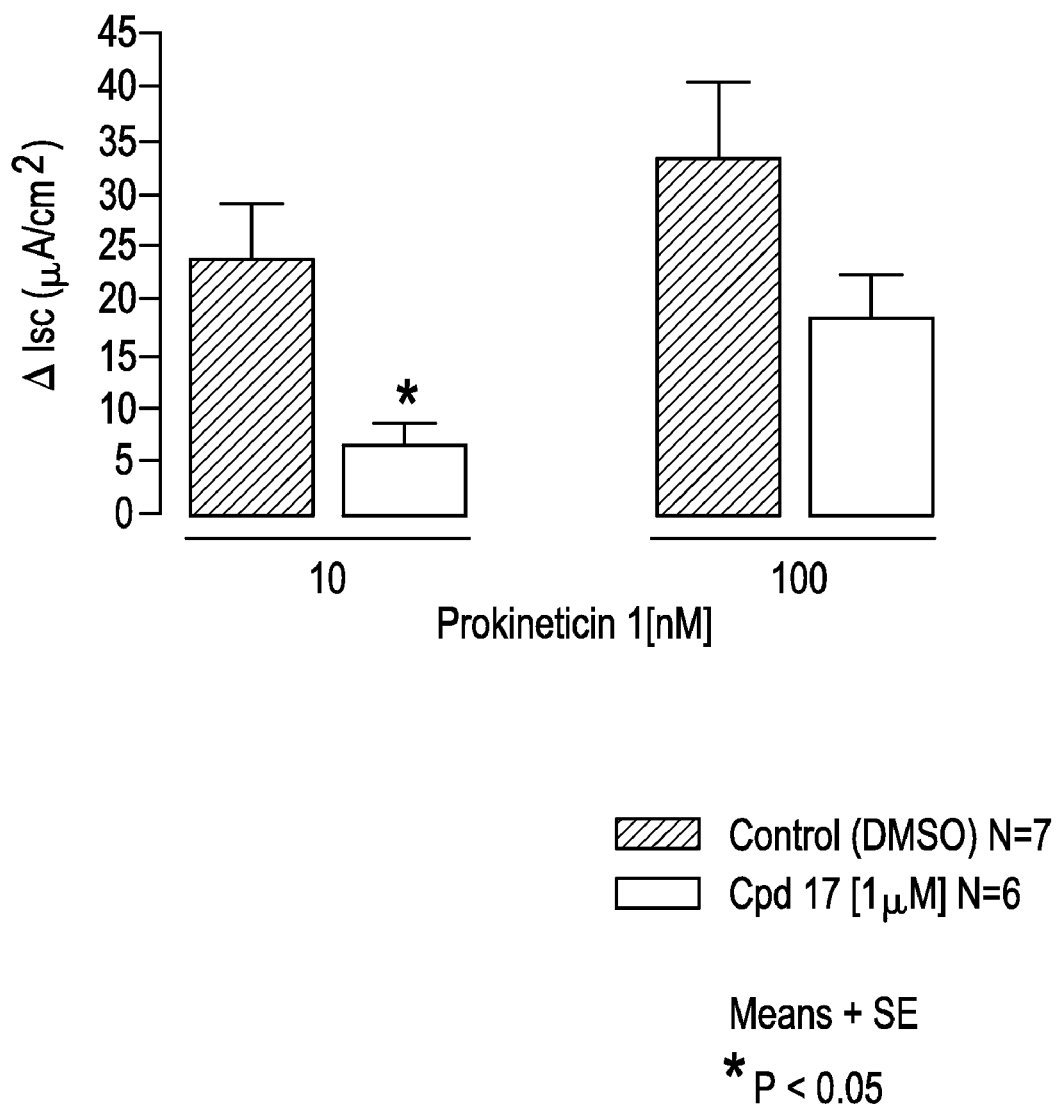
FIG. 4 shows the inhibition of the PK1-evoked increase in Isc by Cpd 17 of Formula (I).
Figure 5:
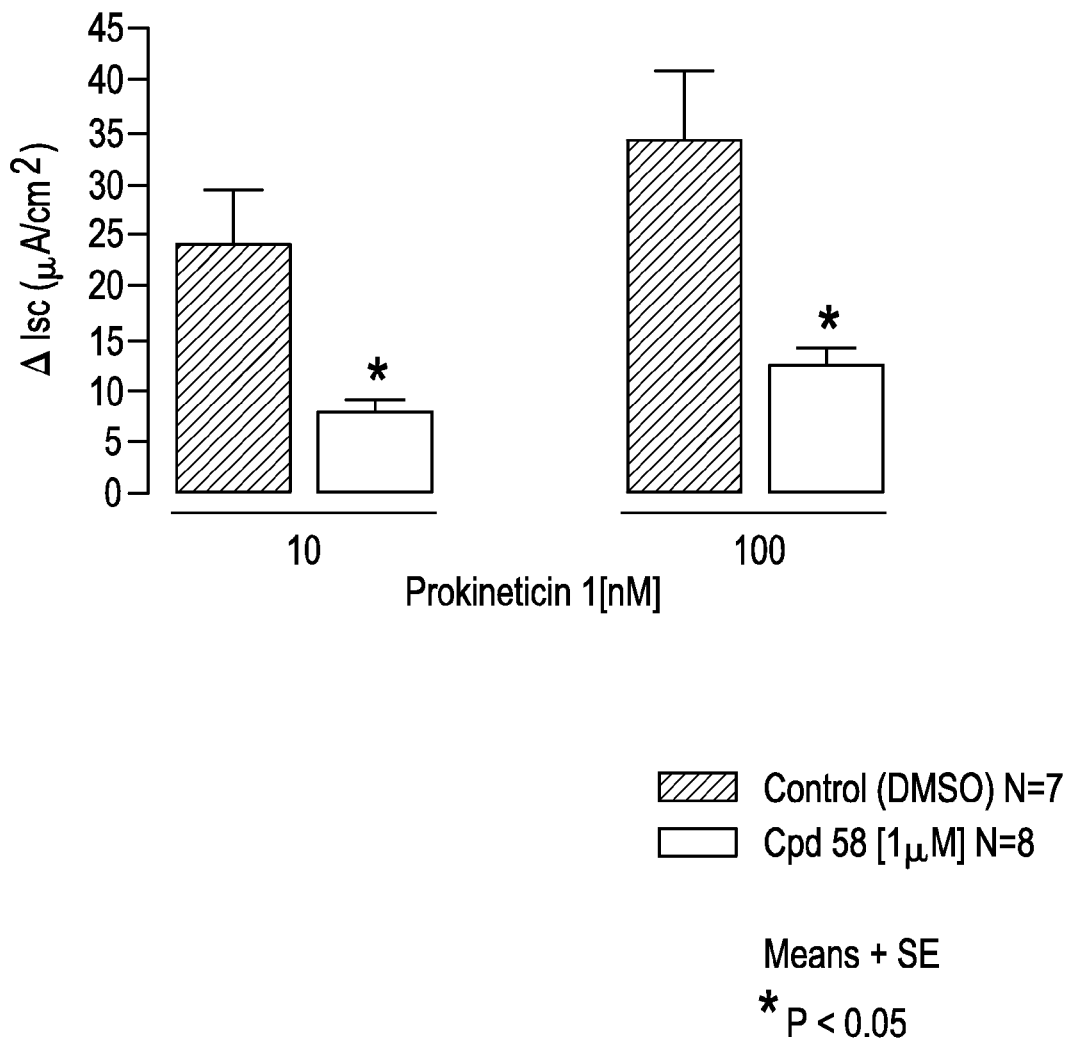
FIG. 5 shows the inhibition of the PK1-evoked increase in Isc by Cpd 58 of Formula (I).

Summary of results. Pre-treatment of tissues with PK1 antagonists alone had no measurable effect on baseline Isc and tissue conductance (G). The results indicate that inhibition of the PK1 evoked increase in Isc in isolated rat ileum mucosa was successfully achieved in the presence of the guanidine small molecule antagonists, Cpd 2, Cpd 17, and Cpd 58, that were all identified using a functional cell based screening assay (i.e., mobilization of intracellular $Ca^{2+}$) as putative antagonists at the PK1 receptor. In trials with this compound, the observed suppression of the Isc response evoked by two ascending cumulative concentrations of PK1 showed characteristics of a significant surmountable antagonism (see FIGS. 3, 4 and 5). These data strongly suggest that good efficacy can be achieved in the selective functional blockade of the PK1 receptor by small molecule inhibitors to modulate the pro-secretory effect of PK1 on the intestinal epithelium. These data suggest the potential for the efficacious use of PK1 receptor antagonists of Formula (I) in gut disease states that include a significant secretory diarrhea component.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:
1. A compound of Formula (I):

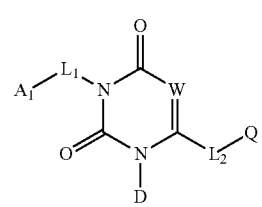

Formula (I)

wherein:
A$_1$ is hydrogen; aryl; heteroaryl; C$_{5-8}$cycloalkyl; or heterocyclyl; provided that A$_1$ is other than piperidin-4-yl, N-t-butoxycarbonyl-piperidin-4-yl, or N-methyl-piperidin-3-yl; and wherein substituents of A$_1$ other than hydrogen are optionally substituted with one to three substituents independently selected from the group consisting of C$_{1-6}$alkyl, hydroxy(C$_{1-6}$)alkyl, C$_{1-6}$alkoxy, halogen, nitro, halogenated C$_{1-6}$alkyl, halogenated C$_{1-6}$alkoxy, C$_{1-6}$alkylthio, C$_{1-6}$alkoxycarbonyl, amino, C$_{1-6}$alkylamino, di(C$_{1-6}$alkyl)amino, cyano, hydroxy, aminocarbonyl, C$_{1-6}$alkylaminocarbonyl, di(C$_{1-6}$alkyl)aminocarbonyl, C$_{1-6}$alkoxycarbonylamino, C$_{1-6}$alkylcarbonyl, C$_{1-6}$alkylthiocarbonyl, formyl, C$_{1-6}$alkylsulfonyl, $C_{1-6}$alkylsulfonylamino, aminosulfonyl, $C_{1-6}$alkylaminosulfonyl, and di($C_{1-6}$alkyl)aminosulfonyl;

$L_1$ is —$(CH_2)_r$— or —$CH_2CH_2X(CH_2)_s$—, optionally substituted with one to three substitutents independently selected from the group consisting of $C_{1-6}$alkyl, $C_{2-6}$alkenyl, $C_{2-6}$alkynyl, and halogen; provided that when $A_1$ is hydrogen, r is greater than or equal to 4;

r is an integer of 1 to 5;

s is an integer of 1 to 3;

X is O or S;

D is —P-$A_2$; wherein when $A_2$ is hydrogen, P is —$(CH_2)_{4-6}$—, and when $A_2$ is other than hydrogen, P is —$(CH_2)_{1-2}$— or —$CH_2CH=CH$—;

$A_2$ is hydrogen; benzodioxalyl; heteroaryl other than unsubstituted pyridin-2-yl; $C_{3-8}$cycloalkyl; or phenyl optionally substituted at the meta and para positions with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, $C_{1-6}$alkylamino, di($C_{1-6}$alkyl)amino, cyano, hydroxy, nitro, $C_{1-6}$alkylcarbonyl, $C_{1-6}$alkylthiocarbonyl, aminocarbonyl, $C_{1-6}$alkylaminocarbonyl, di($C_{1-6}$alkyl)aminocarbonyl, $C_{1-6}$alkylcarbonylamino, and a non fused $C_{3-6}$cycloalkyloxy; wherein benzodioxalyl, heteroaryl, and $C_{3-8}$cycloalkyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, $C_{1-6}$alkylamino, di($C_{1-6}$alkyl)amino, cyano, hydroxy, nitro, $C_{1-6}$alkylcarbonyl, $C_{1-6}$alkylthiocarbonyl, aminocarbonyl, $C_{1-6}$alkylaminocarbonyl, di($C_{1-6}$alkyl)aminocarbonyl, $C_{1-6}$alkylcarbonylamino, and a non fused $C_{3-6}$cycloalkyloxy;

provided that no more than two substituents on $A_2$ are aryl($C_{1-6}$)alkoxy, phenyl, or a non fused $C_{3-6}$cycloalkyloxy;

provided that when $A_1$ is unsubstituted phenyl and $L_2$ is —$X_1$—$CH(R^x)$—$(CR^yR^z)$— wherein $X_1$ is NH, and $R^x$, $R^y$, and $R^z$ are each hydrogen, $A_2$ is other than unsubstituted phenyl; phenyl substituted with aryl($C_{1-6}$)alkoxy or phenyl; or phenyl substituted at the meta position with cyano;

and, further provided that when $A_1$ is unsubstituted phenyl and $L_2$ is —$X_1$—$CH(R^x)$—$(CR^yR^z)_2$— wherein $X_1$ is NH and $R^x$, $R^y$, and $R^z$ are each hydrogen, $A_2$ is other than phenyl substituted with methoxy;

and, provided that when $A_1$ is 3,4-dichloro-phenyl and P is —$CH_2$—, $A_2$ is other than phenyl substituted at the meta position with trifluoromethyl or trifluoromethoxy;

and, further provided that when $A_1$ is 3,4-dichloro-phenyl and P is —$(CH_2)_2$—, $A_2$ is other than 4-methoxy-phenyl;

W is $C(R_W)$; wherein $R_W$ is H or $C_{1-2}$alkyl;

$L_2$ is a bivalent radical selected from the group consisting of pyrrolidinyl or piperidinyl attached to the triazine ring of Formula (I) via its nitrogen atom, wherein said pyrrolidinyl or piperidinyl is substituted on a carbon atom with —$(CH_2)_{0-2}$—;

—NH—$C_{5-7}$cycloalkyl-$(CH_2)_{0-2}$—; provided that when $C_{5-7}$cycloalkyl is cyclohexyl, Q is attached at either the 2- or cis-4-position relative to the position of —NH—;

—$X_1$—$(CH_2)_u$—$X_2$—$(CH_2)_v$—; wherein u is an integer of 1 to 3; and wherein v is an integer of 1 to 4; provided that when $X_1$ is a direct bond and W is $C(R_W)$, then u is 1 and v is 2 to 4;

—$X_2$—$(CH_2)_{0-4}$—;

—$X_1$—$(CH_2)_{2-3}$—$X_3$—$(CH_2)_{2-3}$—;

—$NH(CH_2)_{1-4}C(=O)$—, provided that at least one of $R^b$, $R^c$, or $R^d$ is other than hydrogen and m is 0;

—$NHC(=O)$—$(CH_2)_{1-4}$—;

—$C(=O)NH(CR^yR^z)_{2-5}$—;

and

—$X_1$—$CH(R^x)$—$(CR^yR^z)_{1-5}$—; such that when $X_1$ is a direct bond and W is $C(R_w)$, then $R^x$ is hydrogen;

wherein $X_1$ is —NH—, O, S, or a direct bond, such that $X_1$ is other than O when W is N;

$X_2$ is —CH=CH—;

$X_3$ is O, S, NH, or C=O;

$R^x$, $R^y$, and $R^z$ are independently H or $C_{1-4}$alkyl;

and provided that $L_2$ in any instance does not exceed 7 atoms in length;

and further provided that when $L_2$ is —$X_2$—$(CH_2)_{0-4}$— or —$C(=O)NH(CR^yR^z)_{2-5}$—, then $R_W$ is hydrogen;

Q is —(O)—,N($R^a$)-G; and m is 0 or 1;

G is —$C(=NR^b)NR^cR^d$;

$R^a$ and $R^d$ are independently hydrogen, $C_{1-6}$alkyl, $C_{2-6}$alkenyl, or $C_{3-6}$alkynyl, wherein substituents of $R^a$ and $R^d$ other than hydrogen are optionally substituted with one to three substituents independently selected from the group consisting of hydroxy, $C_{1-4}$alkoxy, fluoro, amino, $C_{1-4}$alkylamino, di$C_{1-4}$alkylamino, and $C_{1-4}$alkylcarbonyl; or $R^a$ and $R^c$ are taken together with the atoms to which they are attached to form a 5-8 membered monocyclic ring optionally substituted with oxo;

$R^b$ is hydrogen, $C_{1-6}$alkyl, $C_{2-6}$alkenyl, $C_{3-6}$alkynyl, $C_{2-6}$alkoxycarbonyl, or cyano; or, $R^b$ and $R^c$ are taken together with the atoms to which they are attached to form a 5-8 membered monocyclic ring, optionally substituted with oxo;

$R^c$ is hydrogen, $C_{1-10}$alkyl, $C_{2-10}$alkenyl, $C_{3-10}$alkynyl, $C_{3-7}$cycloalkyl, adamantyl, amino, $C_{1-6}$alkylamino, di($C_{1-6}$alkyl)amino, $C_{1-6}$alkylcarbonyl, $C_{1-6}$alkoxycarbonyl, arylcarbonyl, heteroarylcarbonyl, heterocyclylcarbonyl, aryl, heteroaryl, or heterocyclyl; wherein $C_{1-10}$alkyl, $C_{2-10}$alkenyl, and $C_{2-10}$alkynyl are optionally substituted with one to three substituents independently selected from the group consisting of hydroxy, $C_{1-6}$alkoxy, trifluoromethyl, aryl, heteroaryl, and heterocyclyl; and wherein any aryl- or heteroaryl-containing substituents of $R^c$ are optionally substituted with one to three substituents independently selected from the group consisting of $C_{1-6}$alkyl, $C_{1-6}$alkoxy, halogen, fluorinated $C_{1-6}$alkyl, fluorinated $C_{1-6}$alkoxy, $C_{1-6}$alkylcarbonyl, $C_{1-6}$alkoxycarbonyl, aminocarbonyl, $C_{1-6}$alkylaminocarbonyl, di($C_{1-6}$alkyl)aminocarbonyl, $C_{1-6}$alkoxycarbonylamino, formyl, $C_{1-6}$alkylsulfonyl, $C_{1-6}$alkylsulfonylamino, aminosulfonyl, $C_{1-6}$alkylaminosulfonyl, and di($C_{1-6}$alkyl)aminosulfonyl, nitro, methylthio, hydroxy, and cyano; or, $R^c$ and $R^d$ are taken together with the atoms to which they are attached to form a 5-8 membered monocyclic ring that optionally includes 1 to 2 O or S heteroatoms within the ring, and said ring is optionally substituted with oxo;

with the proviso that in any instance, only one ring optionally exists between $R^a$ and $R^b$, $R^b$ and $R^c$, or $R^c$ and $R^d$;

and an enantiomer, a diastereomer, a tautomer, or a pharmaceutically acceptable salt thereof.

2. The compound according to claim 1 wherein $A_1$ is hydrogen; aryl; heteroaryl; or $C_{5-8}$cycloalkyl; wherein substituents of $A_1$ other than hydrogen are optionally substituted with one to three substituents independently selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, $C_{1-6}$alkylamino, di($C_{1-6}$alkyl)amino, cyano, hydroxy, aminocarbonyl, $C_{1-6}$alkylaminocarbonyl, di($C_{1-6}$alkyl)aminocarbonyl, $C_{1-6}$alkoxycarbonylamino, $C_{1-6}$alkylcarbonyl, $C_{1-6}$alkylthiocarbonyl, formyl, $C_{1-6}$alkylsulfonyl, $C_{1-6}$alkylsulfonylamino, aminosulfonyl, $C_{1-6}$alkylaminosulfonyl, and di($C_{1-6}$alkyl)aminosulfonyl.

3. The compound according to claim 1 wherein $A_1$ is hydrogen; aryl; heteroaryl; $C_{5-8}$cycloalkyl; or heterocyclyl; provided that $A_1$ is other than piperidin-4-yl, N-t-butoxycarbonyl-piperidin-4-yl, or N-methyl-piperidin-3-yl; and wherein substituents of $A_1$ other than hydrogen are optionally substituted with one to three substituents independently selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, cyano, hydroxy, aminocarbonyl, $C_{1-6}$alkylaminocarbonyl, di($C_{1-6}$alkyl)aminocarbonyl, and $C_{1-6}$alkylcarbonyl.

4. The compound according to claim 1 wherein $A_1$ is hydrogen; aryl; heteroaryl; $C_{5-8}$cycloalkyl; or heterocyclyl other than piperidinyl; wherein substituents of $A_1$ other than hydrogen are optionally substituted with one to three substituents independently selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, cyano, hydroxy, aminocarbonyl, $C_{1-6}$alkylaminocarbonyl, di($C_{1-6}$alkyl)aminocarbonyl, and $C_{1-6}$alkylcarbonyl.

5. The compound according to claim 1 wherein $A_1$ is hydrogen, substituted phenyl, benzofuranyl, furanyl, thiazolyl, thiophenyl, or cyclopentyl; wherein substituents of $A_1$ other than hydrogen are optionally substituted and phenyl is substituted with one to two substituents independently selected from the group consisting of $C_{1-4}$alkyl, $C_{1-4}$alkoxy, halogen, nitro, halogenated $C_{1-4}$alkyl, halogenated $C_{1-4}$alkoxy, methylthio, $C_{1-4}$alkoxycarbonyl, amino, cyano, hydroxy, aminocarbonyl, and $C_{1-4}$alkylcarbonyl.

6. The compound according to claim 1 wherein $A_1$ is substituted phenyl, benzofuranyl, thiazolyl, or thiophenyl; wherein phenyl is substituted with, and benzofuranyl, thiazolyl, and thiophenyl are optionally substituted with one to two substituents independently selected from the group consisting of $C_{1-4}$alkyl, $C_{1-4}$alkoxy, halogen, nitro, halogenated $C_{1-4}$alkyl, halogenated $C_{1-4}$alkoxy, methylthio, amino, cyano, and $C_{1-4}$alkylcarbonyl.

7. The compound according to claim 1 wherein $A_1$ is phenyl or benzofuranyl; wherein phenyl is substituted at either the 4-position or 3- and 4-positions with one to two substituents independently selected from the group consisting of ethyl, methoxy, fluoro, chloro, nitro, difluoromethoxy, and methylthio.

8. The compound according to claim 1 wherein $L_1$ is $-(CH_2)_r-$, optionally substituted with one to three substituents independently selected from the group consisting of $C_{1-6}$alkyl, $C_{2-6}$alkenyl, $C_{2-6}$alkynyl, and halogen; provided that when $A_1$ is hydrogen, r is greater than or equal to 4.

9. The compound according to claim 1 wherein $L_1$ is $-(CH_2)_r-$, optionally substituted with a substituent selected from the group consisting of $C_{1-4}$alkyl, $C_{2-4}$alkenyl, and $C_{2-4}$alkynyl; provided that r is 1 to 3 when $A_1$ is other than hydrogen; or r is greater than or equal to 4 when $A_1$ is hydrogen.

10. The compound according to claim 1 wherein $L_1$ is $-(CH_2)_r-$ optionally substituted with a substituent selected from the group consisting of methyl and allyl; provided that r is 1 to 3 when $A_1$ is other than hydrogen.

11. The compound according to claim 1 wherein $L_1$ is $-CH_2-$ optionally substituted with methyl or allyl.

12. The compound according to claim 1 wherein $A_2$ is hydrogen, heteroaryl other than unsubstituted pyridin-2-yl, $C_{3-8}$cycloalkyl, or phenyl optionally substituted at the meta and para positions with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, cyano, hydroxy, nitro, aminocarbonyl, $C_{1-6}$alkylcarbonylamino, and a non fused $C_{3-6}$cycloalkyloxy; wherein heteroaryl other than unsubstituted pyridin-2-yl and $C_{3-8}$cycloalkyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, cyano, hydroxy, nitro, aminocarbonyl, $C_{1-6}$alkylcarbonylamino, and a non fused $C_{3-6}$cycloalkyloxy;

provided that no more than two substituents on $A_2$ are aryl($C_{1-6}$)alkoxy, phenyl, or a non fused $C_{3-6}$cycloalkyloxy;

provided that when $A_1$ is unsubstituted phenyl and $L_2$ is $-X_1-CH(R^x)-(CR^yR^z)-$ wherein $X_1$ is NH and $R^x$, $R^y$, and $R^z$ are each hydrogen, $A_2$ is other than unsubstituted phenyl; phenyl substituted with aryl($C_{1-6}$)alkoxy or phenyl; or phenyl substituted at the meta position with cyano;

and, further provided that when $A_1$ is unsubstituted phenyl and $L_2$ is $-X_1-CH(R^x)-(CR^yR^z)_2-$ wherein $X_1$ is NH and $R^x$, $R^y$, and $R^z$ are each hydrogen, $A_2$ is other than phenyl substituted with methoxy;

and, provided that when $A_1$ is 3,4-dichloro-phenyl and P is $-CH_2-$, $A_2$ is other than phenyl substituted at the meta position with trifluoromethyl or trifluoromethoxy;

and, further provided that when $A_1$ is 3,4-dichloro-phenyl and P is $-(CH_2)_2-$, $A_2$ is other than 4-methoxy-phenyl; and in addition, when $A_2$ is hydrogen, P is $-(CH_2)_{4-6}-$, and when $A_2$ is other than hydrogen, P is $-(CH_2)_{1-2}-$ or $-CH_2CH=CH-$.

13. The compound according to claim 1 wherein $A_2$ is a heteroaryl other than unsubstituted pyridin-2-yl, a non fused $C_{3-8}$cycloalkyl, or phenyl optionally substituted at the meta and para positions with one to three substituents independently selected from the group consisting of $C_{1-6}$alkyl, $C_{1-6}$alkoxy, halogen, halogenated $C_{1-6}$alkyl, halogenated $C_{1-6}$alkoxy, $C_{1-6}$alkylthio, $C_{1-6}$alkoxycarbonyl, amino, hydroxy, nitro, aminocarbonyl, $C_{1-6}$alkylcarbonylamino, and a non fused $C_{3-6}$cycloalkyloxy; wherein heteroaryl other than unsubstituted pyridin-2-yl and a non fused $C_{3-8}$cycloalkyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, $C_{1-6}$alkylthio, $C_{1-6}$alkoxycarbonyl, amino, hydroxy, nitro, aminocarbonyl, $C_{1-6}$alkylcarbonylamino, and a non fused $C_{3-6}$cycloalkyloxy;

provided that no more than two substituents on $A_2$ are non fused $C_{3-6}$cycloalkyloxy;

provided that when A$_1$ is unsubstituted phenyl and L$_2$ is —X$_1$—CH(R$^x$)—(CR$^y$R$^z$)— wherein X$_1$ is NH and R$^x$, R$^y$, and R$^z$ are each hydrogen, A$_2$ is other than unsubstituted phenyl;

and, further provided that when A$_1$ is unsubstituted phenyl and L$_2$ is
—X$_1$—CH(R$^x$)—(CR$^y$R$^z$)$_2$— wherein X$_1$ is NH and R$^x$, R$^y$, and R$^z$ are each hydrogen, A$_2$ is other than phenyl substituted with methoxy;

and, provided that when A$_1$ is 3,4-dichloro-phenyl, A$_2$ is other than phenyl substituted at the meta position with trifluoromethyl or trifluoromethoxy;

and, further provided that when A$_1$ is 3,4-dichloro-phenyl and P is —(CH$_2$)$_2$—, A$_2$ is other than 4-methoxy-phenyl.

14. The compound according to claim 1 wherein A$_2$ is furanyl, pyridin-3-yl, pyridin-4-yl, or phenyl optionally substituted at the meta and para positions with one to three substituents independently selected from the group consisting of C$_{1-4}$-alkyl, C$_{1-4}$alkoxy, halogen, halogenated C$_{1-3}$alkoxy, C$_{1-3}$alkylthio, hydroxy, amino, aminocarbonyl, C$_{1-3}$alkylcarbonylamino, and a non fused C$_{3-6}$cycloalkyloxy; and wherein furanyl, pyridin-3-yl, and pyridin-4-yl are optionally substituted with one to three substituents independently selected from the group consisting of C$_{1-4}$alkyl, C$_{1-4}$alkoxy, halogen, halogenated C$_{1-3}$alkoxy, C$_{1-3}$alkylthio, hydroxy, amino, aminocarbonyl, C$_{1-3}$alkylcarbonylamino, and a non fused C$_{3-6}$cycloalkyloxy;

provided that no more than two substituents on A$_2$ are non fused C$_{3-6}$cycloalkyloxy;

provided that when A$_1$ is unsubstituted phenyl and L$_2$ is —X$_1$—CH(R$^x$)—(CR$^y$R$^z$)— wherein X$_1$ is NH and R$^x$, R$^y$, and R$^z$ are each hydrogen, A$_2$ is other than unsubstituted phenyl;

and, further provided that when A$_1$ is unsubstituted phenyl and L$_2$ is
—X$_1$—CH(R$^x$)—(CR$^y$R$^z$)$_2$— wherein X$_1$ is NH and R$^x$, R$^y$, and R$^z$ are each hydrogen, A$_2$ is other than phenyl substituted with methoxy;

and, provided that when A$_1$ is 3,4-dichloro-phenyl, A$_2$ is other than phenyl substituted in the meta position with trifluoromethoxy.

15. The compound according to claim 1 wherein A$_2$ is pyridin-3-yl, pyridin-4-yl, or phenyl optionally substituted at the meta and para positions with one to two substituents independently selected from the group consisting of methyl, ethyl, methoxy, ethoxy, isopropyloxy, trifluoromethoxy, difluoromethoxy, hydroxy, aminocarbonyl, and methylcarbonylamino;

wherein pyridin-3-yl and pyridin-4-yl are optionally substituted with one to two substituents independently selected from the group consisting of methyl, ethyl, methoxy, ethoxy, isopropyloxy, trifluoromethoxy, difluoromethoxy, hydroxy, aminocarbonyl, and methylcarbonylamino;

provided that when A$_1$ is unsubstituted phenyl and L$_2$ is
—X$_1$—CH(R$^x$)—(CR$^y$R$^z$)— wherein X$_1$ is NH and R$^x$, R$^y$, and R$^z$ are each hydrogen, A$_2$ is other than unsubstituted phenyl;

and, further provided that when A$_1$ is unsubstituted phenyl and L$_2$ is
—X$_1$—CH(R$^x$)—(CR$^y$R$^z$)$_2$— wherein X$_1$ is NH and R$^x$, R$^y$, and R$^z$ are each hydrogen, A$_2$ is other than phenyl substituted with methoxy;

and, further provided that when A$_1$ is 3,4-dichloro-phenyl, A$_2$ is other than phenyl substituted at the meta position with trifluoromethoxy.

16. The compound according to claim 1 wherein A$_2$ is phenyl substituted at the para position with a substituent selected from the group consisting of methoxy, ethoxy, isopropyloxy, difluoromethoxy, hydroxy, and aminocarbonyl; or A$_2$ is pyridin-3-yl or pyridin-4-yl substituted with methoxy.

17. The compound according to claim 1 wherein P is —CH$_2$—.

18. The compound according to claim 1 wherein W is N or C(R$_W$) wherein R$_W$ is H.

19. The compound according to claim 1 wherein L$_2$ is a bivalent radical selected from the group consisting of
—NH—C$_{5-7}$cycloalkyl-(CH$_2$)$_{0-2}$—; such that when C$_{5-7}$cycloalkyl is cyclohexyl, Q is attached at either the 2- or cis-4-position relative to the position of —NH—;
—X$_2$—(CH$_2$)$_{0-4}$—;
—X$_1$—(CH$_2$)$_{2-3}$—X$_3$—(CH$_2$)$_{2-3}$—;
—NH(CH$_2$)$_{1-4}$C(=O)— provided that at least one of R$^b$, R$^c$, or R$^d$ is other than hydrogen and m is 0;
—NHC(=O)—(CH$_2$)$_{1-4}$—;
—C(=O)NH(CR$^y$R$^z$)$_{2-5}$—;
and
—X$_1$—CH(R$^x$)—(CR$^y$R$^z$)$_{1-5}$—; such that when X$_1$ is a direct bond and W is C(R$_w$), then R$^x$ of CH(R$^x$) is hydrogen;

wherein X$_1$ is —NH—, O, S, or a direct bond; such that X$_1$ is other than 0 when W is N;
X$_2$ is —CH=CH—;
X$_3$ is O, S, NH, or C=O;
R$^x$, R$^y$, and R$^z$ are independently H or C$_{1-4}$alkyl;
and provided that L$_2$ in any instance does not exceed 7 atoms in length;
and further provided that when L$_2$ is —X$_2$—(CH$_2$)$_{0-4}$— or —C(=O)NH(CR$^y$R$^z$)$_{2-5}$—, then R$_W$ is hydrogen.

20. The compound according to claim 1 wherein L$_2$ is a bivalent radical selected from the group consisting of
—NH—C$_{5-6}$cycloalkyl-(CH$_2$)$_{0-2}$— provided that when C$_{5-6}$cycloalkyl is cyclohexyl, Q is attached at either the 2- or cis-4-position relative to the position of —NH—;
—X$_1$—CH(R$^x$)—(CR$^y$R$^z$)$_{1-5}$—, wherein X$_1$ is —NH—, O, or S and R$^x$, R$^y$, and R$^z$ are each hydrogen;
—C(=O)NH(CH$_2$)$_2$—;
and
—X$_1$—(R,R—CH(R$^x$)CR$^y$(R$^z$))—; wherein X$_1$ is —NH—, and R$^x$ and R$^z$ are methyl, and R$^y$ is hydrogen;
provided that when L$_2$ is —C(=O)NH(CH$_2$)$_2$—, then R$_W$ is hydrogen.

21. The compound according to claim 1 wherein L$_2$ is a bivalent radical selected from the group consisting of —NH-cyclohexyl-(CH$_2$)$_{0-2}$— and Q is attached at either the 2- or cis-4-position relative to the position of —NH—;
—X$_1$—CH(R$^x$)—(CR$^y$R$^z$)$_{1-5}$—; wherein X$_1$ is —NH— or S; and R$^x$, R$^y$, and R$^z$ are each hydrogen;
and
—X$_1$—(R,R—CH(R$^x$)CR$^y$ (R$^z$))—; wherein X$_1$ is —NH—, and R$^x$ and R$^z$ are methyl, and R$^y$ is hydrogen.

22. The compound according to claim 1 wherein L$_2$ is a bivalent radical selected from the group consisting of —NH-cyclohexyl-(CH$_2$)$_{0-2}$— and Q is attached at either the 2- or cis-4-position relative to the position of —NH—;
—X$_1$—CH(R$^x$)—(CR$^y$R$^z$)—; wherein X$_1$ is —NH— or S and R$^x$, R$^y$, and R$^z$ are each hydrogen;
and
—X$_1$—(R,R—CH(R$^x$)CR$^y$(R$^z$))—; wherein X$_1$ is —NH—, R$^x$ and R$^z$ are methyl, and R$^y$ is hydrogen.

23. The compound according to claim 1 wherein m is 0.

24. The compound according to claim 1 wherein R$^a$ and R$^d$ are independently hydrogen or C$_{1-6}$alkyl, wherein C$_{1-6}$alkyl is optionally substituted with one to three substituents independently selected from the group consisting of hydroxy, $C_{1-4}$alkoxy, fluoro, amino, $C_{1-4}$alkylamino, di$C_{1-4}$alkylamino, and $C_{1-4}$alkylcarbonyl; or $R^a$ and $R^c$ are taken together with the atoms to which they are attached to form a 5-8 membered monocyclic ring optionally substituted with oxo.

25. The compound according to claim 1 wherein $R^a$ and $R^d$ are independently hydrogen or $C_{1-3}$alkyl, wherein $C_{1-3}$alkyl is optionally substituted with one to three substituents independently selected from the group consisting of hydroxy, $C_{1-4}$alkoxy, fluoro, amino, $C_{1-4}$alkylamino, di$C_{1-4}$alkylamino, and $C_{1-4}$alkylcarbonyl; or $R^a$ and $R^c$ are taken together with the atoms to which they are attached to form a 5-8 membered monocyclic ring optionally substituted with oxo.

26. The compound according to claim 1 wherein $R^a$ and $R^d$ are independently hydrogen, methyl or ethyl; or $R^a$ and $R^c$ are taken together with the atoms to which they are attached to form a 5-8 membered monocyclic ring optionally substituted with oxo.

27. The compound according to claim 1 wherein $R^a$ and $R^d$ are independently hydrogen, methyl or ethyl.

28. The compound according to claim 1 wherein $R^b$ is hydrogen, $C_{1-6}$alkyl, $C_{2-6}$alkoxycarbonyl, or cyano; or, $R^b$ and $R^c$ are taken together with the atoms to which they are attached to form a 5-8 membered monocyclic ring, optionally substituted with oxo.

29. The compound according to claim 1 wherein $R^b$ is hydrogen or $C_{1-4}$alkyl; or, $R^b$ and $R^c$ are taken together with the atoms to which they are attached to form a 5-8 membered monocyclic ring, optionally substituted with oxo.

30. The compound according to claim 1 wherein $R^b$ is hydrogen.

31. The compound according to claim 1 wherein $R^c$ is hydrogen, $C_{1-10}$alkyl, $C_{2-10}$alkenyl, $C_{3-7}$cycloalkyl, adamantyl, amino, arylcarbonyl, aryl, heteroaryl, or heterocyclyl;
wherein $C_{1-10}$alkyl is optionally substituted with one to two substituents independently selected from the group consisting of $C_{1-4}$alkoxy, trifluoromethyl, aryl, heteroaryl, and heterocyclyl; and wherein any aryl- or heteroaryl-containing substituents of $R^c$ are optionally substituted with one to three substituents independently selected from the group consisting of $C_{1-6}$alkyl, $C_{1-6}$alkoxy, halogen, fluorinated $C_{1-6}$alkyl, fluorinated $C_{1-6}$alkoxy, $C_{1-6}$alkylcarbonyl, $C_{1-6}$alkoxycarbonyl, nitro, methylthio, hydroxy, and cyano; or, $R^c$ and $R^d$ are taken together with the atoms to which they are attached to form a 5-8 membered monocyclic ring that optionally includes 1 to 2 O or S heteroatoms within the ring, and said ring is optionally substituted with oxo.

32. The compound according to claim 1 wherein $R^c$ is hydrogen, $C_{1-6}$alkyl, $C_{2-6}$alkenyl, $C_{3-7}$cycloalkyl, adamantyl, heterocyclyl, arylcarbonyl, phenyl, or heteroaryl;
wherein $C_{1-6}$alkyl is optionally substituted with one to two substituents independently selected from the group consisting of $C_{1-3}$alkoxy, trifluoromethyl, phenyl, heteroaryl, and heterocyclyl; and wherein any aryl-, phenyl-, or heteroaryl-containing substituents of $R^c$ are optionally substituted with one to three substituents independently selected from the group consisting of $C_{1-6}$alkyl, $C_{1-6}$alkoxy, halogen, fluorinated $C_{1-6}$alkyl, fluorinated $C_{1-6}$alkoxy, $C_{1-6}$alkylcarbonyl, $C_{1-6}$alkoxycarbonyl, nitro, methylthio, hydroxy, and cyano; or, $R^c$ and $R^d$ are taken together with the atoms to which they are attached to form a 5-8 membered monocyclic ring and said ring is optionally substituted with oxo.

33. The compound according to claim 1 wherein $R^c$ is hydrogen, $C_{1-6}$alkyl, $C_{2-6}$alkenyl, $C_{3-7}$cycloalkyl, heterocyclyl, phenylcarbonyl, phenyl, or heteroaryl; wherein $C_{1-6}$alkyl is optionally substituted with one to two substituents independently selected from the group consisting of $C_{1-3}$alkoxy, phenyl, pyridinyl, furanyl, and tetrahydrofuranyl; and
wherein any phenyl- or heteroaryl-containing substituents of $R^c$ are optionally substituted with one to two substituents independently selected from the group consisting of $C_{1-6}$alkyl, $C_{1-6}$alkoxy, chloro, fluoro, bromo, fluorinated $C_{1-3}$alkoxy, nitro, methylthio, hydroxy, and cyano; or, $R^c$ and $R^d$ are taken together with the atoms to which they are attached to form a 5-8 membered monocyclic ring.

34. The compound according to claim 1 wherein $R^c$ is hydrogen, $C_{1-4}$alkyl, $C_{2-4}$alkenyl, cyclohexyl, phenylcarbonyl, phenyl, pyrimidinyl, furanyl, benzo[1,3]dioxolyl, or pyridinyl; wherein $C_{1-4}$alkyl is optionally substituted with one to two substituents independently selected from the group consisting of $C_{1-3}$alkoxy, phenyl, pyridinyl, furanyl, and tetrahydrofuranyl; and wherein any phenyl- or heteroaryl-containing substituents of $R^c$ are optionally substituted with one to two substituents independently selected from the group consisting of $C_{1-6}$alkyl, $C_{1-6}$alkoxy, chloro, fluoro, bromo, fluorinated $C_{1-3}$alkoxy, nitro, methylthio, hydroxy, and cyano; or, $R^c$ and $R^d$ are taken together with the atoms to which they are attached to form a 5-8 membered monocyclic ring.

35. The compound according to claim 1 wherein $R^c$ is hydrogen, $C_{1-4}$alkyl, $C_{2-4}$alkenyl, cyclohexyl, phenylcarbonyl, phenyl, pyrimidinyl, furanyl, benzo[1,3]dioxolyl, or pyridinyl; wherein $C_{1-4}$alkyl is optionally substituted with one to two substituents independently selected from the group consisting of methoxy, phenyl, pyridinyl, furanyl, and tetrahydrofuranyl; and wherein any phenyl- or heteroaryl-containing substituents of $R^c$ are optionally substituted with one to two substituents independently selected from the group consisting of $C_{1-3}$alkyl, $C_{1-3}$alkoxy, chloro, fluoro, bromo, trifluoromethoxy, nitro, hydroxy, and cyano; or, $R^c$ and $R^d$ are taken together with the atoms to which they are attached to form a 5-6 membered monocyclic ring.

36. A compound of Formula (Ia):

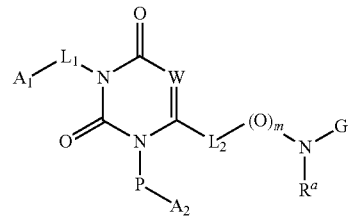

Formula (Ia)

wherein:
$A_1$ is hydrogen; aryl; heteroaryl; $C_{5-8}$cycloalkyl; or heterocyclyl provided that $A_1$ is other than piperidin-4-yl, N-t-butoxycarbonyl-piperidin-4-yl, or N-methyl-piperidin-3-yl; and wherein substituents of $A_1$ other than hydrogen are optionally substituted with one to three substituents independently selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, cyano, hydroxy, aminocarbonyl, $C_{1-6}$alkylaminocarbonyl, di($C_{1-6}$alkyl)aminocarbonyl, and $C_{1-6}$alkylcarbonyl;

$L_1$ is —$(CH_2)_r$— optionally substituted with one to three substituents independently selected from the group consisting of $C_{1-6}$alkyl, $C_{2-6}$alkenyl, $C_{2-6}$alkynyl, and halogen; provided that when $A_1$ is hydrogen, r is greater than or equal to 4;

r is an integer of 1 to 5;

P is —$(CH_2)_{4-6}$— when $A_2$ is hydrogen; and P is —$(CH_2)_{1-2}$— or —$CH_2CH=CH$— when $A_2$ is other than hydrogen;

$A_2$ is hydrogen, heteroaryl other than unsubstituted pyridin-2-yl, $C_{3-8}$cycloalkyl, or phenyl optionally substituted at the meta and para positions with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, cyano, hydroxy, nitro, aminocarbonyl, $C_{1-6}$alkylcarbonylamino, and a non fused $C_{3-6}$cycloalkyloxy; wherein heteroaryl other than unsubstituted pyridin-2-yl and $C_{3-8}$cycloalkyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, cyano, hydroxy, nitro, aminocarbonyl, $C_{1-6}$alkylcarbonylamino, and a non fused $C_{3-6}$cycloalkyloxy;

provided that no more than two substituents on $A_2$ are aryl($C_{1-6}$)alkoxy, phenyl, or a non fused $C_{3-6}$cycloalkyloxy;

provided that when $A_1$ is unsubstituted phenyl and $L_2$ is —$X_1$—$CH(R^x)$—$(CR^yR^z)$— wherein $X_1$ is NH and $R^x$, $R^y$, and $R^z$ are each hydrogen, $A_2$ is other than unsubstituted phenyl; phenyl substituted with aryl($C_{1-6}$)alkoxy or phenyl; or phenyl substituted at the meta position with cyano;

and, further provided that when $A_1$ is unsubstituted phenyl and $L_2$ is —$X_1$—$CH(R^x)$—$(CR^yR^z)_2$— wherein $X_1$ is NH and $R^x$, $R^y$, and $R^z$ are each hydrogen, $A_2$ is other than phenyl substituted with methoxy;

and, provided that when $A_1$ is 3,4-dichloro-phenyl and P is —$CH_2$—, $A_2$ is other than phenyl substituted at the meta position with trifluoromethyl or trifluoromethoxy;

and, further provided that when $A_1$ is 3,4-dichloro-phenyl and P is —$(CH_2)_2$—, $A_2$ is other than 4-methoxy-phenyl;

W is CH;

$L_2$ is a bivalent radical selected from the group consisting of

—NH—$C_{5-7}$cycloalkyl-$(CH_2)_{0-2}$—; provided that when $C_{5-7}$cycloalkyl is cyclohexyl, Q is attached at either the 2- or cis-4-position relative to the position of —NH—;

—$X_2$—$(CH_2)_{0-4}$—;

—$X_1$—$(CH_2)_{2-3}$—$X_3$—$(CH_2)_{2-3}$—;

—NH$(CH_2)_{1-4}$C(=O)— provided that at least one of $R^b$, $R^c$, or $R^d$ is other than hydrogen and m is 0;

—NHC(=O)—$(CH_2)_{1-4}$—;

—C(=O)NH$(CR^yR^z)_{2-5}$;

and

—$X_1$—$CH(R^x)$—$(CR^yR^z)_{1-5}$—; such that when $X_1$ is a direct bond and W is C($R_w$), then $R^x$ of $CH(R^x)$ is hydrogen;

wherein $X_1$ is —NH—, O, S, or a direct bond; such that $X_1$ is other than 0 when W is N;

$X_2$ is —CH=CH—;

$X_3$ is O, S, NH, or C=O;

$R^x$, $R^y$, and $R^z$ are independently H or $C_{1-4}$alkyl;

and provided that $L_2$ in any instance does not exceed 7 atoms in length;

and further provided that when $L_2$ is —$X_2$—$(CH_2)_{0-4}$— or —C(=O)NH$(CR^yR^z)_{2-5}$—, then $R_W$ is hydrogen;

m is 0 or 1;

G is —C(=$NR^b$)$NR^cR^d$;

$R^a$ and $R^d$ are independently hydrogen or $C_{1-6}$alkyl, wherein $C_{1-6}$alkyl is optionally substituted with one to three substituents independently selected from the group consisting of hydroxy, $C_{1-4}$alkoxy, fluoro, amino, $C_{1-4}$alkylamino, di$C_{1-4}$alkylamino, and $C_{1-4}$alkylcarbonyl; or $R^a$ and $R^c$ are taken together with the atoms to which they are attached to form a 5-8 membered monocyclic ring optionally substituted with oxo;

$R^b$ is hydrogen, $C_{1-6}$alkyl, $C_{2-6}$alkoxycarbonyl, or cyano; or, $R^b$ and $R^c$ are taken together with the atoms to which they are attached to form a 5-8 membered monocyclic ring optionally substituted with oxo;

$R^c$ is hydrogen, $C_{1-10}$alkyl, $C_{2-10}$alkenyl, $C_{3-7}$cycloalkyl, adamantyl, amino, arylcarbonyl, aryl, heteroaryl, or heterocyclyl; wherein $C_{1-10}$alkyl is optionally substituted with one to two substituents independently selected from the group consisting of $C_{1-4}$alkoxy, trifluoromethyl, aryl, heteroaryl, and heterocyclyl; and wherein any aryl- or heteroaryl-containing substituents of $R^c$ are optionally substituted with one to three substituents independently selected from the group consisting of $C_{1-6}$alkyl, $C_{1-6}$alkoxy, halogen, fluorinated $C_{1-6}$alkyl, fluorinated $C_{1-6}$alkoxy, $C_{1-6}$alkylcarbonyl, $C_{1-6}$alkoxycarbonyl, nitro, methylthio, hydroxy, and cyano; or, $R^c$ and $R^d$ are taken together with the atoms to which they are attached to form a 5-8 membered monocyclic ring that optionally includes 1 to 2 O or S heteroatoms within the ring, and said ring is optionally substituted with oxo;

with the proviso that in any instance, only one ring optionally exists between $R^a$ and $R^b$, $R^b$ and $R^c$, or $R^c$ and $R^d$;

and an enantiomer, a diastereomer, a tautomer, or a pharmaceutically acceptable salt thereof.

37. A compound of Formula (Ia)

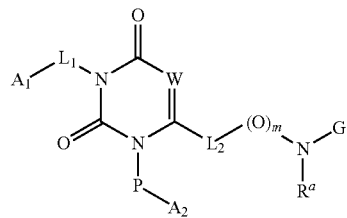

Formula (Ia)

wherein:

$A_1$ is hydrogen; aryl; heteroaryl; $C_{5-8}$cycloalkyl; or heterocyclyl other than piperidinyl;

wherein substituents of $A_1$ other than hydrogen are optionally substituted with one to three substituents independently selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, cyano, hydroxy, aminocarbonyl, $C_{1-6}$alkylaminocarbonyl, di($C_{1-6}$alkyl)aminocarbonyl, and $C_{1-6}$alkylcarbonyl;

$L_1$ is —(CH$_2$)$_r$— optionally substituted with a substituent selected from the group consisting of C$_{1-4}$alkyl, C$_{2-4}$alkenyl, and C$_{2-4}$alkynyl; provided that r is 1 to 3 when A$_1$ is other than hydrogen; or r is 4 or 5 when A$_1$ is hydrogen;

P is —CH$_2$—;

A$_2$ is heteroaryl other than unsubstituted pyridin-2-yl, a non fused C$_{3-8}$cycloalkyl, or phenyl optionally substituted at the meta and para positions with one to three substituents independently selected from the group consisting of C$_{1-6}$alkyl, C$_{1-6}$alkoxy, halogen, halogenated C$_{1-6}$alkyl, halogenated C$_{1-6}$alkoxy, C$_{1-6}$alkylthio, C$_{1-6}$alkoxycarbonyl, amino, hydroxy, nitro, aminocarbonyl, C$_{1-6}$alkylcarbonylamino, and a non fused C$_{3-6}$cycloalkyloxy; wherein heteroaryl other than unsubstituted pyridin-2-yl and a non fused C$_{3-8}$cycloalkyl are optionally substituted with one to three substituents independently selected from the group consisting of C$_{1-6}$alkyl, C$_{1-6}$alkoxy, halogen, halogenated C$_{1-6}$alkyl, halogenated C$_{1-6}$alkoxy, C$_{1-6}$alkylthio, C$_{1-6}$alkoxycarbonyl, amino, hydroxy, nitro, aminocarbonyl, C$_{1-6}$alkylcarbonylamino, and a non fused C$_{3-6}$cycloalkyloxy;

provided that no more than two substituents on A$_2$ are non fused C$_{3-6}$cycloalkyloxy;

provided that when A$_1$ is unsubstituted phenyl and L$_2$ is —X$_1$—CH(R$^x$)—(CR$^y$R$^z$)— wherein X$_1$ is —NH— or S and R$^x$, R$^y$, and R$^z$ are each hydrogen, A$_2$ is other than unsubstituted phenyl;

and, further provided that when A$_1$ is unsubstituted phenyl and L$_2$ is —X$_1$—CH(R$^x$)—(CR$^y$R$^z$)$_2$— wherein X$_1$ is NH and R$^x$, R$^y$, and R$^z$ are each hydrogen, A$_2$ is other than phenyl substituted with methoxy;

and, further provided that when A$_1$ is 3,4-dichloro-phenyl, A$_2$ is other than phenyl substituted at the meta position with trifluoromethoxy;

W is CH;

L$_2$ is a bivalent radical selected from the group consisting of

—NH—C$_{5-6}$cycloalkyl-(CH$_2$)$_{0-2}$—; provided that when C$_{5-6}$cycloalkyl is cyclohexyl, Q is attached at either the 2- or cis-4-position relative to the position of —NH—;

—X$_1$—CH(R$^x$)—(CR$^y$R$^z$)$_{1-5}$—, wherein X$_1$ is —NH—, O, or S; and R$^x$, R$^y$, and R$^z$ are each hydrogen;

—C(═O)NH(CH$_2$)$_2$—; and

—X$_1$—(R,R—CH(R$^x$)CR$^y$(R$^z$))—; wherein X$_1$ is —NH—, and R$^x$ and R$^z$ are methyl, and R$^y$ is hydrogen;

provided that when L$_2$ is —C(═O)NH(CH$_2$)$_2$—, then R$_W$ of W is hydrogen;

m is 0 or 1;

G is —C(═NR$^b$)NR$^c$R$^d$;

R$^a$ and R$^d$ are independently hydrogen or C$_{1-3}$alkyl, wherein C$_{1-3}$alkyl is optionally substituted with one to three substituents independently selected from the group consisting of hydroxy, C$_{1-4}$alkoxy, fluoro, amino, C$_{1-4}$alkylamino, diC$_{1-4}$alkylamino, and C$_{1-4}$alkylcarbonyl; or R$^a$ and R$^c$ are taken together with the atoms to which they are attached to form a 5-8 membered monocyclic ring optionally substituted with oxo;

R$^b$ is hydrogen or C$_{1-4}$alkyl; or, R$^b$ and R$^c$ are taken together with the atoms to which they are attached to form a 5-8 membered monocyclic ring, optionally substituted with oxo;

R$^c$ is hydrogen, C$_{1-6}$alkyl, C$_{2-6}$alkenyl, C$_{3-7}$cycloalkyl, adamantyl, heterocyclyl, arylcarbonyl, phenyl, or heteroaryl; wherein C$_{1-6}$alkyl is optionally substituted with one to two substituents independently selected from the group consisting of C$_{1-3}$alkoxy, trifluoromethyl, phenyl, heteroaryl, and heterocyclyl; and wherein any aryl-, phenyl-, or heteroaryl-containing substituents of R$^c$ are optionally substituted with one to three substituents independently selected from the group consisting of C$_{1-6}$alkyl, C$_{1-6}$alkoxy, halogen, fluorinated C$_{1-6}$alkyl, fluorinated C$_{1-6}$alkoxy, C$_{1-6}$alkylcarbonyl, C$_{1-6}$alkoxycarbonyl, nitro, methylthio, hydroxy, and cyano; or, R$^c$ and R$^d$ are taken together with the atoms to which they are attached to form a 5-8 membered monocyclic ring and said ring is optionally substituted with oxo;

with the proviso that in any instance, only one ring optionally exists between R$^a$ and R$^b$, R$^b$ and R$^c$, or R$^c$ and R$^d$;

and an enantiomer, a diastereomer, a tautomer, or a pharmaceutically acceptable salt thereof.

38. A compound of Formula (Ia)

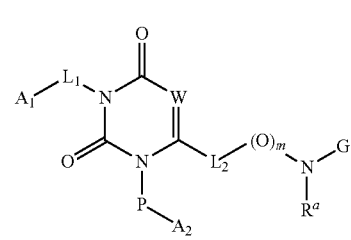

Formula (Ia)

wherein:

A$_1$ is substituted phenyl, benzofuranyl, thiazolyl, or thiophenyl; wherein phenyl is substituted with, and benzofuranyl, thiazolyl, and thiophenyl are optionally substituted with, one to two substituents independently selected from the group consisting of C$_{1-4}$alkyl, C$_{1-4}$alkoxy, halogen, nitro, halogenated C$_{1-4}$alkyl, halogenated C$_{1-4}$alkoxy, methylthio, amino, cyano, and C$_{1-4}$alkylcarbonyl;

L$_1$ is —(CH$_2$)$_r$— optionally substituted with a substituent selected from the group consisting of methyl and allyl, and r is 1 to 3;

P is —CH$_2$—;

A$_2$ is pyridin-3-yl, pyridin-4-yl, or phenyl optionally substituted at the meta and para positions with one to two substituents independently selected from the group consisting of methyl, ethyl, methoxy, ethoxy, isopropyloxy, trifluoromethoxy, difluoromethoxy, hydroxy, aminocarbonyl, and methylcarbonylamino; wherein pyridin-3-yl and pyridin-4-yl are optionally substituted with one to two substituents independently selected from the group consisting of methyl, ethyl, methoxy, ethoxy, isopropyloxy, trifluoromethoxy, difluoromethoxy, hydroxy, aminocarbonyl, and methylcarbonylamino;

W is CH;

L$_2$ is a bivalent radical selected from the group consisting of

—NH-cyclohexyl-(CH$_2$)$_{0-2}$— and Q is attached at either the 2- or cis-4-position relative to the position of —NH—;

—X$_1$—CH(R$^x$)—(CR$^y$R$^z$)$_{1-5}$—; wherein X$_1$ is —NH— or S; and R$^x$, R$^y$, and R$^z$ are each hydrogen; and —X$_1$—(R,R—CH(R$^x$)C R$^y$(R$^z$))—; wherein X$_1$ is —NH—, and R$^x$ and R$^z$ are methyl, and R$^y$ is hydrogen;

m is 0;

G is —C(═NR$^b$)NR$^c$R$^d$;

$R^a$ and $R^d$ are independently hydrogen, methyl or ethyl; or $R^a$ and $R^c$ are taken together with the atoms to which they are attached to form a 5-8 membered monocyclic ring optionally substituted with oxo;

$R^b$ is hydrogen;

$R^c$ is hydrogen, $C_{1-6}$alkyl, $C_{2-6}$alkenyl, $C_{3-7}$cycloalkyl, heterocyclyl, phenylcarbonyl, phenyl, or heteroaryl; wherein $C_{1-6}$alkyl is optionally substituted with one to two substituents independently selected from the group consisting of $C_{1-3}$alkoxy, phenyl, pyridinyl, furanyl, and tetrahydrofuranyl; and wherein any phenyl- or heteroaryl-containing substituents of $R^c$ are optionally substituted with one to two substituents independently selected from the group consisting of $C_{1-6}$alkyl, $C_{1-6}$alkoxy, chloro, fluoro, bromo, fluorinated $C_{1-3}$alkoxy, nitro, methylthio, hydroxy, and cyano; or, $R^c$ and $R^d$ are taken together with the atoms to which they are attached to form a 5-8 membered monocyclic ring;

and an enantiomer, a diastereomer, a tautomer, or a pharmaceutically acceptable salt thereof.

39. A compound of Formula (Ia)

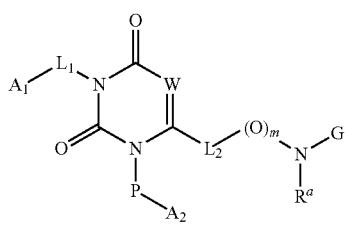

Formula (Ia)

wherein:

$A_1$ is phenyl or benzofuranyl; wherein phenyl is substituted at either the 4-position or 3- and 4-positions with one to two substituents independently selected from the group consisting of ethyl, methoxy, fluoro, chloro, nitro, difluoromethoxy, and methylthio;

$L_1$ is —$CH_2$— optionally substituted with methyl or allyl;

P is —$CH_2$—, $A_2$ is phenyl substituted at the para position with a substituent selected from the group consisting of methoxy, ethoxy, isopropyloxy, difluoromethoxy, hydroxy, and aminocarbonyl;

or $A_2$ is pyridin-3-yl or pyridin-4-yl substituted with methoxy;

W is CH;

$L_2$ is a bivalent radical selected from the group consisting of

—NH-cyclohexyl-$(CH_2)_{0-2}$— and Q is attached at either the 2- or cis-4-position relative to the position of —NH—;

—$X_1$—$CH(R^x)$—$(CR^yR^z)$—; wherein $X_1$ is —NH— or S; and $R^x$, $R^y$, and $R^z$ are each hydrogen; and —$X_1$—(R,R—$CH(R^x)CR^y(R^z)$)—; wherein $X_1$ is —NH—, and $R^x$ and $R^z$ are methyl, and $R^y$ is hydrogen;

m is 0;

G is —$C(=NR^b)NR^cR^d$;

$R^a$ and $R^d$ are independently hydrogen, methyl or ethyl;

$R^b$ is hydrogen;

$R^c$ is hydrogen, $C_{1-4}$alkyl, $C_{2-4}$alkenyl, cyclohexyl, phenylcarbonyl, phenyl, pyrimidinyl, furanyl, benzo[1,3] dioxolyl, or pyridinyl; wherein $C_{1-4}$alkyl is optionally substituted with one to two substituents independently selected from the group consisting of $C_{1-3}$alkoxy, phenyl, pyridinyl, furanyl, and tetrahydrofuranyl; and wherein any phenyl- or heteroaryl-containing substituents of $R^c$ are optionally substituted with one to two substituents independently selected from the group consisting of $C_{1-6}$alkyl, $C_{1-6}$alkoxy, chloro, fluoro, bromo, fluorinated $C_{1-3}$alkoxy, nitro, methylthio, hydroxy, and cyano; or, $R^c$ and $R^d$ are taken together with the atoms to which they are attached to form a 5-8 membered monocyclic ring;

and an enantiomer, a diastereomer, a tautomer, or a pharmaceutically acceptable salt thereof.

40. A compound according to claim 1 selected from the group consisting of:

a compound of Formula (I) wherein $A_1$ is phenyl, $L_1$ is —$CH_2$—, D is —$CH_2$-(4-methoxy-phenyl), W is CH, $L_2$ is —$NH(CH_2)_2$—, and Q is —$NHC(=NH)NH_2$;

a compound of Formula (I) wherein $A_1$ is 4-methoxy-phenyl, $L_1$ is —$CH_2$—, D is —$CH_2$-(4-methoxy-phenyl), W is CH, $L_2$ is —$NH(CH_2)_2$—, and Q is —$NHC(=NH)NH_2$;

a compound of Formula (I) wherein $A_1$ is 4-methoxy-phenyl, $L_1$ is —$CH_2$—, D is —$CH_2$-(4-methoxy-phenyl), W is CH, $L_2$ is —$C(=O)NH(CH_2)_2$—, and Q is —$NHC(=NH)NH_2$;

a compound of Formula (I) wherein $A_1$ is 4-methoxy-phenyl, $L_1$ is —$CH_2$—, D is —$CH_2$-(4-methoxy-phenyl), W is CH, $L_2$ is —$O(CH_2)_2$—, and Q is —$NHC(=NH)NH_2$;

a compound of Formula (I) wherein $A_1$ is 4-methoxy-phenyl, $L_1$ is —$CH_2$—, D is —$CH_2$-(4-methoxy-phenyl), W is CH, $L_2$ is —$S(CH_2)_2$—, and Q is —$NHC(=NH)NH_2$; and a compound of Formula (I) wherein $A_1$ is 4-methoxy-phenyl, $L_1$ is —$CH_2$—, D is —$CH_2$-(4-methoxy-phenyl), W is CH, $L_2$ is —$(CH_2)_3$—, and Q is —$NHC(=NH)NH_2$.

41. A pharmaceutical composition comprising a compound, salt or solvate according to any of claim 1 admixed with a pharmaceutically acceptable carrier, excipient or diluent.

42. A veterinary composition comprising a compound, salt or solvate according to claim 1 admixed with a veterinarily acceptable carrier, excipient or diluent.

43. A method of treating irritable bowel syndrome and inflammatory bowel disease in a mammal which method comprises administering to a mammal in need thereof a therapeutically effective amount of a compound or salt of claim 1.

44. The method of claim 43 wherein the irritable bowel syndrome is diarrhea—predominant, or alternating diarrhea/constipation and the inflammatory bowel disease is ulcerative colitis or Crohn's disease.

45. The method of claim 43 wherein said therapeutically effective amount comprises a dose range of from about 0.1 mg to about 1,000 mg.

46. The method of claim 43 wherein said therapeutically effective amount comprises a dose range of from about 50 mg to about 1000 mg.

47. The method of claim 43 wherein said therapeutically effective amount comprises a dose range of from about 100 mg to about 1000 mg.

* * * * *